(12) United States Patent
Beaulieu et al.

(10) Patent No.: US 7,803,944 B2
(45) Date of Patent: Sep. 28, 2010

(54) VIRAL POLYMERASE INHIBITORS

(75) Inventors: Pierre Louis Beaulieu, Laval (CA); Gulrez Fazal, Laval (CA); George Kukolj, Laval (CA); Eric Jolicoeur, Laval (CA); James Gillard, Laval (CA); Marc-Andre Poupart, Laval (CA); Jean Rancourt, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 11/464,651

(22) Filed: Aug. 15, 2006

(65) Prior Publication Data

US 2006/0293306 A1 Dec. 28, 2006

Related U.S. Application Data

(62) Division of application No. 10/198,680, filed on Jul. 18, 2002, now Pat. No. 7,157,486.

(60) Provisional application No. 60/307,674, filed on Jul. 25, 2001, provisional application No. 60/338,061, filed on Dec. 7, 2001.

(51) Int. Cl.
*C07D 471/04* (2006.01)
*A61K 31/407* (2006.01)
*A61K 31/4353* (2006.01)
*A61K 31/12* (2006.01)
*C07D 487/04* (2006.01)

(52) U.S. Cl. .................. 546/113; 514/300; 514/415; 548/508

(58) Field of Classification Search .............. 546/113; 514/300
See application file for complete search history.

(56) References Cited

U.S. PATENT DOCUMENTS

| | | | |
|---|---|---|---|
| 3,565,912 A | 2/1971 | Szmuszkovicz | |
| 4,003,908 A | 1/1977 | Denzel et al. | |
| 4,146,725 A | 3/1979 | Meyer et al. | |
| 4,250,317 A | 2/1981 | Meyer et al. | |
| 4,252,803 A | 2/1981 | Webb | |
| 4,264,325 A | 4/1981 | Meyer et al. | |
| 4,360,679 A | 11/1982 | Meyer et al. | |
| 4,384,121 A | 5/1983 | Meyer | |
| 4,432,886 A | 2/1984 | Meyer | |
| 4,433,975 A | 2/1984 | Meyer | |
| 4,590,200 A | 5/1986 | Cross et al. | |
| 4,740,519 A | 4/1988 | Shroot et al. | |
| 4,859,684 A | 8/1989 | Raeymaekers et al. | |
| 4,898,863 A | 2/1990 | Brown et al. | |
| 4,920,140 A | 4/1990 | Shroot et al. | |
| 5,059,621 A | 10/1991 | Shroot et al. | |
| 5,216,003 A | 6/1993 | Vazquez | |
| 5,410,061 A | 4/1995 | Gilmore et al. | |
| 5,482,956 A | 1/1996 | Lunkenheimer et al. | |
| 5,527,819 A | 6/1996 | Williams et al. | |
| 5,661,159 A | 8/1997 | Matsuo et al. | |
| 5,817,689 A | 10/1998 | Kato et al. | |
| 5,866,594 A | 2/1999 | Endo et al. | |
| 5,912,260 A | 6/1999 | Kalindjian et al. | |
| 5,932,743 A | 8/1999 | Collini et al. | |
| 6,063,806 A | 5/2000 | Kamiya et al. | |
| 6,069,156 A | 5/2000 | Oku et al. | |
| 6,169,107 B1 | 1/2001 | Kitano et al. | |
| 6,184,238 B1 | 2/2001 | Takano et al. | |
| 6,228,868 B1 | 5/2001 | Gwaltney et al. | |
| 6,358,992 B1 | 3/2002 | Pamukcu et al. | |
| 6,399,644 B1 | 6/2002 | Wexler et al. | |
| 6,448,281 B1 | 9/2002 | Beaulieu et al. | |
| 6,455,525 B1 | 9/2002 | Singh et al. | |

(Continued)

FOREIGN PATENT DOCUMENTS

CA 1111695 11/1981

(Continued)

OTHER PUBLICATIONS

Zimmermann et al., Archiv der Pharmazie (Weinheim, Germany) (1976), 309(7), 597-600; CA 86: 43587, 1977.*

(Continued)

*Primary Examiner*—Venkataraman Balasubramanian
(74) *Attorney, Agent, or Firm*—Michael P. Morris; Mary-Ellen M. Devlin; David A. Dow

(57) ABSTRACT

An isomer, enantiomer, diastereoisomer, or tautomer of a compound, represented by formula I:

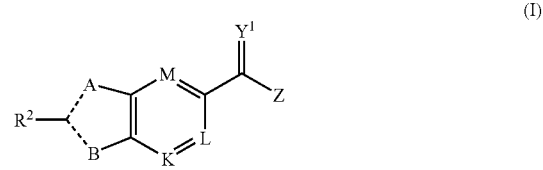

(I)

wherein:
A is O, S, $NR^1$, or $CR^1$, wherein $R^1$ is defined herein;
— represents either a single or a double bond;
$R^2$ is selected from: H, halogen, $R^{21}$, $OR^{21}$, $SR^{21}$, $COOR^{21}$, $SO_2N(R^{22})_2$, $N(R^{22})_2$, $CON(R^{22})_2$, $NR^{22}C(O)R^{22}$ or $NR^{22}C(O)NR^{22}$ wherein $R^{21}$ and each $R^{22}$ is defined herein;
B is $NR^3$ or $CR^3$, with the proviso that one of A or B is either $CR^1$ or $CR^3$, wherein $R^3$ is defined herein;
K is N or $CR^4$, wherein $R^4$ is defined herein;
L is N or $CR^5$ wherein $R^5$ has the same definition as $R^4$ defined above;
M is N or $CR^7$, wherein $R^7$ has the same definition as $R^4$ defined above;
$Y^1$ is O or S;
Z is $N(R^{6a})R^6$ or $OR^6$, wherein $R^{6a}$ is H or alkyl or $NR^{61}R^{62}$ wherein $R^{61}$ and $R^{62}$ are defined herein;
a salt or a derivative thereof, as an inhibitor of HCV NS5B polymerase.

31 Claims, No Drawings

U.S. PATENT DOCUMENTS

| | | |
|---|---|---|
| 6,479,508 B1 | 11/2002 | Beaulieu et al. |
| 6,579,882 B2 | 6/2003 | Stewart et al. |
| 6,770,643 B2 * | 8/2004 | Cox et al. ................. 514/234.2 |
| 6,770,666 B2 | 8/2004 | Hashimoto et al. |
| 6,794,404 B2 | 9/2004 | Beaulieu et al. |
| 6,841,566 B2 | 1/2005 | Beaulieu et al. |
| 6,897,207 B2 * | 5/2005 | Cox et al. ................... 514/183 |
| 7,098,231 B2 | 8/2006 | Poupart et al. |
| 7,112,600 B1 | 9/2006 | Hashimoto et al. |
| 7,141,574 B2 | 11/2006 | Beaulieu et al. |
| 7,157,486 B2 | 1/2007 | Beaulieu et al. |
| 7,223,785 B2 | 5/2007 | Beaulieu et al. |
| 7,241,801 B2 | 7/2007 | Beaulieu et al. |
| 7,323,470 B2 * | 1/2008 | Poupart et al. ......... 514/255.05 |
| 7,332,614 B2 | 2/2008 | Khodabocus et al. |
| 2001/0039286 A1 | 11/2001 | Dinnell et al. |
| 2002/0173527 A1 | 11/2002 | Astles |
| 2003/0050320 A1 | 3/2003 | Hashimoto et al. |
| 2003/0108862 A1 | 6/2003 | Kukolj et al. |
| 2003/0134853 A1 | 7/2003 | Priestley et al. |
| 2004/0082635 A1 | 4/2004 | Hashimoto et al. |
| 2004/0097438 A1 | 5/2004 | Hashimoto et al. |
| 2004/0110126 A1 | 6/2004 | Kukolj et al. |
| 2004/0171833 A1 | 9/2004 | Buchwald et al. |
| 2004/0224955 A1 | 11/2004 | Beaulieu et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2006/0160798 A1 | 7/2006 | Beaulieu et al. |
| 2006/0183752 A1 | 8/2006 | Khodabocus et al. |
| 2006/0293306 A1 | 12/2006 | Beaulieu et al. |
| 2007/0142380 A1 | 6/2007 | Beaulieu et al. |
| 2007/0249629 A1 | 10/2007 | Beaulieu et al. |
| 2008/0119490 A1 | 5/2008 | Poupart et al. |
| 2009/0087409 A1 | 4/2009 | Beaulieu et al. |
| 2009/0170859 A1 | 7/2009 | Tsantrizos et al. |

FOREIGN PATENT DOCUMENTS

| | | |
|---|---|---|
| CA | 2150812 | 6/1994 |
| CA | 2158996 | 10/1994 |
| CA | 2143040 | 8/1995 |
| CA | 2124169 | 11/1995 |
| CA | 2164394 | 6/1996 |
| CA | 2223585 | 12/1996 |
| CA | 2241186 | 6/1997 |
| CA | 2 389 165 A1 | 5/2001 |
| CA | 2363274 | 7/2001 |
| CA | 2412718 | 1/2002 |
| CA | 2448737 | 1/2003 |
| CA | 2449180 | 2/2003 |
| CH | 511873 | 8/1971 |
| DE | 2641060 | 3/1978 |
| DE | 3522230 | 1/1987 |
| DE | 19507913 | 9/1996 |
| EP | 10063 | 4/1980 |
| EP | 0011824 | 6/1980 |
| EP | 12291 | 6/1980 |
| EP | 14411 | 8/1980 |
| EP | 0050957 A1 | 10/1981 |
| EP | 0073663 A2 | 8/1982 |
| EP | 209707 | 1/1987 |
| EP | 0 242 167 A2 | 10/1987 |
| EP | 318084 | 5/1989 |
| EP | 353606 | 2/1990 |
| EP | 429240 | 5/1991 |
| EP | 439356 | 7/1991 |
| EP | 459334 | 12/1991 |
| EP | 539117 | 4/1993 |
| EP | 546713 | 6/1993 |
| EP | 549175 | 6/1993 |
| EP | 563910 | 10/1993 |
| EP | 583665 | 2/1994 |
| EP | 607439 | 7/1994 |
| EP | 615159 | 9/1994 |
| EP | 750226 | 12/1996 |
| EP | 0801059 | 10/1997 |
| EP | 0 987 250 A1 | 3/2000 |
| EP | 1142880 | 10/2001 |
| EP | 1 162 196 A1 | 12/2001 |
| EP | 1256628 | 11/2002 |
| FR | 1604809 | 4/1972 |
| FR | 2291749 | 6/1976 |
| GB | 1094903 | 12/1967 |
| GB | 1186504 | 4/1970 |
| GB | 1436089 | 5/1976 |
| GB | 1509527 | 5/1978 |
| GB | 2118552 A | 4/1983 |
| GB | 2164648 | 3/1986 |
| GB | 2197320 | 5/1988 |
| GB | 2203420 | 10/1988 |
| JP | 60-149502 A | 8/1985 |
| JP | 61-85360 A | 4/1986 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 06239841 | 8/1994 |
| JP | 6297858 | 10/1994 |
| JP | 7140604 | 6/1995 |
| JP | 7228530 | 8/1995 |
| JP | 09124632 A | 5/1997 |
| JP | 9328678 | 12/1997 |
| JP | 10-67682 | 3/1998 |
| JP | 10-67682 A | 3/1998 |
| JP | 10-114654 | 5/1998 |
| JP | 10-114654 A | 5/1998 |
| JP | 10204059 | 8/1998 |
| JP | 10265478 | 10/1998 |
| JP | 11021693 | 1/1999 |
| JP | 115003445 | 3/1999 |
| JP | 11177218 | 7/1999 |
| JP | 3-100165 A | 10/2000 |
| JP | 2001-122855 A | 5/2001 |
| JP | 2001 122855 A | 5/2001 |
| WO | 9116313 | 10/1991 |
| WO | 9210097 | 6/1992 |
| WO | 9306828 | 4/1993 |
| WO | 9411349 | 5/1994 |
| WO | 9507263 | 3/1995 |
| WO | 96/16938 A1 | 6/1996 |
| WO | WO 96/32379 | 10/1996 |
| WO | 9639391 | 12/1996 |
| WO | 9712613 | 4/1997 |
| WO | 97/44319 A1 | 11/1997 |
| WO | 97/48697 A1 | 12/1997 |
| WO | WO 97/48697 A1 | 12/1997 |
| WO | 9801436 | 1/1998 |
| WO | WO 98/08847 A1 | 3/1998 |
| WO | WO 98/29408 | 7/1998 |
| WO | 98/37069 A1 | 8/1998 |
| WO | 9837079 | 8/1998 |
| WO | 99/28297 A1 | 6/1999 |
| WO | 99/29660 A1 | 6/1999 |
| WO | 99/29661 A1 | 6/1999 |
| WO | 9929843 A1 | 6/1999 |
| WO | WO 99/28297 A1 | 6/1999 |
| WO | 9951781 | 10/1999 |
| WO | 9961020 | 12/1999 |
| WO | 9965886 | 12/1999 |
| WO | 00/06529 A1 | 2/2000 |

| | | |
|---|---|---|
| WO | 0006566 | 2/2000 |
| WO | WO 00/06529 A1 | 2/2000 |
| WO | WO 00/06556 | 2/2000 |
| WO | 00/10573 A1 | 3/2000 |
| WO | 00/13708 A1 | 3/2000 |
| WO | WO 00/10573 A1 | 3/2000 |
| WO | WO 00/13708 A1 | 3/2000 |
| WO | 00/18231 A1 | 4/2000 |
| WO | WO 00/18231 A1 | 4/2000 |
| WO | WO 00/26202 A1 | 5/2000 |
| WO | WO 00/27846 A2 | 5/2000 |
| WO | WO 01/30774 A1 | 3/2001 |
| WO | 01/30774 A1 | 5/2001 |
| WO | WO 01/32653 A1 | 5/2001 |
| WO | 01/47922 A2 | 7/2001 |
| WO | 0151487 | 7/2001 |
| WO | WO 01/47883 A1 | 7/2001 |
| WO | WO 01/47922 A2 | 7/2001 |
| WO | 0185172 | 11/2001 |
| WO | 0190121 | 11/2001 |
| WO | WO 01/87885 A1 | 11/2001 |
| WO | 0206246 | 1/2002 |
| WO | WO 02/04425 A2 | 1/2002 |
| WO | 02057287 | 7/2002 |
| WO | 02057425 | 7/2002 |
| WO | 02/059118 A1 | 8/2002 |
| WO | 02069903 | 9/2002 |
| WO | 02070739 | 9/2002 |
| WO | 02098424 | 12/2002 |
| WO | 02100846 | 12/2002 |
| WO | 02100851 | 12/2002 |
| WO | 03/007945 | 1/2003 |
| WO | 03000254 | 1/2003 |
| WO | 03/010140 | 2/2003 |
| WO | 03/010141 | 2/2003 |
| WO | 03014377 | 2/2003 |
| WO | 03/018555 | 3/2003 |
| WO | 03/026587 A2 | 4/2003 |
| WO | 03/040112 | 5/2003 |
| WO | 03101993 | 12/2003 |
| WO | 2004005286 | 1/2004 |
| WO | 2004/064925 | 8/2004 |
| WO | 2004/065367 | 8/2004 |
| WO | 2004087714 | 10/2004 |
| WO | 2005/012288 | 2/2005 |
| WO | 2005014543 | 2/2005 |
| WO | 2005/080388 | 9/2005 |

OTHER PUBLICATIONS

Chemical Abstract for US 6,358,9922: CA2002:213824.
Chemical Abstract for WO 2001/087885: CA2001:851160.
Chemical Abstract for WO 2001/047883L: CA2001:489367.
Chemical Abstract for US 6228868 B1: CA2001:333637.
Chemical Abstract for WO 2000027846 A2: CA2000:335410.
Chemical Abstract for WO 2000026202 A1: CA2000:314687.
Chemical Abstract for WI 2000006556 A1: CA2000:98534.
Chemical Abstract CA1999:645611.
Chemical Abstract for WO 9829408 A1: CA1998:485053.
Chemical Abstract for WO 9808847 A1: CA1998163594.
Translation of Claims only for PCT Application WO 03/00254.
Chemical Abstract CA 384846-70-2.
A.A. Kolykhalov, et al.,"Hepatitis C Virus-Encoded Enzymatic Activities and Conserved RNA Elements in the 3' nontranslated Region are Essential for Virus Replication in Vivo", J. Virology, 2000, 74(4): 2046-2051.
V. Lohmann, et al., "Replication of Subgenomio Hepatitis C Virus RNAs in a Hepatoma Cell Line" Science, 1999, 265: 110-113.
Beaulieu, P. L. et al; "Viral Polymerase Inhibitors"; U.S. Appl. No. 10/198,384, filed Jul. 18, 2002.
Beaulieu, P. L. et al; "Viral Polymerase Inhibitors"; U.S. Appl. No. 10/198,259; filed Jul. 18, 2002.
Hashimoto, et al; "Fused-Ring Compounds And Use Thereof As Drugs"; Pub. No. US 2003/0050320 A1; Mar. 13, 2003.
Hishmat, et al. Bollettino Chimico Farmaoeutico 138 (6) 259-266, 1999.
Arnaiz, et al., WO 9837079; CA 129: 231019, 1998.
Hashimoto, et al., WO 2001047883; CA 135: 76874, 2001.
Chemical Abstract for WO 9632379: CA 1996:746234.
Chemical Abstract CA 1990:234572.
Chemical Abstract CA 1987:458985.
Chemical Abstract 1986:514976.
Chemical Abstract for GB 2118552: CA 1984:85587.
Chemical Abstract for EP73663: CA 1983:505247.
Chemical Abstract for EP50957: CA1982:509865.
Chemical Abstract for DE 2642877: CA1977:453062.
Chemical Abstract: CA1969:68209.
Chemical Abstract: 1968:418961.
Takehide, N. et al; "Benzo-Heterocyclic Derivative"; Patent Abstracts of Japan; Publication No. 09124632A; May 13, 1997.
Chemical Abstract CA 134:340435; Publication No. JP 2001-122855.
Beaulieu, P. L. et al; "Viral Polymerase Inhibitors"; US Patent Application Publication No. US 2002/0065418 A1; May 30, 2002.
Astles, P. C.; "Substituted Azabicyclic Compounds"; US Patent Application Publication No. US 2002/0173527 A2; Nov. 21, 2002.
Hishmat, O. H. et al; "Synthesis of pharmacologically active indoles"; Bollettino Chimico Farmaceutico (1999) 138(6), pp. 259-266; XP002233311.
Fuerstner, A. et al; "Titanium-Induced zipper reactions"; Angewandte Chemle, Int'l Ed. In English (1995), 34(6), pp. 678-681 XP002233857.
Roth, H. J. et al; "Synthesis of indole and carbazole derivatives by condensation of alpha-hydroxyketones and aromatic amines"; Archiv. Der Pharmazle Und Berlchte Der Deutschen Pharmazeutischen Gesellschaft.(1972, 305(3) pp. 159-171 XP002233858.
Youngdale, G. A. et al; "Synthesis and antiinflammatory activity of 5-substituted 2,3-bis(p-methoxyphenyl) indoles"; J. Med. Chem. (1969) 12; pp. 948-949; XP 002233859.
Chemical Abstract: CA 128:275074; JP 10067682.
Chemical Abstract: CA 129:45274; JP 10114654.
CA Abstract, CA 126: 305540, 1997.
CA Abstract, CA 123: 33085, 1995.
Chemical Abstract: CA 134: 340435 for JP 2001-122855.
Chemical Abstract: CA 129: 45274 for JP 10-114654.
Chemical Abstract: CA 128:275074 for JP 10-67682.
Patent Abstract of Japan: Publication No. 09124632 A; May 13, 1997.
Christopher Hulme, et al; The Synthesis and Biological Evaluation of a Novel Series of Indole PDE4 Inhibitors I; Bioorganic & Medicinal Chemistry Letters (1998) vol. 8 pp. 1867-1872.
Pierre L. Beaulieu, et al; Therapies for Hepatitis C Infection: Targeting the Non-Structural Proteins of HCV; Curr. Med. Chem.—Anti-Infective Agents (2002) vol. 1, No. 2 pp. 1-14.
Afdhal, N, O'Brien C, Godofsky E, et al. Valpicitabine (NM283), alone or with PEG-interferon, compared to PEG interferon/ribavirin (PEGIFN/RBV) retreatment in patients with HCV-1 infection and prior non-response to PEBIFN/RBV: One-year results. Presented at the 42nd annual EASL meeting, Apr. 11-15, 2007, Barcelona, Spain.
Ago, H., et al., "Crystal structure of the RNA-dependent RNA polymerase of hepatitis C virus". Structure, 1999, V.7, No. 11, Research Article, pp. 1417-1426.
Amat, Mercedes, et al, "An Efficient Synthesis of 2-(2-Pyridyl)indoles by Palladium (0)-catalyzed heteroarylation", Tetrahedron Letters, vol. 34, No. 31, 1993, p. 5005.
Baba et al.; "A Novel Stereospecific Alkenyl'Alkenyl Cross-Coupling by a Palladium or Nickel-Catalyzed Reaction of Alkenylalanes with Alkenyl Halides" J. Am. Chem. Soc., 1976, 98, 6729-6731.
Bartenschlager, R.,et al., "Nonstructural protein 3 of the hepatitis C virus encodes a serine-type proteinase required for cleavage at the NS3/4 and NS4/5 junctions". Journal of Virology, Jul. 1993, p. 3835-3844.

Beaulieu et al. "Non-nucleoside inhibitors of the hepatitis C virus NS5B polymerase: discovery and preliminary SAR of benzimidazole derivatives." Bioorganic and Medicinal Chemistry Letters, 14 (2004) 119-124.

Behrens, S-E., et al., "Identification and properties of the RNA-dependent RNA polymerase of hepatitis C virus". The EMBO Journal, vol. 15, No. 1, 1996, pp. 12-22.

Bressanelli, S., et al., "Crystal structure of the RNA-dependent RNA polymerase of hepatitis C virus". PNAS, Nov. 1999, Vo. 96, No. 23. pp. 13034-13039.

Bukh, J. et al., "Toward a surrogate model for hepatitis C virus: an infectious molecular clone of the GB virus-B hepatitis agent" Virology, vol. 262, 1999, pp. 470-478.

Carroll, S. S., et al., "Only a small fraction of purified hepatitis C RNA-dependent RNA polymerase is catalytically compentent: implications for viral replication and in vitro assays". Biochemistry, 2000, 39, pp. 8243-8249.

CAS Registry No. 115577-24-7 Registry Copyright 2001 ACS.
CAS Registry No. 214150-90-0 Registry Copyright 2001 ACS.
CAS Registry No. 214150-93-3 Registry Copyright 2001 ACS.
CAS Registry No. 66315-47-7 Registry Copyright 2001 ACS.
CAS Registry No. 66315-51-3 Registry Copyright 2001 ACS.
CAS Registry No. 66315-52-4 Registry Copyright 2001 ACS.
Cas Registry No. 66630-73-7 Registry Copyright 2001 ACS.

Danieli, B. et al. "Application of the PD-catalyzed hetroarylation to the synthesis of 5-(indol2'-yl)pyridin-2-one and 5-(indol-2'yl) pyran-2-one" Tetrahedron, vol. 54, No. 46, 1998, p. 14081.

DeFrancesco, R., et al., "RNA-dependent RNA polymerase of hepatitis C virus". Methods in Enzymology, vol. 275, 1998, pp. 58-67.

Deutsch, M. et al; "Old and emerging therapies in chronic hepatitis C: an update;" 2008, J. of Viral Hepatitis, 15, p. 2-11.

Erhardt et al, "Safety, Pharmacokinetics and Antiviral effects of Boehringer Ingelheim BILB 1941, a Novel HCV RNA Polymerase, After 5 days Oral treatment in Patients with Chronic Hepatitis C", Poster from EASL 42nd Mtg. of Euruopean Association for the Study of Liver Diseases, Barcelona, Spain Apr. 11-15, 2007.

Ferrari, E., et al., "Characterization of soluble hepatitis C virus RNA-dependent RNA polymerase expressed in *Escherichia coli*". Journal of Virology, 1990, vol. 73, No. 2., pp. 1649-1654.

Gale, M.J.et al., "Evidence that hepatitis C virus resistance to interferon is mediated through repression of the PKR protein kinase by the nonstructural 5A protein". Virology, 230, 1997, Article No. VY978493, pp. 217-227.

Grakoui, A., et al., "A second hepatitis C virus-encoded proteinase". Proc. Natl. Acad. Sci, USA, vol. 90, Nov. 1993, Biochemistry, pp. 10583-10587.

Grakoui, A., et al., "Expression and identification of hepatitis C virus polyprotein cleavage products". Journal of Virology, 193, vol. 67, No. 3, pp. 1385-1395.

Hijkata, M., et al., "Gene mapping of the putative structural region of the hepatitis C virus genome by in vitro processing analysis". Proc. Natl. Acad. Sci. USA, vol. 88, Jul. 1991, Biochemistry, pp. 5547-5551.

Hijkata, M., et al., "Two distinct proteinase activities required for the processing of a putative nonstructural precursor protein of hepatitis C virus". Journal of Virology, Aug. 1993, Vo. 67, No. 8, pp. 4665-4675.

Hoofnagle, J.H.; 1997; Hepatology 26: 15S-20S.

Ishiyama, T., Murata, M., Miyaura, N.; "Palladium(0)-Catalyzed Cross-Coupling Reaction of Alkoxydiboron with Haloarenes: A Direct Procedure for Arylboronic Esters;" J. Org. Chem. 1995, 60, 7508.

Kim, D. W., al., "C-terminal domain of the hepatitis C virus NS3 protein contains an RNA helicase activity". Biochemical & Biophysical Research Communications, vol. 215, No. 1, 1995, pp. 160-166.

Kim, J.E., et al., "Subcellular localization of hepatitis C viral proteins in mammalian cells". Arch Virol., 1999, 144, pp. 329.343.

Kwong, A. D., et al., "Hepatitis C virus NS3/4A protease". Antiviral Research, 40, 1998, pp. 1-18.

Lauer, G. and Walker, B., "Hepatitis C Virus Infection," N. Engl. J. Med., vol. 345(1), pp. 41-52 (Jul. 2001), at p. 46, col. 1, lines 23-25.

Lemon, S.H.; Honda, M.; "Internal Ribosome Entry Sites within the RNA Genomes of Hepatitis C Virus and Other Flaviviruses;" 1997; Semin. Virol. 8: 274-288.

Lesburg, C.A., et al., "Crystal structure of the RNA-dependent RNA polymerase from hepatitis C virus reveals a fully encircled active site". Nature Sructural Biology, vol. 6, No. 10, 1999, p. 937-943.

Levin, Jules, "Safety, Pharmacokinetics and Antiviral effects of Boehringer Ingelheim BILB 1941, a Novel HCV RNA Polymerase, After 5 days Oral treatment in Patients with Chronic Hepatitis C", www.natap.org/2007/EASL/EASL_48.htm EASL 42nd Mtg. of Euruopean Association for the Study of Liver Diseases, Barcelona, Spain Apr. 11-15, 2007.

Lindsay, K.L.; "Therapy of Hepatitis C: Overview;" 1997; Hepatology 26: 71S-77S.

Lohmann, V., et al., "Biochemical and kinetic analyses of NS5B RNA-dependent RNA polymerase of the hepatitis C virus". Virology, Article No. VY989311, Vo. 249, 1998, pp. 108-118.

Lohmann, V., et al., "Biochemical Properties of hepatitis C virus NS5B RNA-dependent RNA polymerase and identification of amino acid sequence motifs essential for enzymatic activity". Journal of Virology, Nov. 1997, Vo. 71, No. 11, pp. 8416-8428.

Love, R. A., et al., "The crystal structure of hepatitis C virus NS3 proteinase reveals a trypsin-like fold and a structural zinc binding site". Cell, vol. 87, 1996, pp. 331-342.

Luo, G., et al., "DeNovo initiation of RNA synthesis by the RNA-dependent RNA polymerase (NS5B) of hepatitis C virus". Journal of Virology, Jan. 2000, vol. 74, No. 2, pp. 851-863.

Mayer et al, "Solid-Phase Synthesis of Benzimidazoles"; Tetrahedron Letters 39 (1998) 6655-6658.

McKercher, G., et al., "Specific inhibitors of HCV polymerase identified using an NS5B with lower affinity for template/primer substrate". Nucleic Acids Research, 2004, vol. 32, No. 2, pp. 422-431.

Merlic, C.A. et al. "Benzannulation reactions of Fischer carbene compleses for the synthesis of indolocarbozoles" TETRAHEDRON, vol. 57, No. 24, p. 5199-5212, 2001.

Miller, J.A. et al, "Preparation of Unsymmetrical Biaryls via Ni-or Pd-Catalyzed Coupling of Aryl chlorides with Arylzincs". Tetrahdron Letters, vol. 39 (36), 1998, pp. 6441-6444.

Minato, Akio et al, "Palladium-Phosphine Complex Catalyzed Cross-Coupling Reaction of 1-Methyl-2-pyrrolyl-magnesium Bromide and -zinc chloride with organic halides" Tetrahedron Letters, vol. 22, No. 52, 1981 p. 5319.

Miyaura, N. et al. "Palladium Catalyzed Cross-Coupling Reactions of Organoboron Compounds", Chem. Rev. 1995, vol. 95, pp. 2457-2483.

Murata, M.; Oyama, T.; Watanabe, S., Masuda, Y. "Palladium-Catalyzed Borylation of Aryl Halides or Triflates with Dialkoxyborne: A Novel and Facile Synthetic Route to Arylboronates;" J. Org. Chem. 2000, 65, 164.

Negishi, S. Baba, "Novel Stereoselective Alkenyl-Aryl Coupling via Nickel-catalysed Reaction of Alkenylalanes with Aryl Halides;" J. Chem. Soc. Chem. Communications, 1976, 596-597.

Oh, J-W, et al., "A recombinant hepatitis C virus RNA-dependent RNA polymerase capable of copying the full-length viral RNA". Journal of Virology, Sep. 1999, Vo. 73, No. 9, pp. 7694-7702.

Perandones, F. et al; Synthesis of imidazol[4,5-b]pyridines from aminoimidazolecarbaldehydes, J. heterocyc. Chem. vol. 34, pp. 107-112, 1997.

Qin, W. et al., "Mutational analysis of the structure and function of hepatitis C virus RNA-dependent RNA polymerase". American Assoc. for the Study of Liver Diseases. Hepatology, vol. 33, No. 3, 2001, pp. 728,737.

Reed, K.E., et al., "Phosphorylation of the hepatitis C virus NS5A protein in vitro and in vivo: properties of the NS5A-associated kinase". Journal of Virology, Oct. 1997, vol. 71, No. 10, pp. 7187-7197.

Reed, K.E.; Rice, C.M.; "Overview of Hepatitis C Virus Genome Structure, Polyprotein Processing, and Protein Properties;" 1999; Curr. Top. Microbiol. Immunol. 242: pp. 55-84.

Reichard, O. et al., "Therapy of Hepatitis C: Alpha Interferon and Ribavirin;" 1997 Hepatology 26; pp. 108S-111S.

Rice, C.M.; 1996; "Flavivindae: the viruses and their replication"; pp. 931-960 in Fields Virology; Fields, B.N.; Knipe, D.M.; Howley, P.M. (eds.); Lippincott-Raven Publishers, Philadelphia, PA.

Rorrer, L.C. et al. "Convenient New Route to Tetradentate and Pentadentate Macrocyclic Tetraamide Ligands", Organic Letters, 1999, vol. 1, No. 8, pp. 1157-1159.

Sakamoto, T., et al, "Indolylzinc Iodides by Oxidative addition of activ zinc to Iodoindoles" Tetrahedron Letters, vol. 34, No. 37, 1993, p. 5955.

Sarisky, R.T. "Non-nucleoside inhibitors of the HCV polymerase". Journal of Antimicrobial Chemotherapy, 2004, 54, pp. 14-16.

Sarrazin, C., et al., "SCH 503034, a Novel hepatitis C virus protease inhibitor, plus pegylated inteferon a-2b for genotype 1 nonresponders". Gastroenterolgy, 2007, 132, pp. 1270-1278.

Simons, J. N., et al., "Identification of two flavivirus-like genomes in the GB hepatitis agent". Proc. Natl, Acad. Sci, Medical Sciences, Vo. 92, Apr. 1995, pp. 3401-3405.

Stanforth, S.P. "Catalytic Cross-coupling Reactions in Biaryl Synthesis" Tetrahedron, vol. 54(3-4), 1998, pp. 263-303.

Sun, X-L., et al., "De Novo RNA synthesis catalyzed by HCV RNA dependent RNA polymerase". Biochemical and Biophysical Research Communications, vol. 268, 2000, pp. 798-803.

Tomei, L., et al., "Biochemical characterization of a hepatitis C virus RNA-dependent RNA polymerse mutant lacking the C-terminal hydrophobic sequence". Journal of General Virology, 2000, 81, pp. 759,767.

Watanabe, T. et al, "Synthesis of sterically hindered blaryis via the palladium-catalyzed cross-coupling reaction of aryliboronic acids of their esters with haloarenes" SYNLETT, vol. 3, p. 207-210, 1992.

Wu et al; "One-pot' nitro reduction-cyclisation solid phase route to benzimidazoles"; Tetrahedron Letters 41 (2000) 9871-9874.

Yamashita, T., et al., "RNA-dependent RNA polymerase activity of the soluble recombinant hepatitis C virus NS5B protein truncated at the C-terminal region". The Journal of Biological Chemistry, vol. 273, No. 25, Jun. 1999, pp. 15479-15486.

Yanagi, M., et al., "Transcripts from a single full-length cDNA clone of hepatitis C virus are infectious when directly transfected into the liver of a chimpanzee.". PNAS, Vo. 94, Aug. 1997, pp. 8738-8743.

Yuan, Z-H, et al., "Expression, purfication, and partial characterization of HCV RNA polymerase". Biochemical and Biophysical Research Communications, vol. 232, 1997, pp. 231-235.

Zhang, H-C., et al: "Efficient synthesis of 3-substituted 2-arylindoles via Suzuki coupling reactions in the solid phase"; Tetrahedron Letters, 42, 2001, pp. 4751-4754.

Zhang, J-H, et al., "A simple statistical parameter for use in evaluation and validation of high throughput screening assays". Journal of Biomolecular Screening, vol. 4, Nov. 1999, pp. 67-73.

Zhong, W., et al., "De Novo initiation of RNA synthesis by hepatitis C virus nonstructural protein 5B polymerase". Journal of Virology, Feb. 2000, Vo. 74, No. 4, pp. 2017-2022.

Zhong, W., et al., "Template/primer requirements and single nucleotide incorporation by hepatitis C virus nonstructural protein 5B polymerase". Journal of Virology, Oct. 2000, vol. 74, No. 19, pp. 9134-9143.

* cited by examiner

SEQUENCE LISTING

<160> NUMBER OF SEQ ID NOS: 4

<210> SEQ ID NO 1
<211> LENGTH: 621
<212> TYPE: PRT
<213> ORGANISM: HCV NS5B

<400> SEQUENCE: 1

```
Met Ser Tyr Tyr His His His His His His Asp Tyr Asp Ile Pro Thr
 1               5                  10                  15

Thr Glu Asn Leu Tyr Phe Gln Gly Ala Met Asp Pro Glu Phe Ser Met
            20                  25                  30

Ser Tyr Thr Trp Thr Gly Ala Leu Ile Thr Pro Cys Ala Ala Glu Glu
        35                  40                  45

Ser Gln Leu Pro Ile Asn Ala Leu Ser Asn Ser Leu Val Arg His Arg
    50                  55                  60

Asn Met Val Tyr Ser Thr Thr Ser Arg Ser Ala Ala Leu Arg Gln Lys
65                  70                  75                  80

Lys Val Thr Phe Asp Arg Leu Gln Val Leu Asp Asp His Tyr Arg Asp
                85                  90                  95

Val Leu Lys Glu Met Lys Ala Lys Ala Ser Thr Val Lys Ala Lys Leu
            100                 105                 110

Leu Ser Val Glu Glu Ala Cys Lys Leu Thr Pro Pro His Ser Ala Lys
        115                 120                 125

Ser Lys Phe Gly Tyr Gly Ala Lys Asp Val Arg Asn Leu Ser Ser Lys
    130                 135                 140

Ala Val Asp His Ile Arg Ser Val Trp Lys Asp Leu Leu Glu Asp Thr
145                 150                 155                 160

Glu Thr Pro Ile Asp Thr Thr Ile Met Ala Lys Asn Glu Val Phe Cys
                165                 170                 175

Val Gln Pro Glu Lys Gly Gly Arg Lys Pro Ala Arg Leu Ile Val Phe
            180                 185                 190

Pro Asp Leu Gly Val Arg Val Cys Glu Lys Met Ala Leu Tyr Asp Val
        195                 200                 205

Val Ser Thr Leu Pro Gln Ala Val Met Gly Ser Ser Tyr Gly Phe Gln
    210                 215                 220

Tyr Ser Pro Lys Gln Arg Val Glu Phe Leu Val Asn Ala Trp Lys Ser
225                 230                 235                 240

Lys Lys Cys Pro Met Gly Phe Ser Tyr Asp Thr Arg Cys Phe Asp Ser
                245                 250                 255

Thr Val Thr Glu Ser Asp Ile Arg Val Glu Glu Ser Ile Tyr Gln Cys
            260                 265                 270

Cys Asp Leu Ala Pro Glu Ala Arg Gln Ala Ile Lys Ser Leu Thr Glu
        275                 280                 285

Arg Leu Tyr Ile Gly Gly Pro Leu Thr Asn Ser Lys Gly Gln Asn Cys
    290                 295                 300

Gly Tyr Arg Arg Cys Arg Ala Ser Gly Val Leu Thr Thr Ser Cys Gly
305                 310                 315                 320

Asn Thr Leu Thr Cys Tyr Leu Lys Ala Ser Ala Ala Cys Arg Ala Ala
                325                 330                 335

Lys Leu Gln Asp Cys Thr Met Leu Val Asn Gly Asp Asp Leu Val Val
            340                 345                 350

Ile Cys Glu Ser Ala Gly Thr Gln Glu Asp Ala Ala Asn Leu Arg Val
```

```
                355                 360                 365
Phe Thr Glu Ala Met Thr Arg Tyr Ser Ala Pro Pro Gly Asp Leu Pro
370                 375                 380

Gln Pro Glu Tyr Asp Leu Glu Leu Ile Thr Ser Cys Ser Ser Asn Val
385                 390                 395                 400

Ser Val Ala His Asp Ala Ser Gly Lys Arg Val Tyr Tyr Leu Thr Arg
                405                 410                 415

Asp Pro Thr Thr Pro Leu Ala Arg Ala Ala Trp Glu Thr Ala Arg His
            420                 425                 430

Thr Pro Ile Asn Ser Trp Leu Gly Asn Ile Ile Met Tyr Ala Pro Thr
            435                 440                 445

Leu Trp Ala Arg Met Val Leu Met Thr His Phe Phe Ser Ile Leu Leu
450                 455                 460

Ala Gln Glu Gln Leu Glu Lys Ala Leu Asp Cys Gln Ile Tyr Gly Ala
465                 470                 475                 480

Cys Tyr Ser Ile Glu Pro Leu Asp Leu Pro Gln Ile Ile Glu Arg Leu
                485                 490                 495

His Gly Leu Ser Ala Phe Ser Leu His Ser Tyr Ser Pro Gly Glu Ile
            500                 505                 510

Asn Arg Val Ala Ser Cys Leu Arg Lys Leu Gly Val Pro Pro Leu Arg
            515                 520                 525

Val Trp Arg His Arg Ala Arg Ser Val Arg Ala Lys Leu Leu Ser Gln
530                 535                 540

Gly Gly Arg Ala Ala Thr Cys Gly Lys Tyr Leu Phe Asn Trp Ala Val
545                 550                 555                 560

Arg Thr Lys Leu Lys Leu Thr Pro Ile Pro Ala Ala Ser Arg Leu Asp
                565                 570                 575

Leu Ser Gly Trp Phe Val Ala Gly Tyr Asn Gly Gly Asp Ile Tyr His
            580                 585                 590

Ser Leu Ser Arg Ala Arg Pro Arg Trp Phe Met Leu Cys Leu Leu Leu
            595                 600                 605

Leu Ser Val Gly Val Gly Ile Tyr Leu Leu Pro Asn Arg
610                 615                 620

<210> SEQ ID NO 2
<211> LENGTH: 30
<212> TYPE: DNA
<213> ORGANISM: Artificial Sequence
<220> FEATURE:
<223> OTHER INFORMATION: Forward Primer

<400> SEQUENCE: 2
acgcagaaag cgtctagcca tggcgttagt                                       30

<210> SEQ ID NO 3
<211> LENGTH: 30
<212> TYPE: DNA
<213> ORGANISM: Artificial Sequence
<220> FEATURE:
<223> OTHER INFORMATION: Reverse Primer

<400> SEQUENCE: 3
tcccggggca ctcgcaagca ccctatcagg                                       30

<210> SEQ ID NO 4
<211> LENGTH: 26
<212> TYPE: DNA
<213> ORGANISM: Artificial Sequence
```

```
<220> FEATURE:
<223> OTHER INFORMATION: PUTR probe

<400> SEQUENCE: 4
tggtctgcgg aaccggtgag tacacc                                  26
```

VIRAL POLYMERASE INHIBITORS

RELATED APPLICATIONS

This Application is a Divisional application of U.S. Ser. No. 10/198,680, filed Jul. 18, 2002, for which benefit of U.S. Provisional application Ser. No. 60/307,674 filed on Jul. 25, 2001, and U.S. Provisional application Ser. No. 60/338,061 filed on Dec. 7, 2001 is hereby claimed. These Provisional Applications are herein incorporated by reference in their entirety.

TECHNICAL FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051*). HCV is not easily cleared by the hosts' immunological defences; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S*). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection. Prolonged treatment of chronically infected patients with interferon or interferon and ribavirin is the only currently approved therapy, but it achieves a sustained response in fewer than 50% of cases (Lindsay, K. L.; 1997; *Hepatology* 26: 71S-77S*, and Reichard, O.; Schvarcz, R.; Weiland, O.; 1997 *Hepatology* 26: 108S-111S*).

* incorporated herein by reference

HCV belongs to the family Flaviviridae, genus hepacivirus, which comprises three genera of small enveloped positive-strand RNA viruses (Rice, C. M.; 1996; "Flaviviridae: the viruses and their replication"; pp. 931-960 in *Fields Virology*; Fields, B. N.; Knipe, D. M.; Howley, P. M. (eds.); Lippincott-Raven Publishers, Philadelphia Pa.*). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274-288*). The HCV polyprotein is cleaved co- and post-translationally into at least 10 individual polypeptides (Reed, K. E.; Rice, C. M.; 1999; *Curr. Top. Microbiol. Immunol.* 242: 55-84*). The structural proteins result from signal peptidases in the N-terminal portion of the polyprotein. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22*; and Lohmann, V.; Körner, F.; Herian, U.; Bartenschlager, R.; 1997; *J. Virol.* 71: 8416-8428*). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051*).

* incorporated herein by reference

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 00/06529 reports inhibitors of NS5B which are α,γ-diketoacids.

WO 00/13708, WO 00/10573, WO 00/18231, and WO 01/47883 report inhibitors of NS5B proposed for treatment of HCV.

SUMMARY OF THE INVENTION

It is therefore an object of the invention to provide a novel series of compounds having improved inhibitory activity against HCV polymerase.

In a first aspect of the invention, there is provided an isomer, enantiomer, diastereoisomer, or tautomer of a compound, represented by formula I:

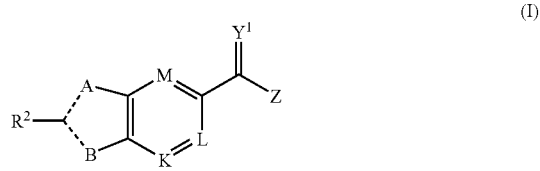

(I)

wherein:

A is O, S, NR$^1$, or CR$^1$, wherein R$^1$ is selected from the group consisting of: H, (C$_{1-6}$)alkyl optionally substituted with:
  halogen, OR$^{11}$, SR$^{11}$ or N(R$^{12}$)$_2$, wherein R$^{11}$ and each R$^{12}$ is independently H, (C$_{1-6}$)alkyl, (C$_{3-7}$)cycloalkyl, (C$_{1-6}$)alkyl-(C$_{3-7}$)cycloalkyl, (C$_{1-6}$)alkyl-aryl or (C$_{1-6}$)alkyl-Het, said aryl or Het optionally substituted with R$^{10}$; or
  both R$^{12}$ are covalently bonded together and to the nitrogen to which they are both attached to form a 5, 6 or 7-membered saturated heterocycle;

— represents either a single or a double bond;

R$^2$ is selected from: H, halogen, R$^{21}$, OR$^{21}$, SR$^{21}$, COOR$^{21}$, SO$_2$N(R$^{22}$)$_2$, N(R$^{22}$)$_2$, CON(R$^{22}$)$_2$, NR$^{22}$C(O)R$^{22}$ or NR$^{22}$C(O)NR$^{22}$ wherein R$^{21}$ and each R$^{22}$ is independently H, (C$_{1-6}$)alkyl, haloalkyl, (C$_{2-6}$)alkenyl, (C$_{3-7}$)cycloalkyl, (C$_{2-6}$)alkynyl, (C$_{5-7}$)cycloalkenyl, 6 or 10-membered aryl or Het, said R$^{21}$ and R$^{22}$ being optionally substituted with R$^{20}$, or both R$^{22}$ are bonded together to form a 5, 6 or 7-membered saturated heterocycle with the nitrogen to which they are attached; wherein $R^{10}$ and $R^{20}$ is each:

1 to 4 substituents selected from: halogen, $OPO_3H$, $NO_2$, cyano, azido, $C(=NH)NH_2$, $C(=NH)NH(C_{1-6}alkyl)$ or $C(=NH)NHCO(C_{1-6}alkyl)$; or 1 to 4 substituents selected from:

a) $(C_{1-6})$ alkyl or haloalkyl, $(C_{3-7})$cycloalkyl, $C_{3-7}$ spirocycloalkyl optionally containing 1 or 2 heteroatom, $(C_{2-6})$alkenyl, $(C_{3-6})$cycloalkenyl, $(C_{2-8})$alkynyl, $(C_{1-6})$ alkyl-$(C_{3-7})$cycloalkyl, all of which optionally substituted with $R^{150}$;

b) $OR^{104}$ wherein $R^{104}$ is H, $(C_{1-6}alkyl)$, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, said alkyl, cycloalkyl, aryl, Het, $(C_{1-6}alkyl)$aryl or $(C_{1-6}alkyl)$Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}alkyl)$aryl or $(C_{1-6}alkyl)$Het, said alkyl, cycloalkyl, aryl, Het, $(C_{1-6}alkyl)$aryl or $(C_{1-6}alkyl)$Het being optionally substituted with $R^{150}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl or $(C_{1-6}alkyl)$Het or both $R^{108}$ are covalently bonded together and to the nitrogen to which they are attached to form a 5, 6 or 7-membered saturated heterocycle, said alkyl, cycloalkyl, aryl, Het, $(C_{1-6}alkyl)$aryl or $(C_{1-6}alkyl)$Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl or $(C_{1-6}alkyl)$Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl, $(C_{1-6}alkyl)$Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}alkyl)$aryl or $(C_{1-6}alkyl)$Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}alkyl)$aryl or $(C_{1-6}alkyl)$Het, said $(C_{1-6})$alkyl, $(C_{3-7})$cycloalkyl, $(C_{1-6})$alkyl-$(C_{3-7})$cycloalkyl, aryl, Het, $(C_{1-6}alkyl)$aryl or $(C_{1-6}alkyl)$Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}alkyl)$aryl or $(C_{1-6}alkyl)$Het, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle;

said alkyl, cycloalkyl, $(C_{1-6})$alkyl-$(C_{3-7})$cycloalkyl, aryl, Het, $(C_{1-6}alkyl)$aryl or $(C_{1-6}alkyl)$Het or heterocycle being optionally substituted with $R^{150}$;

h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}alkyl)$aryl or $(C_{1-6}alkyl)$Het, said alkyl, cycloalkyl, alkyl-cycloalkyl, aryl, Het, $(C_{1-6}alkyl)$aryl or $(C_{1-6}alkyl)$Het being optionally substituted with $R^{150}$; or $R^{122}$ is $OR^{123}$ or $N(R^{124})_2$ wherein $R^{123}$ and each $R^{124}$ is independently H $(C_{1-6}alkyl)$, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, or $R^{124}$ is OH or $O(C_{1-6}alkyl)$ or both $R^{124}$ are covalently bonded together to form a 5, 6 or 7-membered saturated heterocycle, said alkyl, cycloalkyl, alkyl-cycloalkyl, aryl, Het, $(C_{1-6}alkyl)$aryl or $(C_{1-6}alkyl)$Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl or $(C_{1-6}alkyl)$Het, said alkyl, cycloalkyl, aryl, Het, $(C_{1-6}alkyl)$aryl or $(C_{1-6}alkyl)$Het being optionally substituted with $R^{150}$;

j) $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, said $(C_{1-6})$alkyl, $(C_{3-7})$cycloalkyl, or $(C_{1-6})$alkyl-$(C_{3-7})$cycloalkyl, aryl, Het, $(C_{1-6}alkyl)$aryl and $(C_{1-6}alkyl)$Het being optionally substituted with $R^{150}$;

k) $CONR^{129}R^{130}$ wherein $R^{129}$ and $R^{130}$ are independently H, $(C_{1-6})$alkyl $(C_{3-7})$cycloalkyl, $(C_{1-6})$alkyl-$(C_{3-7})$cycloalkyl, aryl, Het, $(C_{1-6}alkyl)$aryl or $(C_{1-6}alkyl)$Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}alkyl)$aryl, $(C_{1-6}alkyl)$Het and heterocycle being optionally substituted with $R^{150}$;

l) aryl, Het, $(C_{1-6}alkyl)$aryl or $(C_{1-6}alkyl)$Het, all of which being optionally substituted with $R^{150}$; and wherein $R^{150}$ is defined as:

1 to 3 substituents selected from: halogen, $OPO_3H$, $NO_2$, cyano, azido, $C(=NH)NH_2$, $C(=NH)NH(C_{1-6}alkyl)$ or $C(=NH)NHCO(C_{1-6}alkyl)$; or 1 to 3 substituents selected from:

a) $(C_{1-6})$ alkyl or haloalkyl, $(C_{3-7})$cycloalkyl, $C_{3-7}$ spirocycloalkyl optionally containing 1 or 2 heteroatom, $(C_{2-6})$alkenyl, $(C_{2-8})$alkynyl, $(C_{1-6})$ alkyl-$(C_{3-7})$cycloalkyl, all of which optionally substituted with $R^{160}$;

b) $OR^{104}$ wherein $R^{104}$ is H, $(C_{1-6}alkyl)$, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, said alkyl, cycloalkyl, aryl, Het, $(C_{1-6}alkyl)$aryl or $(C_{1-6}alkyl)$Het being optionally substituted with $R^{160}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6}alkyl)$aryl or $(C_{1-6}alkyl)$Het, said alkyl, cycloalkyl, aryl, Het, $(C_{1-6}alkyl)$aryl or $(C_{1-6}alkyl)$Het being optionally substituted with $R^{160}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl or $(C_{1-6}alkyl)$Het or both $R^{108}$ are covalently bonded together and to the nitrogen to which they are attached to form a 5, 6 or 7-membered saturated heterocycle, said alkyl, cycloalkyl, aryl, Het, $(C_{1-6}alkyl)$aryl or $(C_{1-6}alkyl)$Het or heterocycle being optionally substituted with $R^{160}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl or $(C_{1-6}alkyl)$Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}alkyl)$aryl, $(C_{1-6}alkyl)$Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}alkyl)$aryl or $(C_{1-6}alkyl)$Het, or both $R^{111}$ and $R^{112}$ are covalently bonded together and to the nitrogen to which they are attached to form a 5, 6 or 7-membered saturated heterocycle, said alkyl, cycloalkyl, aryl, Het, ($C_{1-6}$alkyl)aryl or ($C_{1-6}$alkyl)Het, or heterocycle being optionally substituted with $R^{160}$;

f) $NR^{116}COR^{117}$ wherein $R^{116}$ and $R^{117}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het being optionally substituted with $R^{160}$;

g) $NR^{118}CONR^{119}R^{120}$ wherein $R^{118}$, $R^{119}$ and $R^{120}$ is each H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle;

said alkyl, cycloalkyl, ($C_{1-6}$)alkyl-($C_{3-7}$)cycloalkyl, aryl, Het, ($C_{1-6}$alkyl)aryl or ($C_{1-6}$alkyl)Het or heterocycle being optionally substituted with $R^{160}$;

h) $NR^{121}COCOR^{122}$ wherein $R^{121}$ and $R^{122}$ is each H, ($C_{1-6}$)alkyl, ($C_{3-7}$)cycloalkyl, ($C_{1-6}$)alkyl-($C_{3-7}$)cycloalkyl, a 6- or 10-membered aryl, Het, ($C_{1-6}$alkyl)aryl or ($C_{1-6}$alkyl)Het, said alkyl, cycloalkyl, alkyl-cycloalkyl, aryl, Het, ($C_{1-6}$alkyl)aryl or ($C_{1-6}$alkyl)Het being optionally substituted with $R^{160}$;

or $R^{122}$ is $OR^{123}$ or $N(R^{124})_2$ wherein $R^{123}$ and each $R^{124}$ is independently H, ($C_{1-6}$alkyl), ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, or $R^{124}$ is OH or O($C_{1-6}$alkyl) or both $R^{124}$ are covalently bonded to form a 5, 6 or 7-membered saturated heterocycle, said alkyl, cycloalkyl, alkyl-cycloalkyl, aryl, Het, ($C_{1-6}$alkyl)aryl or ($C_{1-6}$alkyl)Het and heterocycle being optionally substituted with $R^{160}$;

i) $COR^{127}$ wherein $R^{127}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$alkyl)aryl or ($C_{1-6}$alkyl)Het, said alkyl, cycloalkyl, aryl, Het, ($C_{1-6}$alkyl)aryl or ($C_{1-6}$alkyl)Het being optionally substituted with $R^{160}$;

j) tetrazole, $COOR^{128}$ wherein $R^{128}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl or ($C_{1-6}$alkyl)Het, said ($C_{1-6}$)alkyl, ($C_{3-7}$)cycloalkyl, or ($C_{1-6}$)alkyl-($C_{3-7}$)cycloalkyl, aryl, Het, ($C_{1-6}$alkyl)aryl and ($C_{1-6}$alkyl)Het being optionally substituted with $R^{160}$; and k) $CONR^{129}R^{130}$ wherein $R^{129}$ and $R^{130}$ are independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$alkyl)aryl or ($C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, ($C_{1-6}$alkyl)aryl, ($C_{1-6}$alkyl)Het and heterocycle being optionally substituted with $R^{160}$;

wherein $R^{160}$ is defined as 1 or 2 substituents selected from: tetrazole, halogen, CN, $C_{1-6}$alkyl, haloalkyl, $COOR^{161}$, $SO_3H$, $SR^{161}$, $SO_2R^{161}$, $OR^{161}$, $N(R^{162})_2$, $SO_2N(R^{162})_2$, $NR^{162}COR^{162}$ or $CON(R^{162})_2$ wherein $R^{161}$ and each $R^{162}$ is independently H, ($C_{1-6}$)alkyl, ($C_{3-7}$)cycloalkyl or ($C_{1-6}$)alkyl-($C_{3-7}$)cycloalkyl; or both $R^{162}$ are covalently bonded together and to the nitrogen to which they are attached to form a 5, 6 or 7-membered saturated heterocycle, B is $NR^3$ or $CR^3$ with the proviso that one of A or B is either $CR^1$ or $CR^3$, wherein $R^3$ is selected from ($C_{1-6}$)alkyl, haloalkyl, ($C_{3-7}$)cycloalkyl, ($C_{5-7}$)cycloalkenyl, ($C_{6-10}$)bicycloalkyl, ($C_{6-10}$)bicycloalkenyl, 6- or 10-membered aryl, Het, ($C_{1-6}$)alkyl-aryl or ($C_{1-6}$)alkyl-Het, said alkyl, cycloalkyl, bicycloalkyl, aryl, Het, alkyl-aryl and alkyl-Het being optionally substituted with from 1 to 4 substituents selected from: halogen, or a) ($C_{1-6}$)alkyl optionally substituted with:
$OR^{31}$ or $SR^{31}$ wherein $R^{31}$ is H, ($C_{1-6}$alkyl), ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or
$N(R^{32})_2$ wherein each $R^{32}$ is independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or both $R^{32}$ are covalently bonded together and to the nitrogen to which they are attached to form a 5, 6 or 7-membered saturated heterocycle;

b) $OR^{33}$ wherein $R^{33}$ is H, ($C_{1-6}$)alkyl, ($C_{3-7}$)cycloalkyl or ($C_{1-6}$)alkyl-($C_{3-7}$)cycloalkyl, aryl, Het, ($C_{1-6}$)alkyl-aryl or ($C_{1-6}$)alkyl-Het;

c) $SR^{34}$ wherein $R^{34}$ is H, ($C_{1-6}$)alkyl, ($C_{3-7}$)cycloalkyl, or ($C_{1-6}$)alkyl-($C_{3-7}$)cycloalkyl, aryl, Het, ($C_{1-6}$)alkyl-aryl or ($C_{1-6}$)alkyl-Het; and d) $N(R^{35})_2$ wherein each $R^{35}$ is independently H, ($C_{1-6}$)alkyl, ($C_{3-7}$)cycloalkyl, ($C_{1-6}$)alkyl-($C_{3-7}$)cycloalkyl, aryl, Het, ($C_{1-6}$)alkyl-aryl or ($C_{1-6}$)alkyl-Het; or both $R^{35}$ are covalently bonded together and to the nitrogen to which they are attached to form a 5, 6 or 7-membered saturated heterocycle;

K is N or $CR^4$, wherein $R^4$ is H, halogen, ($C_{1-6}$)alkyl, haloalkyl, ($C_{3-7}$)cycloalkyl or ($C_{1-6}$)alkyl-($C_{3-7}$)cycloalkyl; or $R^4$ is $OR^{41}$ or $SR^{41}$, $COR^{41}$ or $NR^{41}COR^{41}$ wherein each $R^{41}$ is independently H, ($C_{1-6}$)alkyl), ($C_{3-7}$)cycloalkyl or ($C_{1-6}$)alkyl-($C_{3-7}$)cycloalkyl;

or $R^4$ is $NR^{42}R^{43}$ wherein $R^{42}$ and $R^{43}$ are each independently H, ($C_{1-6}$)alkyl, ($C_{3-7}$)cycloalkyl, ($C_{1-6}$)alkyl-($C_{3-7}$)cycloalkyl, or both $R^{42}$ and $R^{43}$ are covalently bonded together and to the nitrogen to which they are attached to form a 5, 6 or 7-membered saturated heterocycle;

L is N or $CR^5$, wherein $R^5$ has the same definition as $R^4$ defined above;

M is N or $CR^7$, wherein $R^7$ has the same definition as $R^4$ defined above;

$Y^1$ is O or S;

Z is $OR^6$, wherein $R^6$ is H, ($C_{1-6}$)alkyl being optionally substituted with: halo, hydroxy, carboxy, amino, $C_{1-6}$ alkoxy, $C_{1-6}$alkoxycarbonyl, and $C_{1-6}$ alkylamino; or $R^6$ is $C_{1-6}$ alkylaryl optionally substituted with: halogen, cyano, nitro, $C_{1-6}$ alkyl, $C_{1-6}$haloalkyl, $C_{1-6}$alkanoyl, $-(CH_2)_{1-6}-COOR^7$, $-(CH_2)_{1-6}-CONR^7R^8$, $-(CH_2)_{1-6}-NR^7R^8$, $-(CH_2)_{1-6}-NR^7COR^8$, $-(CH_2)_{1-6}-NHSO_2R^7$, $-(CH_2)_{1-6}-OR^7$, $-(CH_2)_{1-6}-SR^7$, $-(CH_2)_{1-6}-SO_2R^7$, and $-(CH_2)_{1-6}-SO_2NR^7R^8$, wherein each $R^7$ and each $R^8$ is H or $C_{1-6}$ alkyl, or Z is $NR^9R^{10}$ wherein each of $R^9$ and $R^{10}$ is selected from: H, $C_{1-6}$alkoxy, or $C_{1-6}$alkyl optionally substituted with halo, hydroxy, carboxy, amino, $C_{1-6}$ alkoxy, $C_{1-6}$alkoxycarbonyl, and $C_{1-6}$ alkylamino;

or a salt thereof;

with the proviso that when A is $CR^1$, $R^1$ is Me, $R^2$ is pyridine or

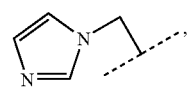

B is $NR^3$, $R^3$ is Me, K, L, M is CH, $Y^1$ is O, and Z is $OR^6$, then $R^6$ is not H;

and with the proviso that when A is NR¹, R¹ is H, R² is phenyl, B is CR³, R³ is phenyl, K, L, M is CH, Y¹ is O, and Z is OR⁶, then R⁶ is not H;

and with the proviso that when A is S, R² is bromine, B is CR³, R³ is Me, K is CH, L is CH, M is CR⁷, R⁷ is H or Me, Y¹ is O, and Z is OR⁶, then R⁶ is not H;

and with the proviso that when A is O, R² is H, B is CR³, R³ is phenyl, K, L, M is CH, Y¹ is O and Z is OR⁶, then R⁶ is not H;

and with the proviso that when A is CR¹, R¹ is Me, R² is pyridine, B is NR³, R³ is Me, K, L, M is CH, Y¹ is O, and Z is OR⁶, then R⁶ is not Me;

and with the further proviso that when A is CR¹, R¹ is Me, R² is

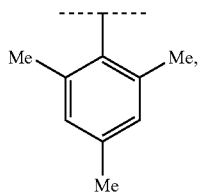

B is NR³, R³ is Me, K, L, M is CH, Y¹ is O and Z is OR⁶, then R⁶ is not Et; and with the further proviso that when A is CR¹, R¹ is CH, R² is Me, B is NR³, R³ is Me, K, L, M is CH, Y¹ is O and Z is OR⁶, then R⁶ is not Et;

and with the further proviso that when A is CR¹, R¹ is Et, R² is Me, B is NR³, R³ is Me, K, L, M is CH, Y¹ is O, and Z is OR⁶, then R⁶ is not CH₂CH₂N(Me)₂;

and with the further proviso that when A is CH, R² is Me, B is NR³, R³ is

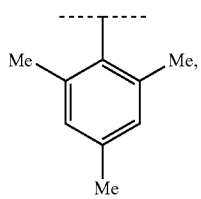

K is N, L is CR⁵, R⁵ is Me, M is CR⁷, R⁷ is OH, Y¹ is O, and Z is OR⁶ then R⁶ is not Et;

and with the further proviso that when A is NR¹, R¹ is Me, R² is Br, B is CR³, R³ is

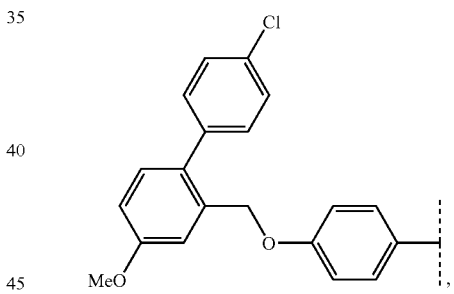

K is N, L is CR⁵, R⁵ is Me, M is CR⁷, R⁷ is Br, Y¹ is O, and Z is OR⁶, then R⁶ is not Me;

and with the further proviso that when A is NR¹, R¹ is H, R² is Cl, B is CR³, R³ is Et, K is CH, L is CH, M is CH, Y¹ is O, Z is OR⁶, then R⁶ is not Me;

and with the further proviso that when A is NR¹, R¹ is H, R² is phenyl, B is CR³, R³ is phenyl, K is CH, L is CH, M is CR⁷, R⁷ is Me, Y¹ is O, Z is OR⁶, then R⁶ is not Et;

and with the further proviso that when A is NR¹, R¹ is H, R² is

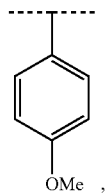

B is CR³, R³ is

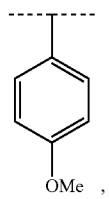

K is CH. L is N, M is CH, Y¹ is O, and Z is OR⁶, then R⁶ is not Et;

with the further proviso that when A is S, R² is Br, B is CR³, R³ is Me, K is CH, L is CH, M is CH, Y¹ is O, and Z is OR⁶, then R⁶ is not Me;

and with the further proviso that, when A is NR¹, R¹ is H, R² is:

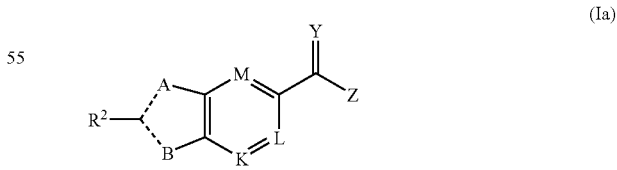

B is NR³, R³ is cyclohexyl, K, L, M is CH, Y¹ is O, Z is OR⁶, then R⁶ is not H.

Alternatively, in a first aspect of the invention, there is provided a compound represented by Formula Ia:

(Ia)

wherein:

A is O, S, NR¹, or CR¹;

B is NR³ or CR³;

R¹ is selected from the group consisting of: H(C₁₋₆)alkyl, benzyl, (C₁₋₆ alkyl)-(C₆₋₁₀aryl), (C₁₋₆ alkyl)-5- or 6-membered heterocycle having 1 to 4 heteroatoms selected from O, N, and S, and 5- or 6-membered heterocycle having 1 to 4 heteroatoms selected from O, N and S, wherein said benzyl and said heteroatom are optionally substituted with from 1 to 4 substituents selected from the group consisting of: COOH, COO($C_{1-6}$ alkyl), halogen, and ($C_{1-6}$ alkyl);

$R^2$ is selected from the group consisting of: H, halogen, ($C_{1-6}$) alkyl, ($C_{3-7}$)cycloalkyl, phenyl, 5- or 6-membered heterocycle having 1 to 4 heteroatoms selected from O, N, and S, pyridine-N-oxide, and 9- or 10-membered heterobicycle having 1 to 4 heteroatoms selected from O, N and S, said phenyl, heterocycle and heterobicycle being optionally substituted with from 1 to 4 substituents selected from the group consisting of: halogen, C(halogen)$_3$, ($C_{1-6}$)alkyl, OH, O($C_{1-6}$ alkyl), NH$_2$, and N($C_{1-6}$ alkyl)$_2$;

$R^3$ is selected from the group consisting of: 5-, 6- or 7-membered heterocycle having 1 to 4 heteroatoms selected from O, N, and S, norbornane, ($C_{3-7}$)cycloalkyl and ($C_{3-7}$)cycloalkyl-($C_{1-6}$ alkyl);

M is N, $CR^4$, or $COR^5$, wherein $R^4$ is selected from the group consisting of: H, halogen, and ($C_{1-6}$ alkyl); and $R^5$ is selected from the group consisting of: H and ($C_{1-6}$ alkyl);

K and L is N or CH;

— represents either a single or a double bond;

Y is O;

Z is $OR^6$ or $NR^6R^{6a}$, wherein $R^6$ is selected from the group consisting of: H, ($C_{1-6}$)alkyl, wherein said alkyl is optionally substituted with from 1 to 4 substituents selected from: OH, COOH, COO($C_{1-6}$)alkyl, ($C_{1-6}$)alkyl, said alkyl being optionally substituted with from 1 to 4 substituents selected from: COOH, NHCO($C_{1-6}$ alkyl), NH$_2$, NH($C_{1-6}$ alkyl), and N($C_{1-6}$ alkyl)$_2$;

or a salt thereof.

In a third aspect of the invention, there is provided a compound of the formula I, or a pharmaceutically acceptable salt thereof, as an inhibitor of RNA dependent RNA polymerase activity of the enzyme NS5B, encoded by HCV.

In a fourth aspect of the invention, there is provided a compound of the formula I, or a pharmaceutically acceptable salt thereof, as an inhibitor of HCV replication.

In a fifth aspect of the invention, there is provided a method of treating or preventing HCV infection in a mammal, comprising administering to the mammal an effective amount of a compound of formula I, or a pharmaceutically acceptable salt thereof.

In a sixth aspect of the invention, there is provided a pharmaceutical composition for the treatment or prevention of HCV infection, comprising an effective amount of a compound of formula I, or a pharmaceutically acceptable salt thereof, and a pharmaceutically acceptable carrier.

According to a specific embodiment, the pharmaceutical compositions of this invention comprise an additional immunomodulatory agent. Examples of additional immunomodulatory agents include but are not limited to, α-, β-, δ- γ-, and ω-interferons.

According to an alternate embodiment, the pharmaceutical compositions of this invention may additionally comprise an antiviral agent. Examples of antiviral agents include, ribavirin and amantadine.

According to another alternate embodiment, the pharmaceutical compositions of this invention may additionally comprise other inhibitors of HCV polymerase.

According to yet another alternate embodiment, the pharmaceutical compositions of this invention may additionally comprise an inhibitor of other targets in the HCV life cycle, such as helicase, polymerase, metalloprotease or IRES.

In a seventh aspect of the invention, there is provided a use of a compound of formula I, for the manufacture of a medicament for the treatment of HCV infection.

In an eighth aspect of the invention, there is provided a use of a compound of formula I, as an HCV polymerase inhibitor.

In a ninth aspect of the invention, there is provided a method of treating or preventing HCV infection in a mammal, comprising administering to the mammal an effective amount of a compound of formula I, or a pharmaceutically acceptable salt thereof in combination with another anti-HCV agent.

In a tenth aspect of the invention, there is provided an intermediate of formula (1a) or (1b):

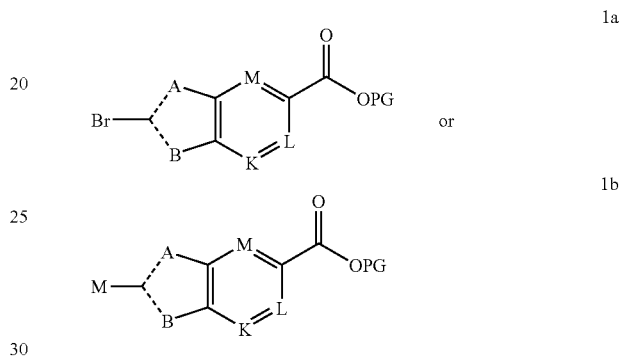

wherein A, B, K, L, and M are as described herein and PG is H or a carboxy protecting group.

In a eleventh aspect of the invention, there is provided the use of the intermediates of formula (Ia) for producing compounds of formula (iii),

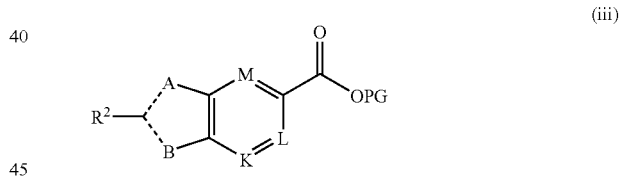

wherein A, $R^2$, B, K, L, M, and PG are as described herein, comprising:

a) coupling, in the presence of a metal catalyst (such as, for example, Pd, Ni, Ru, Cu), a base and an additive (such as a phosphine ligand, Cu salt, Li salt, ammonium salt, CsF) in an appropriate solvent, intermediate (1a):

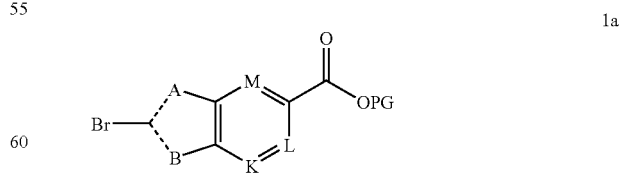

with $R^2$—X, wherein $R^1$, $R^3$, K, L, M and PG are as described herein and X is (but not limited to): Sn($C_{1-6}$alkyl)$_3$, Sn(aryl)$_3$, metal halide, B(OH)$_2$, and B(O($C_{1-6}$)alkyl)$_2$ to produce compounds of formula (iii).

In an alternative to the eleventh aspect of the invention, there is provided the use of intermediate (Ib) for producing compounds of formula (iii),

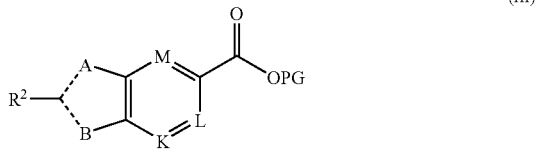
(iii)

wherein A, $R^2$, B, K, L, M, and PG are as described herein, comprising:
b) coupling, in the presence of a metal catalyst (such as, for example, Pd, Ni, Ru, Cu), a base and an additive (such as a phosphine ligand, Cu salt, Li salt, ammonium salt, CsF) in an appropriate solvent, intermediate (1b)

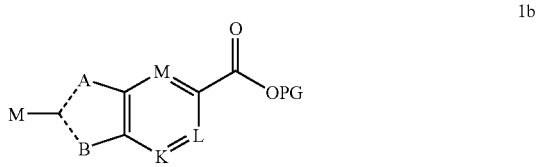
1b with $R^2$—X', wherein X' is halide, $OSO_2(C_{1-6}alkyl)$, $OSO_2Ar$, $OSO_2CF_3$ and the like, and M is a metal such as Li, $Sn(C_{1-6}alkyl)_3$, $Sn(aryl)_3$, $B(OH)_2$, $B(OC_{1-6}alkyl)_2$, metal halide, to produce compounds of formula (iii).

DETAILED DESCRIPTION OF THE INVENTION

Definitions

The following definitions apply unless otherwise noted:

As used herein, the terms "$(C_{1-3})$ alkyl", "$(C_{14})$ alkyl" or "$(C_{1-6})$ alkyl", either alone or in combination with another radical, are intended to mean acyclic straight or branched chain alkyl radicals containing up to three, four and six carbon atoms respectively. Examples of such radicals include methyl, ethyl, propyl, butyl, hexyl, 1-methylethyl, 1-methylpropyl, 2-methylpropyl, 1,1-dimethylethyl.

As used herein, the term "$(C_{2-6})$ alkenyl", either alone or in combination with another radical, is intended to mean an unsaturated, acyclic straight chain radical containing two to six carbon atoms.

As used herein, the term "$(C_{2-6})$ alkynyl" either alone or in combination with another group, is intended to mean an unsaturated, acyclic straight chain sp hybridized radical containing 2 to six carbon atoms.

As used herein, the term "$(C_{3-7})$ cycloalkyl", either alone or in combination with another radical, means a cycloalkyl radical containing from three to seven carbon atoms and includes cyclopropyl, cyclobutyl, cyclopentyl, cyclohexyl and cycloheptyl.

As used herein, the term "$(C_{5-7})$cycloalkenyl", either alone or in combination with another radical, means an unsaturated cyclic radical containing five to seven carbon atoms.

As used herein, the term "carboxy protecting group" defines protecting groups that can be used during coupling and are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "aryl", or "6- or 10-membered aryl" either alone or in combination with another radical means aromatic radical containing six or ten carbon atoms, for example phenyl or naphthyl.

As used herein the term heteroatom means O, S or N.

As used herein, the term "heterocycle", either alone or in combination with another radical, means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, "heterobicyclic" as used herein, means a heterocycle as defined above fused to one or more other cycle, be it a heterocycle or any other cycle. Examples of such heterocycles include, but are not limited to, pyrrolidine, tetrahydrofuran, thiazolidine, pyrrole, thiophene, coumarin, hydantoin, diazepine, 1H-imidazole, isoxazole, thiazole, tetrazole, piperidine, 1,4-dioxane, 4-morpholine, pyridine, pyridine-N-oxide, pyrimidine, thiazolo[4,5-b]-pyridine, quinoline, or indole, or the following heterocycles:

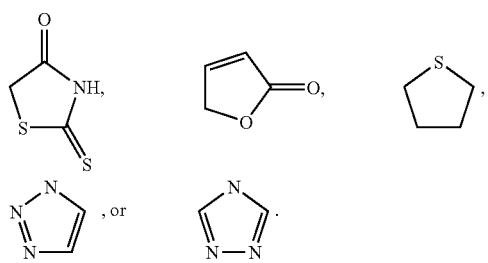

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, thiazolo[4,5-b]-pyridine, quinoline, or indole, or the following:

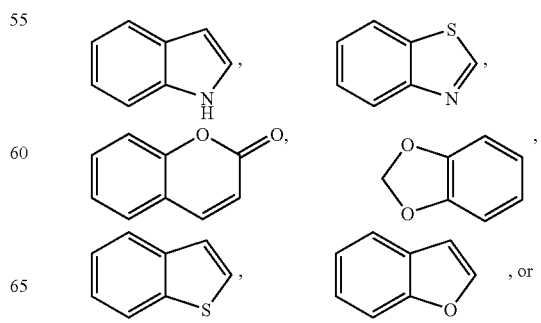

-continued

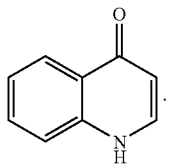

As used herein, the term "Het" defines a 5- or 6-membered heterocycle having 1 to 4 heteroatoms selected from O, N, and S, or a 9- or 10-membered heterobicycle having 1 to 5 heteroatoms wherever possible, selected from O, N and S.

As used herein, the term "halo" means a halogen atom and includes fluorine, chlorine, bromine and iodine.

As used herein, the term "haloalkyl" is intended to mean an alkyl that is described above in which each hydrogen atom may be successively replaced by a halogen atom, for example $CH_2Br$ or $CF_3$.

As used herein, the term "metal halide" is intended to mean any metal that is bonded to a halogen atom for use in a metal-catalyzed cross-coupling reaction.

Examples of such metal halides include, but are not limited to, —MgCl, —CuCl, or —ZnCl and the like.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as $SOR$, $SO_2R$, or $SO_3R$.

It is intended that the term "substituted" when applied in conjunction with a radical having more than one moiety such as $C_{1-6}$alkyl-aryl, or $C_{1-6}$alkyl-Het, such substitution applies to both moieties i.e. both the alkyl and aryl or Het moieties can be substituted with the defined substituents.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, boronic acids or tetrazole.

As used herein, the term "functional group equivalent" is intended to mean an element or a substituted derivative thereof, that is replaceable by another element that has similar electronic, hybridization or bonding properties.

As used herein, the term "metal catalyst" is intended to mean a metal such as palladium (0) or palladium (2) that is bonded to a leaving group for use in a cross-coupling reaction. Examples of such palladium catalysts include, but are not limited to, $Pd(Ph_3)_4$, Pd/C, $Pd(OAc)_2$, $PdCl_2$, and the like. Alternative metals that can catalyze cross-coupling reactions include, but are not limited to: $Ni(acac)_2$, $Ni(OAc)_2$, or $NiCl_2$.

As used herein, the term "derivative" is intended to mean "detectable label", "affinity tag" or "photoreactive group". The term "detectable label" refers to any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the polymerase by well known methods.

The term "affinity tag" means a ligand (that is linked to the polymerase or to a compound of the present invention) whose strong affinity for a receptor can be used to extract from a solution the entity to which the ligand is attached. Examples of such ligands include biotin or a derivative thereof, a histidine polypeptide, a polyarginine, an amylose sugar moiety or a defined epitope recognizable by a specific antibody. Such affinity tags are attached to the compound or to the polymerase by well-known methods.

The term "photoreactive group" means a group that is transformed, upon activation by light, from an inert group to a reactive species, such as a free radical. Examples of such groups include, but are not limited to, benzophenones, azides, and the like.

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1-19, incorporated herein by reference).

Preferred Embodiments

A:

Preferably, compounds of the present invention have the following formula (II):

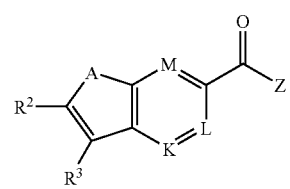

(II)

wherein, preferably, A is O, S, or $NR^1$.

Preferably, A is $NR^1$.

Preferably, compounds of the present invention have the following formula (III):

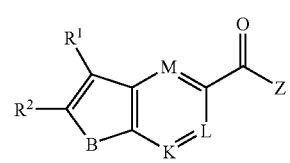

(III)

wherein, preferably, B is $NR^3$.

With respect to compounds of formula (II) and (III), preferably, M, K and L is CH or N. More preferably, K and L is CH.

More preferably, compounds of the present invention have the following formulae:

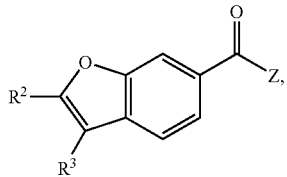

IIa

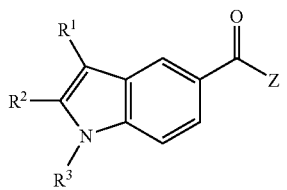

IIIa

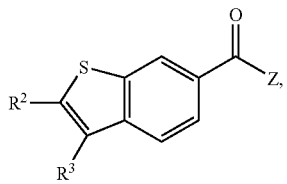

IIb

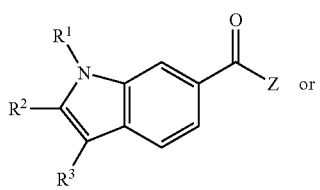

IIc

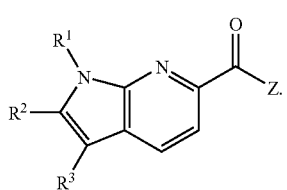

IId $R^1$:

Preferably $R^1$ is selected from the group consisting of: H or $(C_{1-6})$alkyl. More preferably, $R^1$ is H, $CH_3$, isopropyl, or isobutyl. Even more preferably, $R^1$ is H or $CH_3$. Most preferably, $R^1$ is $CH_3$.

$R^2$:

Preferably, $R^2$ is selected from: H, halogen, $(C_{2-6})$alkenyl, $(C_{5-7})$cycloalkenyl, 6 or 10-membered aryl or Het; wherein $(C_{2-6})$alkenyl, $(C_{5-7})$cycloalkenyl, aryl or Het is optionally substituted with $R^{20}$, wherein $R^{20}$ is defined as:

1 to 4 substituents selected from: halogen, $NO_2$, cyano, azido, $C(=NH)NH_2$, $C(=NH)NH(C_{1-6})$alkyl or $C(=NH)NHCO(C_{1-6})$alkyl; or 1 to 4 substituents selected from:
a) $(C_{1-6})$ alkyl or haloalkyl, $(C_{3-7})$cycloalkyl, $(C_{2-6})$alkenyl, $(C_{2-8})$alkynyl, $(C_{1-6})$ alkyl-$(C_{3-7})$cycloalkyl, all of which optionally substituted with $R^{150}$;
b) $OR^{104}$ wherein $R^{104}$ is H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

c) $OCOR^{105}$ wherein $R^{105}$ is $(C_{1-6})$alkyl, $(C_{3-7})$cycloalkyl, $(C_{1-6})$alkyl-$(C_{3-7})$cycloalkyl, Het, $(C_{1-6})$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl or $(C_{1-6}$alkyl)Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl)aryl, $(C_{1-6}$alkyl)Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl)aryl or $(C_{1-6}$alkyl)Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het being optionally substituted with $R^{150}$;

g) $NR^{18}CONR^{119}R^{120}$, wherein $R^{118}R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle;

said alkyl, cycloalkyl, $(C_{1-6})$alkyl-$(C_{3-7})$cycloalkyl, aryl, Het, $(C_{1-6}$alkyl)aryl or $(C_{1-6}$alkyl)Het or heterocycle being optionally substituted with $R^{150}$;

h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$; or $R^{122}$ is $OR^{123}$ or $N(R^{124})_2$ wherein $R^{123}$ and each $R^{124}$ is independently H $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl)

aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;

j) $COOR^{128}$ wherein $R^{128}$ is H, $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, said $(C_{1-6})$alkyl, $(C_{3-7})$cycloalkyl, or $(C_{1-6})$alkyl-$(C_{3-7})$cycloalkyl, aryl, Het, $(C_{1-6}$alkyl)aryl and $(C_{1-6}$alkyl)Het being optionally substituted with $R^{150}$;

k) $CONR^{129}R^{130}$ wherein $R^{129}$ and $R^{130}$ are independently H, $(C_{1-6})$alkyl $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$, l) aryl, Het, $(C_{1-6}$alkyl)aryl or $(C_{1-6}$alkyl)Het, all of which being optionally substituted with $R^{150}$;

wherein $R^{150}$ is preferably:

1 to 3 substituents selected from: halogen, $NO_2$, cyano or azido; or 1 to 3 substituents selected from:

a) $(C_{1-6})$ alkyl or haloalkyl, $(C_{3-7})$cycloalkyl, $(C_{2-6})$alkenyl, $(C_{2-8})$alkynyl, $(C_{1-6})$ alkyl-$(C_{3-7})$cycloalkyl, all of which optionally substituted with $R^{160}$;

b) $OR^{104}$ wherein $R^{104}$ is H, $(C_{1-6}$alkyl) or $(C_{3-7})$cycloalkyl, said alkyl or cycloalkyl optionally substituted with $R^{160}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, or both $R^{108}$ are covalently bonded together and to the nitrogen to which they are attached to form a 5, 6 or 7-membered saturated heterocycle, said alkyl, cycloalkyl, aryl, Het and heterocycle being optionally substituted with $R^{160}$;

e) $NR^{111}R^{112}$ wherein $R^{111}$ is H, $(C_{1-6})$alkyl, or $(C_{3-7})$cycloalkyl, and $R^{112}$ is H, $(C_{1-6})$alkyl or $(C_{3-7})$cycloalkyl, $COOR^{115}$ or $SO_2R^{115}$ wherein $R^{115}$ is $(C_{1-6})$alkyl or $(C_{3-7})$cycloalkyl, or both $R^{111}$ and $R^{112}$ are covalently bonded together and to the nitrogen to which they are attached to form a 5, 6 or 7-membered saturated heterocycle, said alkyl, cycloalkyl and heterocycle being optionally substituted with $R^{160}$;

f) $NR^{116}COR^{117}$ wherein $R^{116}$ and $R^{117}$ is each H, $(C_{1-6})$alkyl or $(C_{3-7})$cycloalkyl said $(C_{1-6})$alkyl and $(C_{3-7})$cycloalkyl being optionally substituted with $R^{160}$;

g) $NR^{118}CONR^{119}R^{120}$ wherein $R^{118}$, $R^{119}$ and $R^{120}$ is each H, $(C_{1-6})$alkyl or $(C_{3-7})$cycloalkyl, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle;

said alkyl, cycloalkyl, and heterocycle being optionally substituted with $R^{160}$;

h) $NR^{121}COCOR^{122}$ wherein $R^{121}$ is H, $(C_{1-6})$alkyl or $(C_{3-7})$cycloalkyl, said alkyl and cycloalkyl being optionally substituted with $R^{160}$;

or $R^{122}$ is $OR^{123}$ or $N(R^{124})_2$ wherein $R^{123}$ and each $R^{124}$ is independently H, $(C_{1-6}$alkyl) or $(C_{3-7})$cycloalkyl, or both $R^{124}$ are covalently bonded together to form a 5, 6 or 7-membered saturated heterocycle, said alkyl, cycloalkyl and heterocycle being optionally substituted with $R^{160}$;

i) $COR^{127}$ wherein $R^{127}$ is H, $(C_{1-6})$alkyl or $(C_{3-7})$cycloalkyl, said alkyl and cycloalkyl being optionally substituted with $R^{160}$;

j) $COOR^{128}$ wherein $R^{128}$ is H, $(C_{1-6})$alkyl or $(C_{3-7})$cycloalkyl, said $(C_{1-6})$alkyl and $(C_{3-7})$cycloalkyl being optionally substituted with $R^{160}$; and k) $CONR^{129}R^{130}$ wherein $R^{129}$ and $R^{130}$ are independently H, $(C_{1-6})$alkyl or $(C_{3-7})$cycloalkyl, or both $R^{129}$ and $R^{130}$ are covalently bonded together and to the nitrogen to which they are attached to form a 5, 6 or 7-membered saturated heterocycle, said alkyl, cycloalkyl and heterocycle being optionally substituted with $R^{160}$;

wherein $R^{160}$ is defined as 1 or 2 substituents selected from:

halogen, CN, $C_{1-6}$alkyl, haloalkyl, $COOR^{161}$, $OR^{161}$, $N(R^{162})_2$, $SO_2N(R^{162})_2$, $NR^{162}COR^{162}$ or $CON(R^{162})_2$, wherein $R^{161}$ and each $R^{162}$ is independently H, $(C_{1-6})$alkyl, $(C_{3-7})$cycloalkyl or $(C_{1-6})$alkyl-$(C_{3-7})$cycloalkyl; or both $R^{162}$ are covalently bonded together and to the nitrogen to which they are attached to form a 5, 6 or 7-membered saturated heterocycle.

More preferably, $R^2$ is selected from: aryl or Het, each optionally monosubstituted or disubstituted with substituents selected from the group consisting of: halogen, haloalkyl, $N_3$, or a) $(C_{1-6})$alkyl optionally substituted with OH, $O(C_{1-6})$alkyl or $SO_2(C_{1-6}$ alkyl);

b) $(C_{1-6})$alkoxy;

e) $NR^{111}R^{112}$ wherein both $R^{111}$ and $R^{112}$ are independently H, $(C_{1-6})$alkyl, $(C_{3-7})$cycloalkyl, or $R^{112}$ is 6- or 10-membered aryl, Het, $(C_{1-6})$alkyl-aryl or $(C_{1-6})$alkyl-Het; or both $R^{111}$ and $R^{112}$ are covalently bonded together and to the nitrogen to which they are attached to form a nitrogen-containing heterocycle, each of said alkyl, cycloalkyl, aryl, Het, alkyl-aryl or alkyl-Het; being optionally substituted with halogen or:

$OR^{161}$ or $N(R^{162})_2$, wherein $R^{161}$ and each $R^{162}$ is independently H, $(C_{1-6})$alkyl, or both $R^{162}$ are covalently bonded together and to the nitrogen to which they are attached to form a nitrogen-containing heterocycle;

f) $NHCOR^{117}$ wherein $R^{117}$ is $(C_{1-6})$alkyl, $O(C_{1-6})$alkyl or $O(C_{3-7})$cycloalkyl;

i) CO-aryl; and k) $CONH_2$, $CONH(C_{1-6}$alkyl), $CON(C_{1-6}$alkyl)$_2$, CONH-aryl, or $CONHC_{1-6}$alkyl-aryl.

Still, more preferably, $R^2$ is aryl or Het, each optionally monosubstituted or disubstituted with substituents selected from the group consisting of: halogen, haloalkyl, or a) $(C_{1-6})$alkyl optionally substituted with OH, $O(C_{1-6})$alkyl or $SO_2(C_{1-6}$alkyl);

b) $(C_{1-6})$alkoxy; and e) $NR^{111}R^{112}$ wherein both $R^{111}$ and $R^{112}$ are independently H, $(C_{1-6})$alkyl, $(C_{3-7})$cycloalkyl, or $R^{112}$ is 6- or 10-membered aryl, Het, $(C_{1-6})$alkyl-aryl or $(C_{1-6})$alkyl-Het; or both $R^{111}$ and $R^{112}$ are covalently bonded together and to the nitrogen to which they are attached to form a nitrogen-containing heterocycle, each of said alkyl, cycloalkyl, aryl, Het, alkyl-aryl or alkyl-Het; or being optionally substituted with halogen or:

$OR^{161}$ or $N(R^{162})_2$, wherein $R^{161}$ and each $R^{162}$ is independently H, $(C_{1-6})$alkyl, or both $R^{162}$ are covalently bonded together and to the nitrogen to which they are attached to form a nitrogen-containing heterocycle.
Even more preferably, R² is phenyl or a heterocycle selected from:
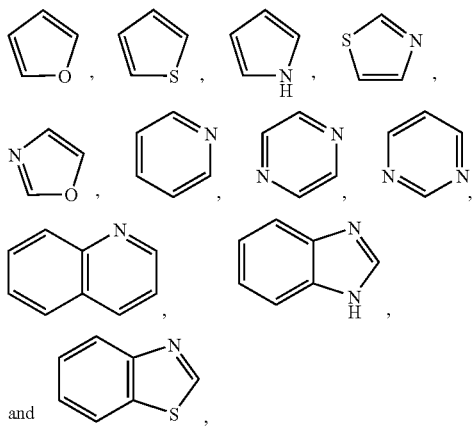
all of which optionally substituted as defined above.
Even more preferably, R² is selected from the group consisting of:
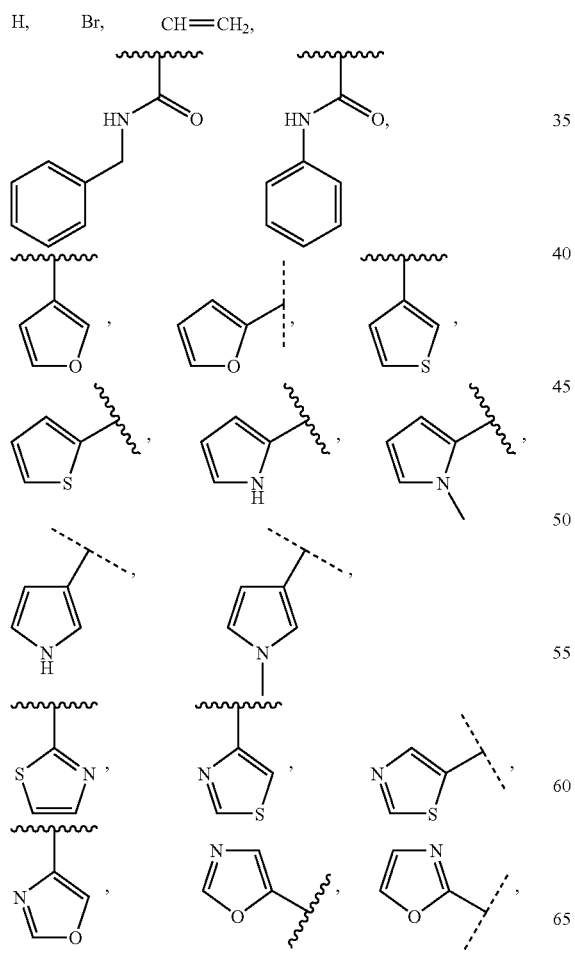
-continued
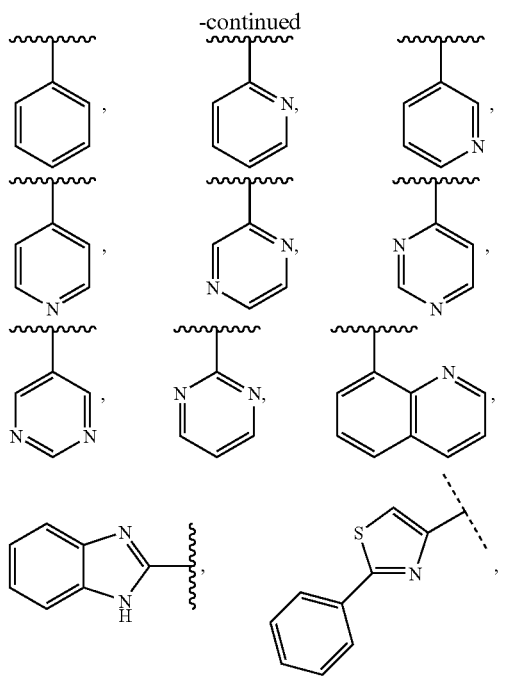
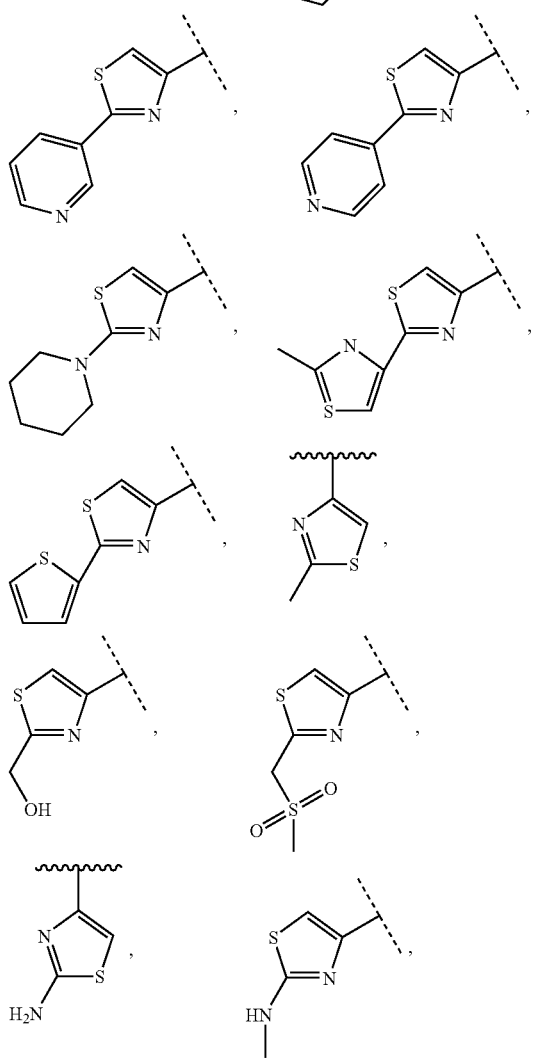

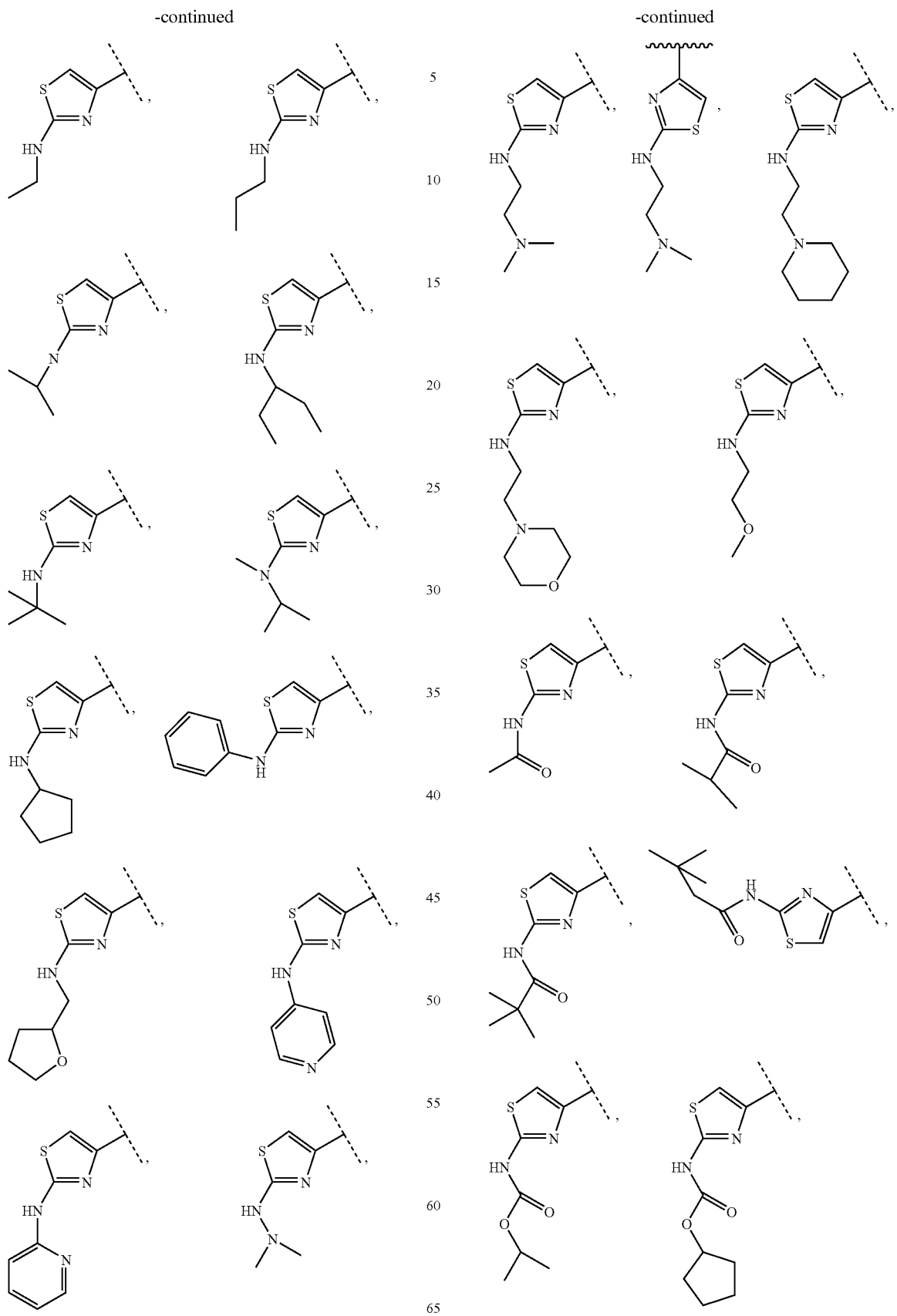

-continued
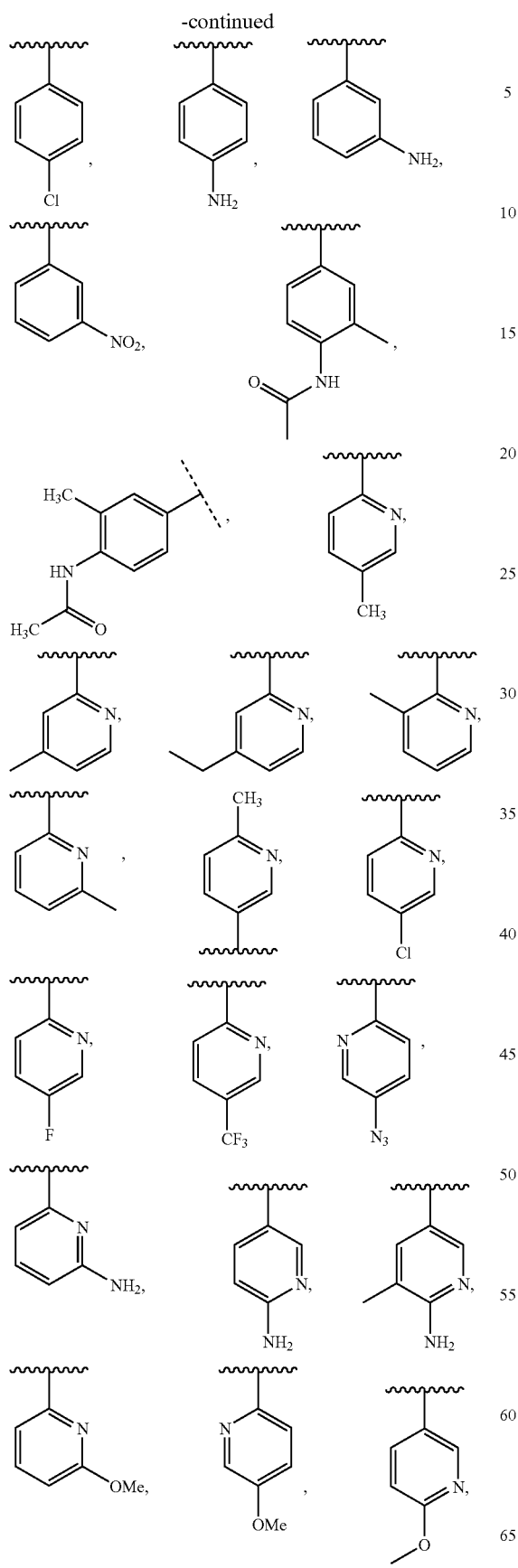
-continued
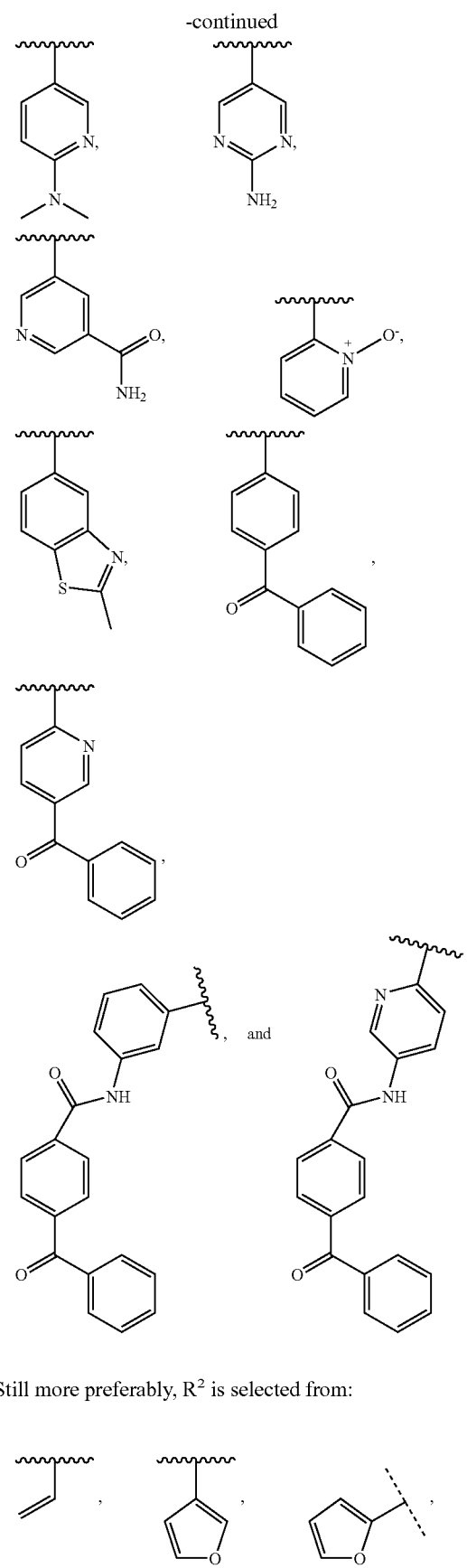
Still more preferably, R² is selected from:

-continued
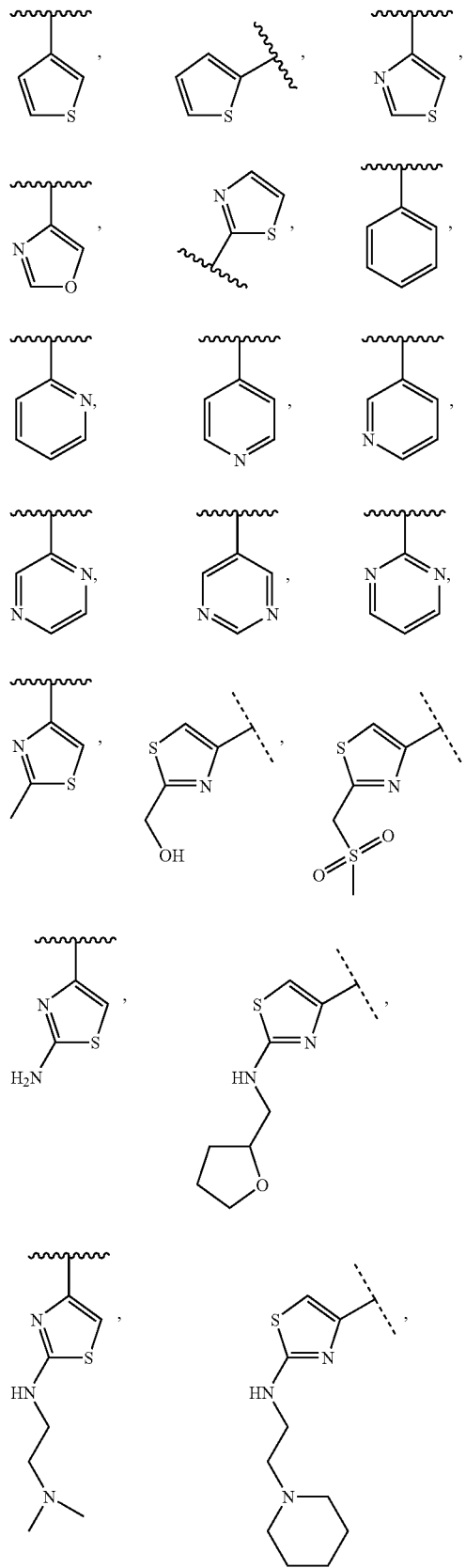
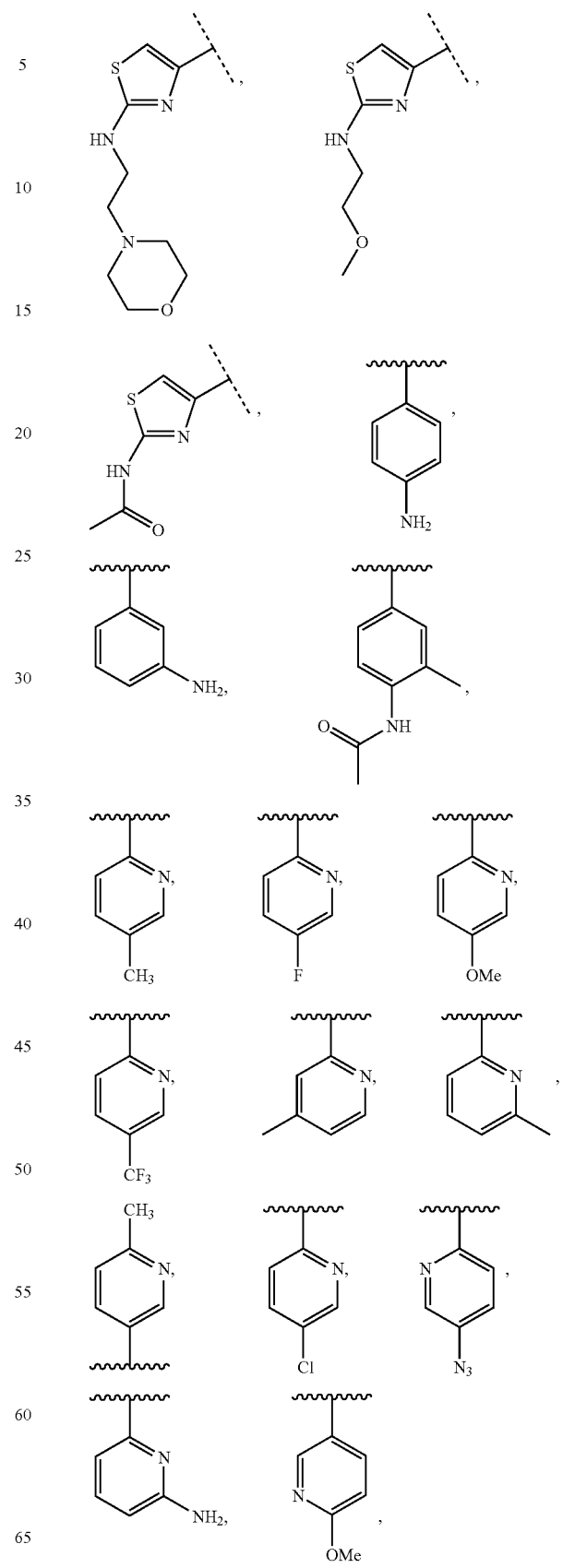

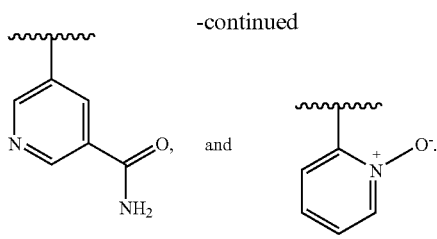

Most preferably, $R^2$ is selected from:

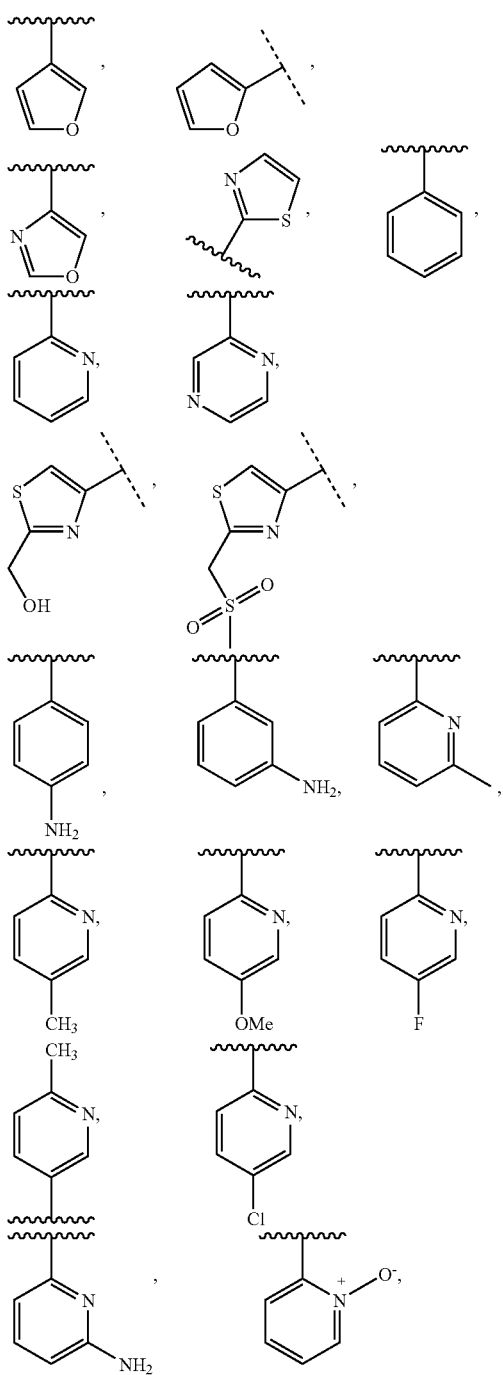

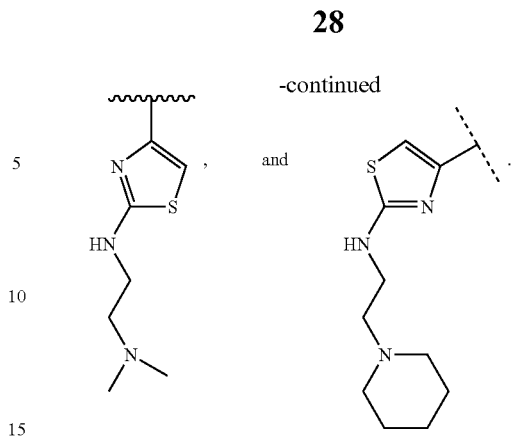

$R^3$:

Preferably, $R^3$ is selected from $(C_{3-7})$cycloalkyl, $(C_{3-7})$cycloalkenyl, $(C_{6-10})$bicycloalkyl, $(C_{6-10})$bicycloalkenyl, 6- or 10-membered aryl, or Het. More preferably, $R^3$ is $(C_{3-7})$cycloalkyl. Most preferably, $R^3$ is cyclopentyl, or cyclohexyl.

Y:

Preferably $Y^1$ is O.

Z:

Preferably, Z is $OR^6$, wherein $R^6$ is H, $(C_{1-6})$alkyl being optionally substituted with: halo, hydroxy, carboxy, amino, $C_{1-6}$ alkoxy, $C_{1-6}$alkoxycarbonyl, and $C_{1-6}$ alkylamino; or $R^6$ is $C_{1-6}$ alkylaryl optionally substituted with: halogen, cyano, nitro, $C_{1-6}$ alkyl, $C_{1-6}$haloalkyl, $C_{1-6}$alkanoyl, $—(CH_2)_{1-6}—COOR^7$, $—(CH_2)_{1-6}—CONR^7R^8$, $—(CH_2)_{1-6}—NR^7R^8$, $—(CH_2)_{1-6}—NR^7COR^8$, $—(CH_2)_{1-6}—NHSO_2R^7$, $—(CH_2)_{1-6}—OR^7$, $—(CH_2)_{1-6}—SR^7$, $—(CH_2)_{1-6}—SO_2R^7$, and $—(CH_2)_{1-6}—SO_2NR^7R^8$, wherein each $R^7$ and each $R^8$ is H or $C_{1-6}$ alkyl, or Z is $NR^9R^{10}$ wherein each of $R^9$ and $R^{10}$ is selected from: H, $C_{1-6}$alkoxy, or $C_{1-6}$alkyl optionally substituted with halo, hydroxy, carboxy, amino, $C_{1-6}$ alkoxy, $C_{1-6}$alkoxycarbonyl, and $C_{1-6}$ alkylamino;

More preferably, Z is OH or $O(C_{1-6}$alkyl) or Z is $NR^9R^{10}$ wherein $R^9$ is preferably H and $R^{10}$ is preferably H or $C_{1-6}$alkyl.

Most preferably, Z is OH.

Specific Embodiments

Included within the scope of this invention are all compounds of formula I as presented in Tables 1 and 2.

Polymerase Activity

The ability of the compounds of formula (I) to inhibit RNA synthesis by the RNA dependent RNA polymerase of HCV can be demonstrated by any assay capable of measuring RNA dependent RNA polymerase activity. A suitable assay is described in the examples.

Specificity for RNA Dependent RNA Polymerase Activity

To demonstrate that the compounds of the invention act by specific inhibition of HCV polymerase, the compounds may be tested for inhibitory activity in a DNA dependent RNA polymerase assay.

When a compound of formula (I), or one of its therapeutically acceptable salts, is employed as an antiviral agent, it is administered orally, topically or systemically to mammals, e.g. humans, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula (I) is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

For systemic administration, the compound of formula (I) is administered at a dosage of 10 mg to 150 mg per kilogram of body weight per day, although the aforementioned variations will occur. A dosage level that is in the range of from about 10 mg to 100 mg per kilogram of body weight per day is most desirably employed in order to achieve effective results.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS5B polymerase; inhibitors of other targets in the HCV life cycle, which include but not limited to, helicase, NS2/3 protease, NS3 protease, or internal ribosome entry site (IRES); or combinations thereof. The additional agents may be combined with the compounds of this invention to create a single dosage form. Alternatively these additional agents may be separately administered to a mammal as part of a multiple dosage form.

Methodology and Synthesis

Indole derivatives or analogs according to the present invention can be prepared from known monocyclic aromatic compounds by adapting known literature sequences such as those described by J. W. Ellingboe et al. (*Tet. Lett.* 1997, 38, 7963) and S. Cacchi et al. (*Tet. Lett.* 1992, 33, 3915). Scheme 1, shown below wherein $R^1$, $R^2$, $R^3$, $R^6$, K, L, and M are as described herein illustrate how these procedures can be adapted to the synthesis of compounds of formula 1 of this invention.

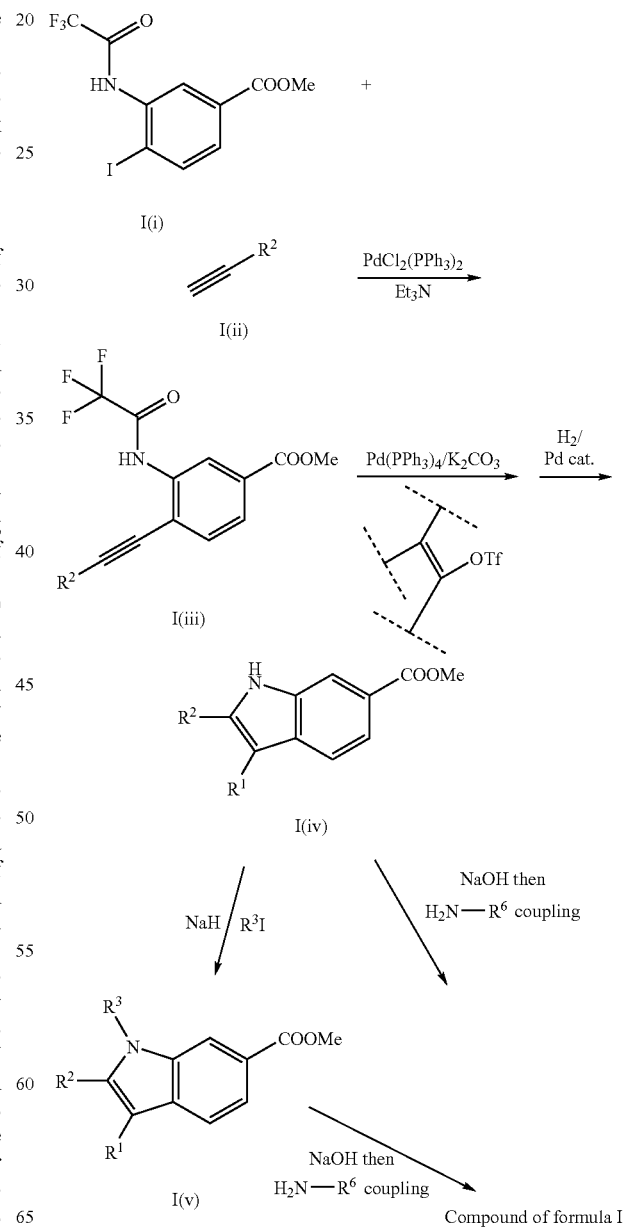

In carrying out the route illustrated in Scheme 1, a suitably protected form of 3-trifluoroacetamido-4-iodobenzoic acid I(i) is reacted with an alkyne I(ii) in the presence of a metal catalyst (e.g. a palladium metal complex such as PdCl$_2$(PPh$_3$)$_2$, Pd$_2$ dba$_3$, Pd(PPh$_3$)$_4$ and the like), a base (Et$_3$N, DIEA and the like or an inorganic basic salt including metal carbonates, fluorides and phosphates), and optionally in the presence of an additional phosphine ligand (triaryl or heteroarylphosphine, dppe, dppf, dppp and the like). Suitable solvents for this reaction include DMF, dioxane, THF, DME, toluene, MeCN, DMA and the like at temperatures ranging from 20° C. to 170° C., or alternatively without solvent by heating the components together. Alternatively, the cross-coupling reaction can be carried out on a suitably protected form of 3-amino-4-iodobenzoate and the amino group can be trifluoroacetylated in the subsequent step as described by J. W. Ellingboe et al. (*Tet. Lett.* 1997, 38, 7963).

Reaction of the above diarylalkynes I(iii) with an enol triflate under cross-coupling conditions similar to those described above gives after hydrogenation of the double bond, indole derivatives I(iv). Enol triflates are known and can be prepared from the corresponding ketones by following known literature methods (for example, cyclohexene triflate can be prepared from cyclohexanone, triflic anhydride and a hindered organic base such as 2,6-di-tert-butyl-4-methylpyridine). The hydrogenation of the double bond originally present in R$^1$ can be carried out with hydrogen gas or a hydrogen donor (ammonium formate, formic acid and the like) in the presence of a metal catalyst (preferably Pd) in a suitable solvent (lower alkyl alcohols, THF etc.).

Finally, following hydrolysis of the ester protecting group in I(iv), the resulting 6-carboxyindole derivative I(v) is converted to compounds of formula 1 by coupling with the appropriate amine of formula H$_2$N—R$^6$. Condensation of the 6-indolecarboxylic acid with amines H$_2$N—R$^6$ can be accomplished using standard amide bond forming reagents such as TBTU, HATU, BOP, BroP, EDAC, DCC, isobutyl chloroformate and the like, or by activation of the carboxyl group by conversion to the corresponding acid chloride prior to condensation with an amine. Any remaining protecting group is removed following this step to give compounds of formula 1.

Alternatively, compounds of formula 1 can be prepared by elaboration from a pre-existing indole core by following adaptations of literature procedures as described, for example, by P. Gharagozloo et al. (*Tetrahedron* 1996, 52, 10185) or K. Freter (*J. Org. Chem.* 1975, 40, 2525). Such a methodology is illustrated in Scheme 2:

Scheme 2

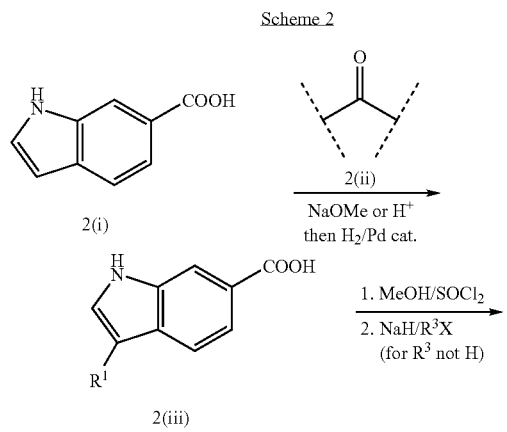

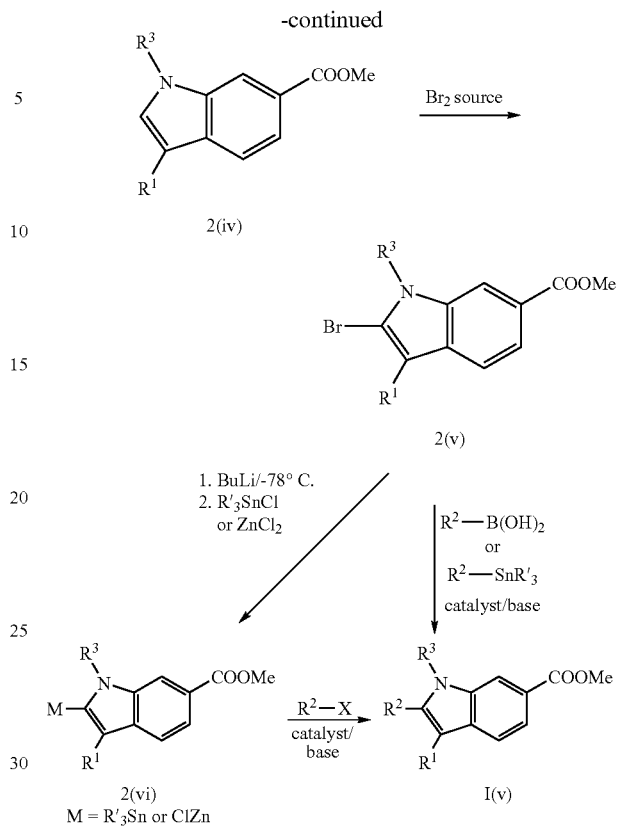

In carrying the route illustrated in Scheme 2, commercially available 6-indolecarboxylic acid 2(i), which can also be prepared according to the method of S. Kamiya et al. (*Chem. Pharm. Bull.* 1995, 43, 1692) is used as the starting material. The indole 2(i) is reacted with a ketone 2(ii) under basic or acidic aldol-type conditions. Suitable conditions to affect this condensation include strong bases such as alkali metal hydroxides, alkoxides and hydrides in solvents such as lower alkyl alcohols (MeOH, EtOH, tertBuOH etc.), THF, dioxane, DMF, DMSO, DMA and the like at reaction temperature ranging from –20° C. to 120° C. Alternatively, the condensation can be carried out under acid conditions using organic or mineral acids or both. Appropriate conditions include mixtures of AcOH and aqueous phosphoric acid at temperatures ranging from 15° C. to 120° C.

Following protection of the carboxylic acid group in the form of an ester (usually lower alkyl) using known methods, the indole nitrogen can be alkylated with R$^3$ if desired. Reaction conditions to alkylate the nitrogen of an indole derivative are well known to those skilled in the art and include the use of strong bases such as alkali metal hydrides, hydroxides, amides, alkoxides and alkylmetals, in the appropriate solvent (such as THF, dioxane, DME, DMF. MeCN, DMSO, alcohols and the like) at temperatures ranging from –78° C. to 140° C. An electrophilic form of R$^3$ is used for the alkylation of the indole anion. Such electrophilic species include iodides, bromides, chlorides and sulfonate esters (mesylates, tosylate, brosylate or triflate).

Halogenation (usually bromination, but also iodination) of the 2-position of the indole 2(iv) gives 2(v). Suitable halogenating agents include, for example, elemental bromine, N-bromosuccinimide, pyridine tribromide, dibromohydantoin and the corresponding iodo derivatives. Suitable solvents for this reaction are inert to reactive halogenating agents and include for example hydrocarbons, chlorinated hydrocarbons (DCM, CCl₄, CHCl₃), ethers (THF, DME, dioxane), acetic acid, ethyl acetate, IPA, and mixtures of these solvents. Reaction temperature ranges from −40° C. to 100° C. A method of choice to carry out the bromination of indoles as shown in Scheme 2 was described by L. Chu (*Tet. Lett.* 1997, 38, 3871).

The 2-bromoindole derivatives 2(v) can be converted directly to fully substituted key intermediates I(v) through a cross-coupling reaction with aryl or heteroaryl boronic acids, boronate esters or trialkylstannane derivatives. These boron or tin organometallic species are from commercial sources or can be prepared by standard literature procedures. Cross-coupling with organoboron reagents can be carried out by any variations of the Suzuki cross-coupling reaction reported in the literature. This usually involves the use of a transition metal catalyst (usually Pd°), triaryl or triheteroarylphosphine ligands, an additive such as an inorganic chloride (e.g. LiCl), and a base (usually an aqueous inorganic base such as sodium or potassium carbonate or phosphate). The reaction is usually carried out in an alcoholic solvent (EtOH), DME, toluene, THF and the like at temperatures ranging from 25° C. to 140° C.

Cross-coupling with tin reagents can be carried out by any variations of the Stille cross-coupling reaction reported in the literature. This usually involves the use of a transition metal catalyst (usually Pd°), triaryl or triheteroaryl phosphine ligands, and an additive such as an inorganic chloride (e.g. LiCl) or iodide (e.g. CuI). Suitable solvents for this reaction include toluene, DMF, THF, DME and the like at temperatures ranging from 25° C. to 140° C. Intermediate I(v) is then converted to compounds of formula 1 as described for Scheme 1.

Alternatively, the 2-bromoindole intermediate 2(v) can be trans-metallated to an organotin species (or organozinc) and used in Stille-type cross-coupling reactions under conditions described above. In this case, aromatic and heteroaromatic halides (chlorides, bromides, iodides) or triflates are used to introduce R². The conversion of 2-bromoindole derivatives 2(v) to the corresponding organotin species 2(vi) is carried out via initial low-temperature (usually −78° to −30° C.) halogen-metal exchange using an alkyllithium reagent (e.g. nBuLi or tert-BuLi) or using lithium metal. The transient 2-lithioindole species is then trapped with a trialkyltin halide (e.g. nBu₃SnCl or Me₃SnCl). Alternatively, the lithioindole intermediate can be trapped with zinc chloride to form the corresponding organozincate which can also undergo transition metal-catalyzed cross-coupling with aromatic and heteroaromatic halides or triflates as described, for example, by M. Rowley (*J. Med. Chem.* 2001, 44, 1603).

The present invention also encompasses compounds of formula 1 where the carboxylic group is in the 5-position of the indole system. The synthesis of such compounds is based on adaptation of literature procedures and is depicted in Scheme 3:

Scheme 3

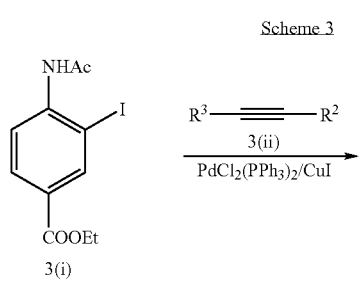

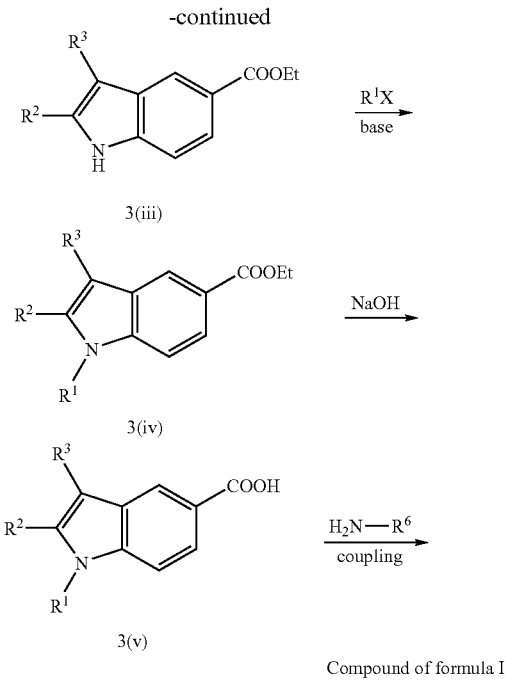

In carrying out the synthetic route illustrated in Scheme 3, ethyl 4-acetamido-3-iodobenzoate 3(i) undergoes metal catalyzed cross-coupling with an alkyne 3(ii) to give a 2,3-disubstituted-5-indolecarboxylate 3(iii) according to an adaptation of a procedure described by A. Bedeschi et al. (*Tet. Lett.* 1997, 38, 2307). The indole derivative 3(iii) is then alkylated on nitrogen with electrophilic R¹ groups (halides, sulfonate esters) under the action of a base such as alkali metal hydroxides, fluorides, hydrides amides, alkyllithium, phosphabases and the like, to give 3(iv). Suitable solvents for this alkylation include DMF, DMA, DMSO, MeCN, THF, dioxane, DME and the like. Following saponification of the ester group with an alkaline solution, the resulting 5-indolecarboxylic acid derivative 3(v) is coupled to H₂N—R⁶ using an amide bond forming reagent as described previously (Scheme 1), to give compounds of formula I.

EXAMPLES

The present invention is illustrated in further detail by the following non-limiting examples. All reactions were performed in a nitrogen or argon atmosphere. Temperatures are given in degrees Celsius. Flash chromatography was performed on silica gel. Solution percentages or ratios express a volume to volume relationship, unless stated otherwise. Mass spectral analyses were recorded using electrospray mass spectrometry. Abbreviations or symbols used herein include:

DIEA: diisopropylethylamine;

DMAP: 4-(dimethylamino)pyridine;

DMSO: dimethylsulfoxide;

DMF: N,N-dimethylformamide;

Et: ethyl;

EtOAc: ethyl acetate;

Et₂O: diethyl ether;

HPLC: high performance liquid chromatography;

*i*Pr: isopropyl

Me: methyl;

MeOH: Methanol;

MeCN: acetonitrile;

Ph: phenyl;

TBE: tris-borate-EDTA;

TBTU: 2-(1H-benzotriazol-1-yl)-N,N,N',N'-tetramethyluronium tetrafluoroborate;

TFA: trifluoroacetic acid;

TFAA: trifluoroacetic anhydride;

THF: tetrahydrofuran;

MS (ES): electrospray mass spectrometry;

PFU: plaque forming units;

DEPC: diethyl pyrocarbonate;

DTT: dithiothreitol

EDTA: ethylenediaminetetraacetate

HATU: O-(7-azabenzotriazol-1-yl)-N,N,N',N'-tetramethyluronium hexafluorophosphate BOP: benzotriazole-1-yloxy-tris(dimethylamino)phosphonium hexafluorophosphate EDAC: see ECD DCC: 1,3-Dicyclohexyl carbodiimide HOBt: 1-Hydroxybenzotriazole ES+: electro spray (positive ionization)

ES−: electro spray (negative ionization)

DCM: dichloromethane

TBME: tert-butylmethyl ether

TLC: thin layer chromatography

AcOH: acetic acid

EtOH: ethanol

DBU: 1,8-diazabicyclo[5.4.0]under-7-ene

BOC: tert-butyloxycarbonyl

Cbz: carbobenzyloxy carbonyl

*i*PrOH: isopropanol

NMP: N-methylpyrrolidone

EDC: 1-(3-dimethylaminopropyl)-3-ethyl carbodiimide hydrochloride

RNAsin: A ribonuclease inhibitor marketed by Promega Corporation

Tris: 2-amino-2-hydroxymethyl-1,3-propanediol

UMP: uridine 5'-monophosphate

UTP: uridine 5'-triphosphate

IPA: isopropyl acetate

Examples 1-22 illustrate methods of synthesis of representative compounds of this invention.

Example 1

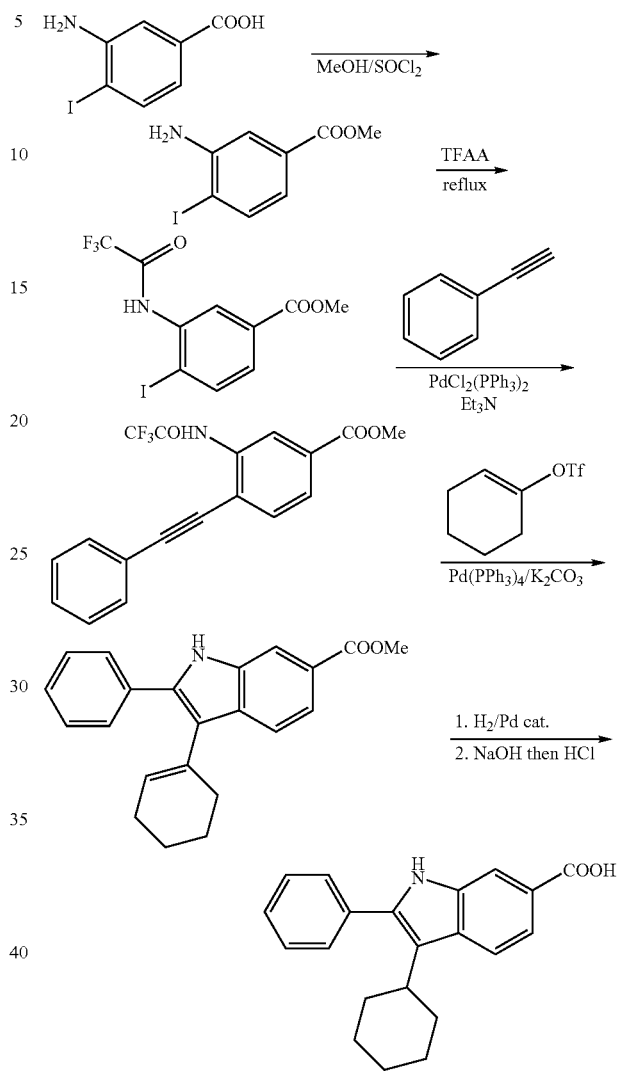

Methyl 3-amino-4-iodobenzoate

3-Amino-4-iodobenzoic acid (13.35 g, 50.8 mmol) was added to MeOH (150 mL) and SOCl$_2$ (4.8 mL, 65.8 mmol, 1.3 equivalent) was added. The mixture was refluxed for 3 h and then volatiles were removed under reduced pressure. The residue was co-evaporated three times with MeOH and dried in vacuo (15.23 g).

Methyl 3-trifluoroacetamido-4-iodobenzoate

The aniline derivative from above (14.53 g, 52 mmol) was dissolved in DCM (200 mL) and TFAA (15 mL, 104 mmol) was added. The dark purple solution was refluxed overnight. Volatiles were removed under reduced pressure and the residue was passed through a short pad of silica gel using DCM as eluent. The desired product was obtained as a pink solid (13.81 g).

4-Phenylethynyl-3-(2,2,2-trifluoro-ethanoylamino)-benzoic acid methyl ester

The iodide from above (0.742 g, 2 mmol), phenylacetylene (0.37 mL, 3.9 mmol, 1.7 equivalent) and $Et_3N$ (6 mL) were charged in a dry flask under argon. $PdCl_2(PPh_3)_2$ (0.241 g, 0.3 mmol) was added and the mixture was stirred at room temperature until judged complete by HPLC analysis (~5 h). The reaction mixture was concentrated to half volume under reduced pressure and diluted with water (80 mL). The mixture was extracted with EtOAc (3×100 mL) and the organic extract washed with 5% HCl (100 mL), after (100 mL) and brine (40 mL). After drying over $MgSO_4$, the residue was purified by flash chromatography using 20% EtOAc-hexane as eluent to give the desired cross-coupled alkyne as a tan solid (0.442 g).

Methyl 3-(cyclohexenyl)-2-phenylindole 6-carboxylate

A flame-dried flask was charged with finely powdered anhydrous $K_2CO_3$ (0.153 g, 1.1 mmol) and the alkyne derivative from above (0.390 g, 1.1 mmol). Dry DMF (4 mL) was added and the suspension degassed with a stream of argon. The enol triflate derived from cyclohexanone, prepared following the procedure described by A. G. Martinez, M. Hanack et al. (*J. Heterocyclic Chem.* 1988, 25, 1237 or equivalent methods described in the literature, (0.802 g, 3.3 mmol, 3 equivalents) was added followed by $Pd(PPh_3)_4$ (0.086 g, 0.07 mmol) and the mixture was stirred for 8 h at room temperature. DMF was removed under vacuum and the residue purified by flash chromatography using DCM as eluent (0.260 g).

Methyl 3-cyclohexyl-2-phenylindole-6-carboxylate

The material from above was hydrogenated (1 atm $H_2$ gas) over 20% $Pd(OH)_2$ in the usual manner, using MeOH as solvent. The desired cyclohexane indole was isolated after filtration of the catalyst.

3-Cylohexyl-2-phenylindole-6-carboxylic acid

The methyl ester from above (0.154 g, 0.15 mmol) was refluxed overnight in a mixture of MeOH (10 mL) and 2N NaOH (6 mL) until complete hydrolysis had occurred as shown by HPLC analysis. After cooling to room temperature, 2N HCl (5 mL) was added followed by AcOH to pH 7. MeOH was removed under reduced pressure, water (50 mL) was added and the product extracted with EtOAc. The extract was washed with water an brine, and dried ($MgSO_4$). Removal of volatiles under reduced pressure gave the title indole carboxylic acid as a light-orange solid (0.149 g).

Following the same procedure but using 2-ethynylpyridine instead of phenylacetylene, 3-cyclohexane-2-(2-pyridyl)indole-6-carboxylic acid was obtained.

Example 2

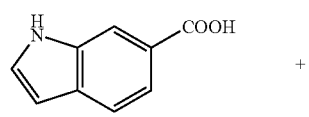

+

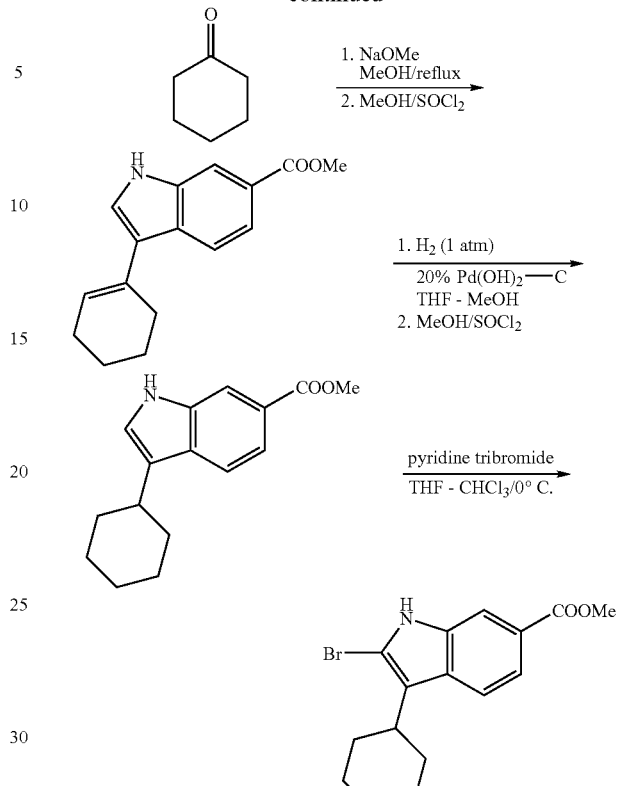

3-Cyclohexenyl-6-indole carboxylic acid

A 12 L round-bottomed flask was equipped with a reflux condenser and a mechanical stirrer, and the system was purged with nitrogen gas. 6-Indole carboxylic acid (300.00 g, 1.86 mole, 3 equivalents) was charged into the flask, followed by MeOH (5.5 L). After stirring for 10 min at room temperature, cyclohexanone (579 mL, 5.58 mole) was added. Methanolic sodium methoxide (25% w/w, 2.6 L, 11.37 mole, 6.1 equivalents) was added in portions over 10 min. The mixture was then refluxed for 48 h. After cooling to room temperature, water (4 L) was added and methanol removed under reduced pressure. The residual aqueous phase was acidified to pH 1 with concentrated HCl (~1.2 L). The resulting yellowish precipitate was collected by filtration, washed with water and dried under vacuum at 50° C. The desired cyclohexane derivative was obtained as a beige solid (451.0 g, 100% yield).

3-Cyclohexyl-6-indole carboxylic acid

The unsaturated derivative from above was hydrogenated for 20 h under 55 psi hydrogen gas pressure over 20% P d(OH)$_2$/C (10.25 g) using 1:1 THF-MeOH (2.5 L) as solvent. After filtration of the catalyst, volatiles were removed under reduced pressure and the residue was triturated with hexane. The beige solid was collected by filtration, washed with hexane and dried under vacuum (356.4 g, 78% yield).

Methyl 3-cyclohexyl-6-indole carboxylate

A 5 L three-necked flask was equipped with a reflux condenser and a mechanical stirrer, and the system was purged with nitrogen gas. The indole carboxylic acid from above (300.00 g, 1.233 mole) was charged into the flask and suspended in MeOH (2 L). Thionyl chloride (5 mL, 0.0685 mole, 0.05 equivalent) was added dropwise and the mixture was refluxed for 48 h. Volatiles were removed under reduced pressure and the residue was triturated with hexane to give a beige solid that was washed with hexane and dried under vacuum (279.6 g, 88% yield).

Methyl-2-bromo-3-cyclohexyl-6-indole carboxylate

Adapting the procedure of L. Chu (*Tet. Lett.* 1997, 38, 3871) methyl 3-cyclohexyl-6-indole carboxylate (4.65 g, 18.07 mmol) was dissolved in a mixture of THF (80 mL) and $CHCl_3$ (80 mL). The solution was cooled in an ice bath and pyridinium bromide perbromide (pyridine tribromide, 7.22 g, 22.6 mmol, 1.25 equivalent) was added. After stirring for 1.5 h at 0° C., the reaction was judged complete by TLC. It was diluted with $CHCl_3$ (200 mL), washed with 1M $NaHSO_3$ (2×50 mL), saturated aqueous $NaHCO_3$ (2×50 mL) and brine (50 mL). After drying over $Na_2SO_4$, the solvent was removed under reduced pressure and the residue crystallized from TBME-hexane. The desired 2-bromoindole derivative was collected by filtration, washed with hexane and dried (3.45 g). Evaporation of mother liquors gave a red solid that was purified by flash chromatography using 15% EtOAc in hexane yielding an additional 3.62 g of pure material. Total yield was 5.17 g (85% yield).

Example 3

General Procedure for the Suzuki Cross-Coupling of Aryl and Heteroarylboronic Acids with 2-bromoindole Derivatives Cross-coupling of aromatic/heteroaromatic boronic acid or ester derivatives with 2-bromoindoles such as the one described in example 2 can be performed using any variations of the standard metal-catalyzed Suzuki cross-coupling reaction as described in the literature and well known to those skilled in the art. The following example serves to illustrate such a process and is non-limiting.

3-Cyclohexyl-2-furan-3-yl-1H-indole-6-carboxylic acid methyl ester

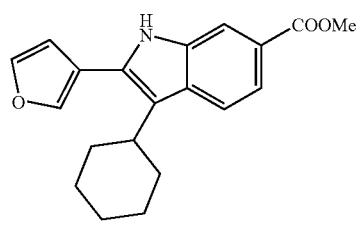

The 2-bromoindole of example 2 (8.92 g, 26.5 mmol), 3-furanboronic acid (B. P. Roques et al. *J. Heterocycl. Chem.* 1975, 12, 195; 4.45 g, 39.79 mmol, 1.5 equivalent) and LiCl (2.25 g, 53 mmol, 2 equivalents) were dissolved in a mixture of EtOH (100 mL) and toluene (100 mL). A 1M aqueous $Na_2CO_3$ solution (66 mL, 66 mmol) was added and the mixture was degassed with argon for 45 min. $Pd(PPh_3)_4$ (3.06 g, 2.65 mmol, 0.1 equivalent) was added and the mixture stirred overnight at 75-85° C. under argon. Volatiles were removed under reduced pressure and the residue re-dissolved in EtOAc (500 mL). The solution was washed with water, saturated $NaHCO_3$ (100 mL) and brine (100 mL). After drying over a mixture of $MgSO_4$ and decolorizing charcoal, the mixture was filtered and concentrated under reduced pressure. The residual oil was triturated with a mixture of TBME (20 mL) and hexane (40 mL), cooled in ice and the precipitated solid collected by filtration, washed with cold 25% TBME in hexane, and dried (3.09 g). The filtrate and washings from the above trituration were combined, concentrated and purified by flash chromatography using 10-25% EtOAc in hexane to give an additional 4.36 g of product. The total yield of the 2-(3-furyl)indole of example 3 was 8.25 g.

Example 4

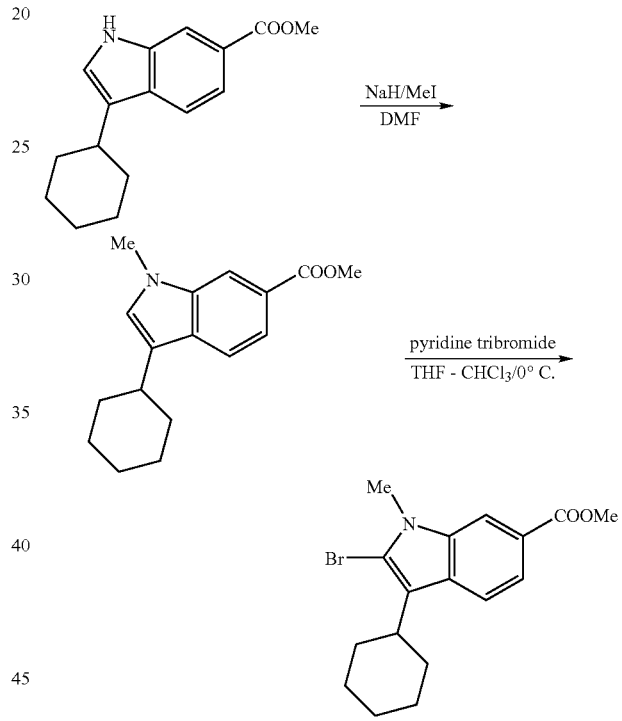

Methyl 3-cyclohexyl-1-methyl-6-indole carboxylate

Methyl 3-cyclohexyl-6-indole carboxylate from example 2 (150.00 g, 0.583 mole) was charged into a 3 L three-necked flask equipped with a mechanical stirrer and purged with nitrogen gas. DMF (1 L) was added and the solution was cooled in an ice-bath. NaH (60% oil dispersion, 30.35 g, 0.759 mole, 1.3 equivalent) was added in small portions (15 min) and the mixture was stirred for 1 h in the cold. Iodomethane (54.5 mL, 0.876 mole, 1.5 equivalent) was added in small portions, maintaining an internal temperature between 5-10° C. The reaction mixture was then stirred overnight at room temperature. The reaction was quenched by pouring into ice-water (3 L), resulting in the formation of a cream-colored precipitate. The material was collected by filtration, washed with water and dried in vacuum at 45° C. (137.3 g, 86% yield).

Methyl 2-bromo-3-cyclohexyl-1-methyl-6-indole carboxylate

The 1-methylindole derivative from above (136.40 g, 0.503 mole) was charged into a 5 L three-necked flask equipped with a mechanical stirrer and purged with nitrogen gas. CHCl$_3$ (750 mL) and THF (750 mL) were added and the solution was cooled to 0° C. Pyridine tribromide (pyridinium bromide perbromide, 185.13 g, 0.579 mole, 1.15 equivalent) was added in small portions and the mixture was stirred for 1 h at 0° C. The solvent was removed under reduced pressure at room temperature and the residue dissolved in EtOAc (3 L). The solution was washed with water and brine, dried (decolourising charcoal/MgSO$_4$) and concentrated under reduced pressure. The residue was suspended in TBME and heated to 50° C. The suspension was stored overnight in the refrigerator and the cream-coloured crystalline product was collected by filtration. It was washed with TBME and dried in vacuum (134.3 g, 76% yield).

Example 5

Cyclohexyl-methyl-tributylstannanyl-1H-indole-6-carboxylic acid methyl ester

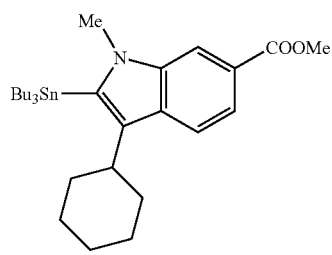

The bromoindole derivative of example 4 (2.70 g, 7.71 mmol) was dissolved in dry THF (40 mL) and the solution was cooled to −78° C. under an argon atmosphere. A solution of nBuLi in hexane (1.4 M, 6.90 mL, 9.64 mmol, 1.25 equivalent) was added dropwise over 15 min and stirring at low temperature was continued for 75 min. To the resulting suspension was added nBu$_3$SnCl (2.93 mL, 10.8 mmol, 1.4 equivalent) over 5 min. The suspension dissolved and the solution was stirred for 1 h at −78° C. The reaction mixture was warmed to room temperature and THF removed under reduced pressure. The residue was dissolved in TBME (150 mL), washed with 1:1 brine-water and dried over MgSO$_4$. The material was purified by chromatography on silica gel that was previously deactivated by mixing with a solution of 5% Et$_3$N in hexane. The same solvent was used as eluent for the chromatography. The title stannane was isolated as a yellow oil (3.42 g, 79% yield).

Example 6

General Procedure for Stille Cross-Coupling of the 2-Stannane Indole of Example 5 with Aromatic/Heteroaromatic Halides Cross-coupling of aromatic/heteroaromatic halides or pseudohalides (preferably bromides, iodides and triflates) with the stannane derivative of example 5 can be performed using any variations of the standard metal-catalyzed Stille cross-coupling reaction as described in the literature. The following example serves to illustrate such a process.

3-Cyclohexyl-1-methyl-2-pyridin-2-yl-1H-indole-6-carboxylic acid methyl ester

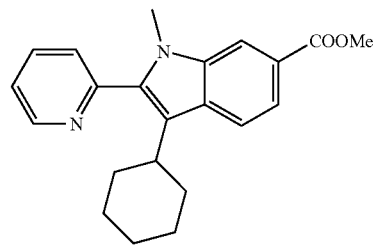

The stannane derivative of example 5 (3.42 g, 6.1 mmol) was dissolved in DMF (10 mL) and CuI (0.116 g, 0.61 mmol, 0.1 equivalent), LiCl (0.517 g, 12.21 mmol, 2 equivalent), triphenylphosphine (0.320 g, 1.22 mmol, 0.2 equivalent) and 2-bromopyridine (0.757 mL, 7.94 mmol, 1.3 equivalent) were added. The solution was degassed with a stream of argon (30 min) and Pd(PPh$_3$)$_4$ (0.352 g, 0.31 mmol, 0.05 equivalent) was added. After purging with argon for an additional 10 min, the solution was heated and stirred at 100° C. overnight under argon. The DMF was then removed under vacuum and the residue dissolved in EtOAc (150 mL). The solution was washed with 1N NaOH (25 mL) and brine (25 mL) and dried over MgSO$_4$. The solvent was removed under reduced pressure and the residue purified by flash chromatography eluting with CHCl$_3$ then 5-10% EtOAc in CHCl$_3$ (1.516 g, 71% yield).

Example 7

General Procedure for Stille Cross-Coupling of 2-bromoindoles with Aryl or Heteroarylstannanes 3-Cyclohexyl-1-methyl-2-pyridin-2-yl-1H-indole-6-carboxylic acid methyl ester

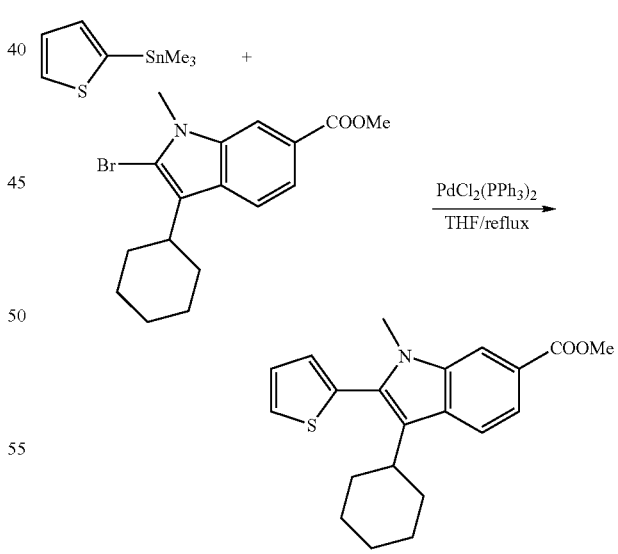

The 2-bromoindole derivative of example 4 (0.150 g, 0.428 mmol) and 2-trimethylstannylthiophene (S. F. Thames et al. J. Organometal. Chem. 1972, 38, 29; 0.150 g, 0.61 mmol, 1.4 equivalent) were dissolved in dry THF (7 mL) in a sealed tube, and the solution was degassed with a stream or argon for 30 min. Pd(Cl)$_2$(PPh$_3$)$_2$ (0.018 g, 0.026 mmol, 0.06 equivalent was added and the tube sealed. The solution was heated to 80° C. for 40 h. The reaction mixture was cooled to room temperature, EtOAc (10 mL) was added and the suspension filtered. After evaporation of the solvent, the residue was re-submitted to the reaction conditions for an additional 20 h, with fresh 2-stannylthiophene (0.150 g, 0.61 mmol) and catalyst (0.020 g). After cooling to room temperature and filtration of solids, the solvent was evaporated and the residue purified by flash chromatography using 15-100% CHCl$_3$ in hexane as eluent (0.133 g, 88% yield).

The same procedure can be used to couple stannane derivatives to the 2-bromoindole of Example 2.

Example 8

General Procedure for the N-alkylation of 2-aryl and 2-heteroaryl-6-indole carboxylates 3-Cyclohexyl-1-methyl-2-pyridin-2-yl-1H-indole-6-carboxylic acid methyl ester

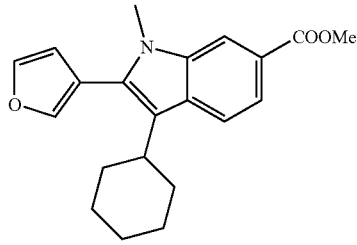

NaH (60% oil dispersion, 0.186 g, 4.64 mmol, 1.5 equivalent) was washed with hexane (20 mL) to remove the oil and then re-suspended in DMF (5 mL). After cooling to 0° C. in an ice bath, the indole derivative of example 3 (1.000 g, 3.09 mmol) was added dropwise as a solution in DMF (3 mL+2 mL rinse). After stirring for 15 min, iodomethane (0.385 mL, 6.18 mmol, 2 equivalents) was added in one portion and the mixture was stirred for 2 h in the cold and an additional 2 h at room temperature. The reaction was then quenched by addition of 1N HCl (1 mL) and diluted with TBME (100 mL). The solution was washed with 1N HCl (25 mL) and dried (MgSO$_4$). After removal of volatiles under reduced pressure, the residue was purified by flash chromatography using 5-10% EtOAc in hexane as eluent to give the title compound as a white solid (0.903 g, 86% yield).

Other N-alkylindole derivatives within the scope of this invention could be prepared from the appropriate electrophiles (e.g. EtI, iPrI, iBuI, BnBr) using a similar procedure.

Example 9

General Procedure for the Saponification of 6-indolecarboxylates to the Corresponding Free Carboxylic Acids This procedure applies to both indole and N-methylindole carboxylates.

3-Cyclohexyl-1-methyl-2-pyridin-2-yl-1H-indole-6-carboxylic acid

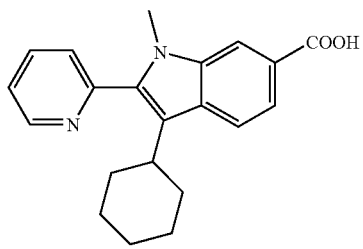

The 6-indole carboxylate of example 6 (1.517 g, 4.35 mmol) was dissolved in DMSO (8 mL) and 5N NaOH (4.4 mL) was added. The mixture was stirred at 50° C. for 30 min. The solution was then cooled to room temperature and added dropwise to water (15 mL). Insoluble black impurities were removed by filtration and AcOH (2 mL) was added dropwise to the filtrate. The white precipitate that formed was collected by filtration, washed with water and dried (1.37 g, 94% yield).

Example 10

1-Cyclohexyl-2-phenyl-1H-indole-5-carboxylic acid

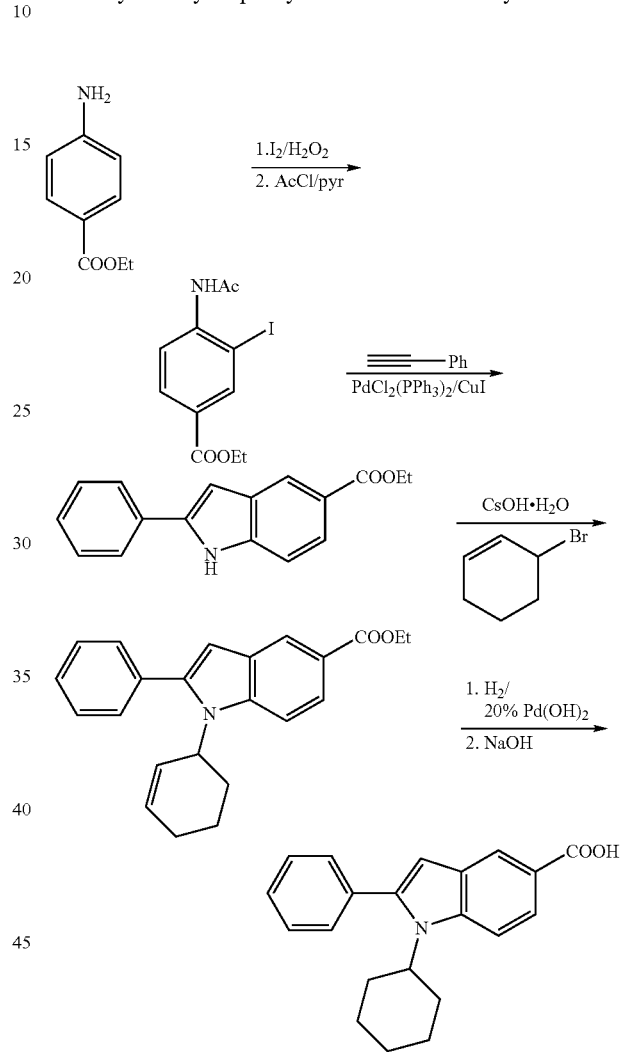

Ethyl 4-amino-3-iodobenzoate

Ethyl 4-aminobenzoate (15.00 g, 91 mmol) and iodine (11.80 g, 46.5 mmol) were mixed with water (80 mL) and chlorobenzene (4.60 g, 41 mmol). The mixture was stirred while the temperature was gradually raised to 90° C. over 30 min. Hydrogen peroxide (30%, 50 mL) was added over 10 h at 90° C. After stirring at that temperature for an additional 6 h, the mixture was cooled and the solution decanted from the residual solids. The solids were dissolved in DCM and the solution washed successively with sodium thiosulfate and brine. After drying (MgSO$_4$), the solvent was removed under reduced pressure and the resulting brown solid was triturated with hexane to remove di-iodinated by-products. The desired compound was obtained as a brown solid (22.85 g, 86% yield).

Ethyl 4-acetamido-3-iodobenzoate

The aniline from above (1.00 g, 3.44 mmol) was dissolved in pyridine (5 mL) and the solution was cooled in ice. AcCl (0.32 mL, 4.47 mmol, 1.3 equivalent) was added dropwise and the mixture was stirred for 1 h at 0° C. and 2 h at room temperature. The reaction mixture was then diluted with 1 N HCl and the product was extracted with TBME (100 mL). The organic phase was washed with 1N HCl (50 mL), dried (MgSO$_4$) and concentrated to give the desired material as a tan-colored solid (1.121 g, 97% yield).

Ethyl 2-phenyl-indole-5-carboxylate

Following the procedure of A. Bedeschi et al. (*Tet. Lett.* 1997, 38, 2307), the acetanilide derivative from above (0.900 g, 2.7 mmol) was reacted with phenylacetylene (0.385 mL, 3.5 mmol, 1.3 equivalent) in the presence of PdCl$_2$(PPh$_3$)$_2$ (10 mole %) and CuI (10 mole %) in a mixture of dioxane (5 mL) and tetramethylguanidine (5 mL). The desired 2-phenylindole (0.589 g, 82% yield) was isolated as a yellow solid after flash chromatography with 15% EtOAc in hexane.

1-Cyclohex-1-enyl-2-phenyl-1H-indole-5-carboxylic acid ethyl ester

The 2-phenylindole derivative from above (0.265 g, 1.0 mmol) was dissolved in DMF (2 mL) and cesium hydroxide monohydrate (0.208 g, 1.2 mmol, 1.2 equivalent) was added. The solution was cooled in an ice bath and 3-bromocyclohexene (0.193 g, 1.2 mmol, 1.2 equivalent) was added dropwise (5 min) as a solution in DMF (1 mL). The mixture was stirred for 30 min at 0° C. The reaction was diluted with water (25 mL), extracted with Et$_2$O (2×50 mL) and the extract dried over MgSO$_4$. The solvent was evaporated under reduced pressure to give a white foam (0.095 g) that was used without purification in the next step.

1-Cyclohexyl-2-phenyl-1H-indole-5-carboxylic acid

The crude indole from above was hydrogenated in the usual way (1 atm H$_2$ gas) in EtOH over 20% Pd(OH)$_2$ on carbon for 20 h at room temperature. After filtration of the catalyst, the EtOH was removed under reduced pressure. The residue was dissolved in a mixture of MeOH (1 mL) and DMSO (1 mL) and 5N NaOH (0.5 mL) was added. The mixture was stirred overnight at 50° C. The reaction mixture was cooled and water (10 mL) was added. After acidification with 1N HCl, the product was extracted into Et$_2$O (70 mL) and the solution dried (Na$_2$SO$_4$). Evaporation of the solvent gave a green residue consisting of a 2:1 mixture (85 mg) of the desired 1-cyclohexyl-2-phenylindole-5-carboxylic acid and 1,3-dicyclohexyl-2-phenylindole-5-carboxylic acid.

Example 11

1-Cyclohexyl-3-methyl-2-phenyl-1H-indole-5-carboxylic acid

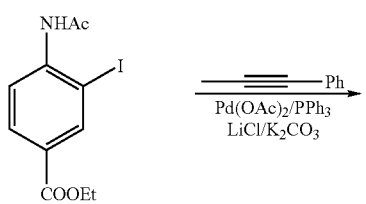

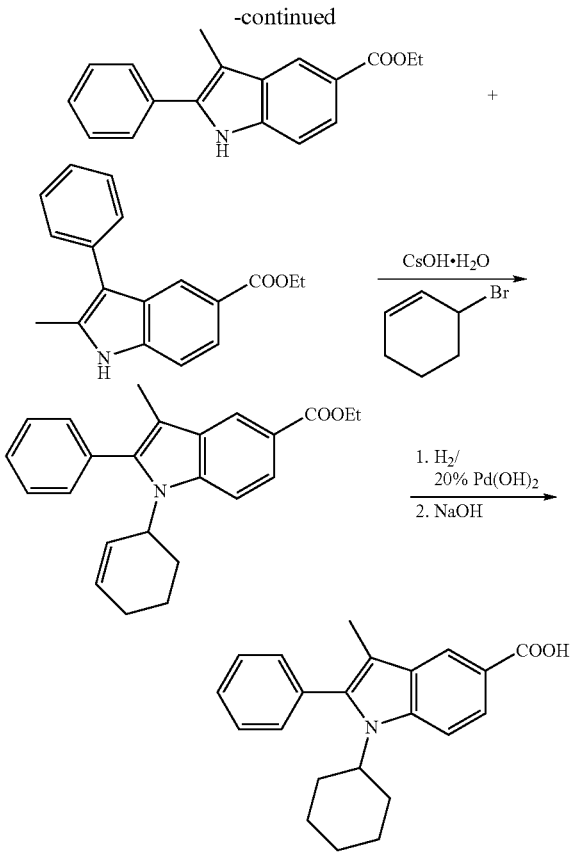

Ethyl 2-phenyl-3-methyl-indole-5-carboxylate

Adapting the procedure of H.-C. Zhang (*Tet. Lett.* 1997, 38, 2439) ethyl 4-amino-3-iodobenzoate (from example 10, 0.500 g, 1.72 mmol) was dissolved in DMF (5 mL) and LiCl (0.073 g, 1.72 mmol, 1 equivalent), PPh$_3$ (0.090 g, 0.34 mmol, 0.2 equivalent), K$_2$CO$_3$ (1.188 g, 8.6 mmol, 5 equivalents) and phenylpropyne (0.645 mL, 5.76 mmol, 3 equivalents) were added. The solution was degassed by purging with argon for 1 h and palladium acetate (0.039 g, 0.17 mmol, 0.1 equivalent) was added. The mixture was stirred at 80° C. under argon for 20 h. The reaction mixture was diluted with water (25 mL) and extracted with EtOAc (50 mL). The extract was washed with brine (3×25 mL) and dried (MgSO$_4$). Concentration under reduced pressure and purification by flash chromatography with 10-15% EtOAc-hexane gave the desired 2-phenyl-3-methyl indole (0.275 g, least polar component) and the 3-phenyl-2-methyl isomer (0.109 g, more polar component).

Ethyl 1-(3-cyclohexenyl)-3-methyl-2-phenylindole-5-carboxylate

The less polar isomer from above (0.264 g, 0.95 mmol) was dissolved in DMSO (2 mL) and cesium hydroxide monohydrate (0.191 g, 1.14 mmol, 1.2 equivalent) was added followed by 3-bromocyclohexene (0.183 g, 1.14 mmol, 1.2 equivalent in 0.7 mL of DMSO). The mixture was stirred at room temperature for 30 min. Additional CsOH monohydrate (0.400 g, 2.4 equivalents) and 3-bromocyclohexene (0.400 g, 2.4 equivalents) were added and stirring continued for an additional 30 min. Similar amounts of the two reagents were again added and after another 30 min of stirring at room temperature, the reaction was diluted with 1N HCl (6 mL) and water (20 mL). The product was extracted with TBME (100 mL), dried (MgSO₄) and after concentration under reduced pressure, the residue was purified by flash chromatography using 5-10% EtOAc in hexane as eluent. The desired N-alkylated indole was obtained (0.130 g).

Ethyl 1-cyclohexyl-3-methyl-2-phenylindole-5-carboxylate

The unsaturated product from above was hydrogenated (1 atm H₂ gas) in the usual way over 20% Pd(OH)₂ in EtOH at room temperature for 3 h.

1-Cyclohexyl-3-methyl-2-phenyl-1H-indole-5-carboxylic acid

The hydrogenated material from above was dissolved in a mixture of DMSO (2 mL) and MeOH (2 mL). 5N NaOH (0.5 mL) was added and the mixture was stirred overnight at 60° C. After dilution with water (40 mL), the product aqueous phase was washed with a 1:1 mixture of Et₂O-hexane (50 mL) and then acidified with 1N HCl to pH 1. The liberated free acid was extracted with diethyl ether (2×50 mL) and the extract dried over Na₂SO₄. Removal of the solvent under reduced pressure gave the desired indole as a light brown solid (0.074 g).

Example 12

2-Bromo-3-cyclopentyl-1-methyl-1H-indole-6-carboxylic acid methyl ester

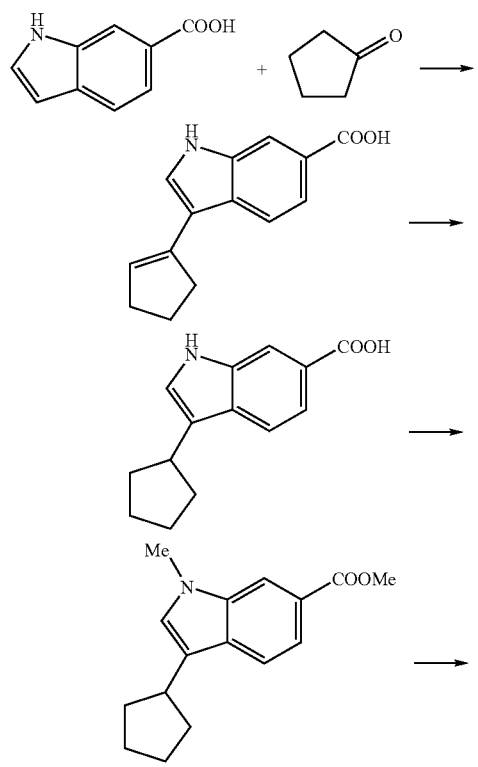

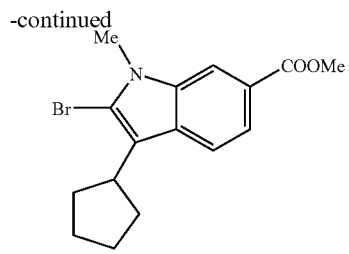

A 3 L three-necked flask equipped with a mechanical stirrer was charged with indole 6-carboxylic acid (220 g, 1.365 mole) and KOH pellets (764.45 g, 13.65 mole, 10 equivalents). Water (660 mL) and MeOH (660 mL) were added and the mixture heated to 75° C. Cyclopentanone (603.7 mL, 6.825 mole, 5 equivalents) was added dropwise over 18 h using a pump. The reaction mixture was heated for an additional 3 h (after which the reaction was judged complete by HPLC) and cooled to 0° C. for 1 h. The precipitated potassium salt is collected by filtration, and washed with TBME (2×500 mL) to remove cyclopentanone self-condensation products. The brown solid was re-dissolved in water (2.5 L) and the solution washed with TBME (2×1 L). Following acidification to pH 3 with conc. HCl (425 mL), the beige precipitate was collected by filtration, washed with water (2×1 L) and dried under vacuum at 70° C. The crude product weighed 275.9 g (88.9% mass recovery) and had an homogeneity of 85% (HPLC).

The crude product from above (159.56 g, 0.70 mole) was dissolved in MeOH (750 mL) and 20% Pd(OH)₂ on charcoal (8.00 g) was added. The mixture was hydrogenated in a Parr apparatus under 50 psi hydrogen gas for 18 h. After completion, the catalyst was removed by filtration through celite and the solvent removed under reduced pressure. The resulting brown solid was dried at 70° C. under vacuum for 12 h. The crude product (153.2 g) was obtained as a brown solid and was 77% homogeneous by HPLC.

The crude 3-cyclopentylindole-6-carboxylic acid (74.00 g, 0.323 mole) was charged in a 3 L three-necked flask equipped with a mechanical stirrer and a thermometer. The system was purged with nitrogen gas and anhydrous DMF (740 mL) was added. After dissolution on the starting material, anhydrous potassium carbonate (66.91 g, 0.484 mole, 1.5 equivalent) was added and the mixture stirred for 5 minutes. Iodomethane (50 mL, 0.807 mole, 2.5 equivalents) was added and the mixture stirred for 5 h after which HPLC analysis of the reaction mixture indicated 97% conversion to the methyl ester.

The reaction mixture was cooled in an ice bath and sodium hydride (95%, oil-free, 10.10 g, 0.420 mole, 1.3 equivalent) was added in small portions over 3 min (exothermic: 8° C. to 30° C. internal temperature raise). After stirring for an additional 15 min, the cooling bath was removed and stirring continued for 1.5 h at room temperature after which no further progression was observed (HPLC). Additional NaH (1.55 g, 65 mmol, 0.2 equivalent) and iodomethane (1.0 mL, 16 mmol, 0.05 equivalent) were added and after stirring for 15 min, the reaction was judged complete by HPLC (96% N-methylated).

The reaction mixture was slowly (2 min) poured into water (4 L) with vigorous stirring and after 10 min, acidified to pH<2 with conc. HCl (85 mL). The mixture was stirred for 5 min to allow complete conversion of any remaining potassium carbonate and bicarbonate to the more soluble chloride. The pH was adjusted to ~7 with 4N NaOH (40 mL) and the mixture stirred overnight at room temperature. The precipitated material was collected by filtration, washed with water (600 mL) and dried at 60° C. under vacuum. The crude product (79% homogeneity by HPLC) was obtained as a brown solid (72.9 g).

The crude material from above is triturated with a minimal amount of MeOH to remove a series of minor impurities. The solid was then collected by filtration and dissolved in a minimal amount of hot EtOAc. After cooling to room temperature, hexane was added (5× volume) and the mixture cooled in ice and filtered. The filtrate was then evaporated to dryness to give the desired product.

The N-methylindole from above (10.60 g, 41.2 mmol) was dissolved in isopropyl acetate (150 mL) and sodium acetate (5.07 g, 62 mmol, 1.5 equivalent) was added. The suspension was cooled in an ice bath and bromine (2.217 mL, 43.3 mmol, 1.05 equivalent) was added dropwise over 2 min. The pale amber suspension turned dark red (exotherm from 5° C. to 13° C.). It was stirred for 1 h at 0° C. The reaction was completed by adding additional bromine (0.21 mL, 4.2 mmol, 0.10 equivalent) as shown by HPLC analysis. The reaction was then quenched by addition of 10% aqueous sodium sulfite solution (15 mL), followed by water (50 mL) and $K_2CO_3$ (10.6 g, 1.8 equivalent) to neutralize HBr. The organic layer was separated, washed with 10% aqueous sodium sulfite and aqueous $K_2CO_3$ and dried ($MgSO_4$). The solvent was removed under reduced pressure and the residue co-evaporated with TBME (75 mL) to give a beige solid that was dried under vacuum overnight (13.80 g). The crude material was triturated with boiling MeOH (80 mL) for 30 min, cooled in ice and the beige solid collected by filtration. The product was dried at 60° C. under vacuum (10.53 g, 76% recovery).

Example 13

3-Cyclopentyl-1-methyl-2-vinyl-1H-indole-6-carboxylic acid

To the 2-bromoindole derivative of example 12 (2.044 g, 6.08 mmol) in dry dioxane (20 mL) was added vinyltributyltin (1.954 mL, 6.69 mmol). The solution was degassed by bubbling nitrogen for 15 min. Then bis(triphenylphosphine) palladium (II) chloride (213.4 mg, 0.304 mmol) was added and the reaction mixture was heated at 100° C. overnight. The reaction mixture was diluted with ether and successively washed with water and brine. After the usual treatment ($MgSO_4$, filtration and concentration) the residue was flash chromatographed (5 cm, 10% AcOEt-hexane) to afford the desired compound (1.32 g, 4.70 mmol, 77% yield) as a white solid.

To the ester from above (153 mg, 0.54 mmol) in a mixture of THF (2.8 mL) and methanol (1.4 mL) was added an aqueous solution of lithium hydroxide (226.6 mg, 5.40 mmol in 1.6 mL of water). The reaction mixture was stirred at 50° C. for 1.5 h and diluted with water. The aqueous layer was acidified with 1M aq. HCl and extracted three times with $CH_2Cl_2$. The combined organic layers were successively washed with water (2×) and brine. After the usual treatment ($MgSO_4$, filtration and concentration) the desired crude acid was isolated (150 mg).

Example 14

3-Cyclohexyl-1-methyl-2-oxazol-5-yl-1H-indole-6-carboxylic acid

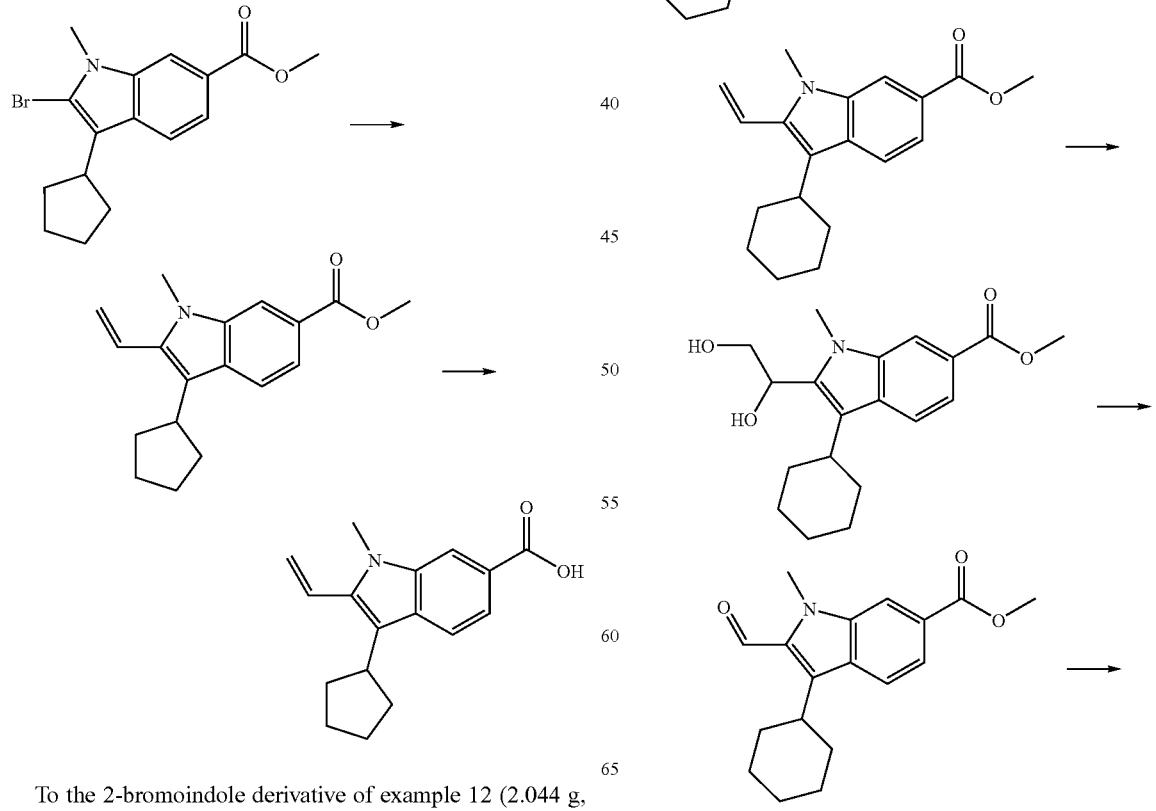

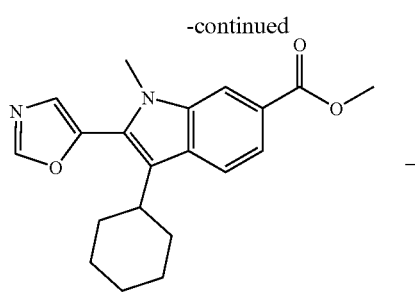
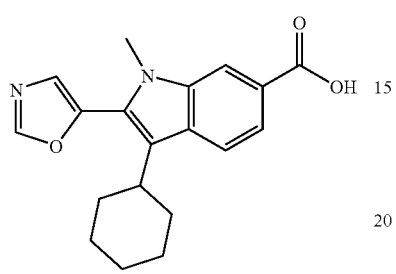

To the bromide of example 4 (1.00 g, 2.855 mmol) in dry dioxane (10 mL) was added vinyltributyltin (917.8 µL, 3.141 mmol). The solution was degassed by bubbling nitrogen through for 15 min. Then bis(triphenylphosphine) palladium (II) chloride (101 mg, 0.144 mmol) was added and the solution was refluxed for 7 hrs. The reaction mixture was diluted with ether and successively washed with water and brine. After the usual treatment (MgSO₄, filtration and concentration) the residue was flash chromatographed (5 cm, hexane to 2.5% AcOEt to 5% AcOEt to 10% AcOEt-hexane) to afford the desired compound (773 mg, 2.60 mmol, 91% yield) as a pale yellow solid.

To the olefinic derivative from above (100 mg, 0.336 mmol) in a mixture of acetone (690 µL), tert-butanol (690 µL) and water (690 µL) were successively added N-methylmorpholine N-oxide (NMMO; 48 mg, 0.410 mmol) and a 2.5% solution of osmium tetroxide in tert-butanol (33 µL). The reaction mixture was stirred at room temperature for three days and then concentrated. The residue was dissolved in EtOAc and successively washed with water (2×) and brine. After the usual treatment (MgSO₄, filtration and concentration) the crude diol (117 mg) was isolated.

To the crude diol obtained above (ca. 0.336 mmol) in a mixture of THF (3.2 mL) and water (3.2 mL) at 0° C. was added sodium periodate (86.2 mg, 0.403 mmol). The cooling bath was then removed and the reaction mixture was stirred at room temperature for 1 h 45 min. AcOEt was then added. The resulting solution was successively washed with 10% aq. citric acid, water, satd aq. NaHCO₃, water (2×) and brine. After the usual treatment (MgSO₄, filtration and concentration) the crude desired aldehyde was isolated (92 mg, 0.307 mmol, 91% yield).

A mixture of the aldehyde from above (25.8 mg, 0.086 mmol), anhydrous potassium carbonate (12.4 mg, 0.090 mmol) and Tosmic (17.57 mg, 0.090 mmol) in absolute MeOH (500 µL) was refluxed for 2 h. AcOEt was then added and the mixture was successively washed with water (2×) and brine. After the usual treatment (MgSO₄, filtration and concentration) the crude desired oxazole was isolated (28 mg, 0.083 mmol, 96% yield).

To the ester from above (28 mg, 0.083 mmol) in a mixture of THF (425 µL), MeOH (210 µL) and water (250 µL) was added lithium hydroxide (34.8 mg, 0.830 mmol). The reaction mixture was stirred overnight at room temperature, then diluted with water and acidified with a 1N aq. HCl solution. The aqueous layer was extracted with dichloromethane (3×) and successively washed with water (2×) and brine. After the usual treatment (MgSO₄, filtration and concentration) the title crude acid was isolated (30 mg).

Example 15

2-(1H-Benzimidazol-2-yl)-3-cyclohexyl-1-methyl-1H-indole-6-carboxylic acid

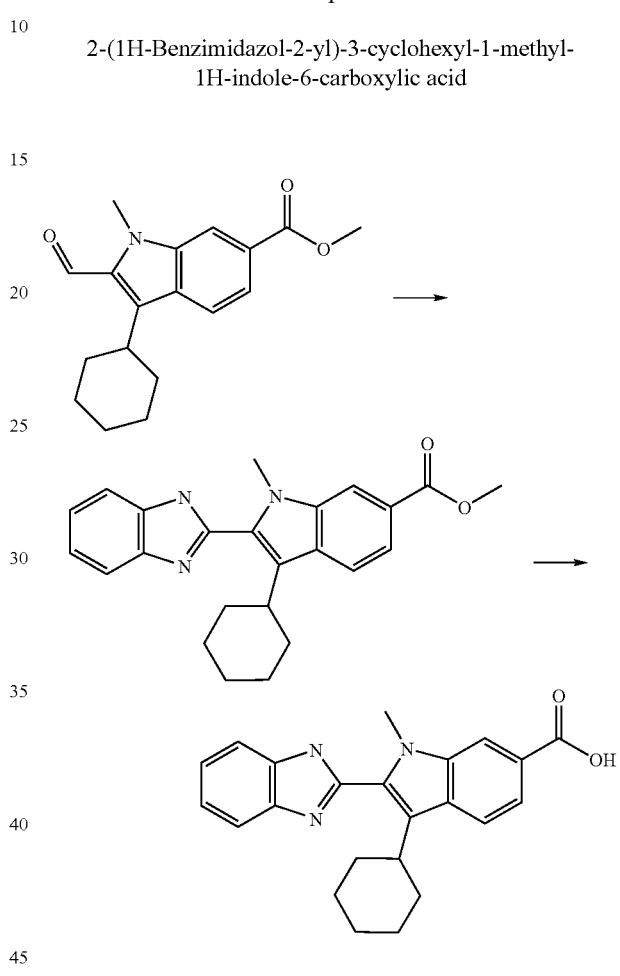

To a mixture of the aldehyde from example 14 (28 mg, 0.094 mmol) and 1,2-diaminobenzene (10.9 mg, 0.101 mmol) in acetonitrile (500 µL) and DMF (200 µL) was added chloranil (24.8 mg, 0.101 mmol). The reaction mixture was stirred at room temperature for three days. AcOEt was added and the reaction mixture was successively washed with a 1N aq. NaOH solution (2×), water (4×) and brine. After the usual treatment (MgSO₄, filtration and concentration) the residue was flash chromatographed (1 cm, 30% AcOEt-hexane) to afford the desired benzimidazole ester derivative (11 mg, 0.028 mmol, 30% yield).

To the ester from above (11 mg, 0.028 mmol) in a mixture of THF (240 µL), MeOH (120 µL) and water (140 µL) was added lithium hydroxide (11.7 mg, 0.280 mmol). The reaction mixture was stirred overnight at room temperature, then diluted with water and acidified with a 1N aq. HCl solution. The aqueous layer was extracted with dichloromethane (3×) and successively washed with water (2×) and brine. After the usual treatment (MgSO₄, filtration and concentration) the title crude acid was isolated (9 mg, 0.0241 mmol, 86% yield).

Example 16

3-Cyclopentyl-1-methyl-1H-indole-2,6-dicarboxylic acid 6-methyl ester

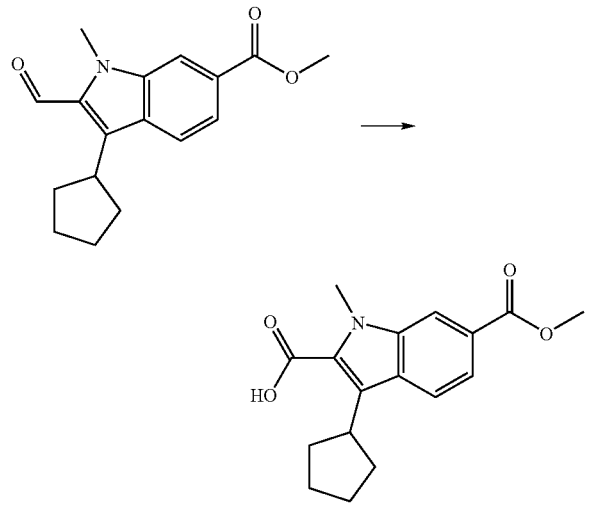

To the 3-cyclopentyl aldehyde prepared in a similar fashion to that described in example 15 (20 mg. 0.07 mmol) and 2-methyl-2-butene (541 µL, 5.11 mmol) in tert-butanol (500 µL) at 0° C. was added a freshly prepared solution of sodium chlorite (64.2 mg, 0.711 mmol) in phosphate buffer (98 mg of NaH$_2$PO$_4$ in 150 µL of water). The reaction mixture was stirred for 45 min. at room temperature then brine was added. The aqueous layer was extracted twice with EtOAc. The combined organic layer was successively washed with a 0.5 N aq. HCl solution and brine. After the usual treatment (MgSO$_4$, filtration and concentration) 23.1 mg of the desired crude acid were isolated as a yellow solid.

Example 18

3-Cyclopentyl-2-pyridin-2-yl-benzofuran-6-carboxylic acid

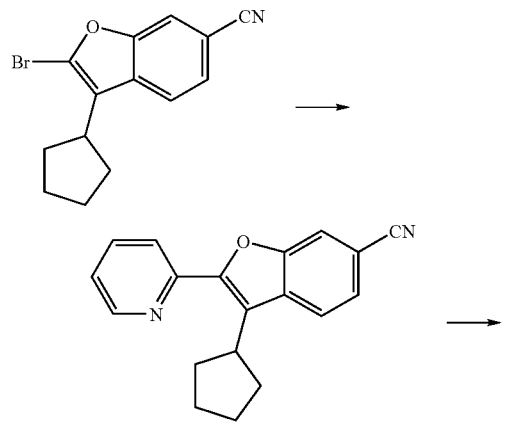

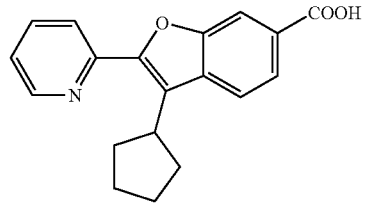

The 2-bromobenzofuran derivative of example 17 (0.850 g, 2.93 mmol), 2-tri(n-butyl)stannylpyridine (1.362 g, 3.7 mmol), triphenylphosphine (0.760 g, 2.90 mmol), lithium chloride (0.250 g, 5.9 mmol) and CuI (0.057 g, 0.3 mmol) were dissolved in DMF (30 mL) and the mixture was degassed by bubbling argon for 30 min. Tetrakis(triphenylphosphine)palladium (0.208 g, 0.18 mmol) was added and the mixture stirred at 100° C. under an argon atmosphere. After 19 h, the reaction was cooled to room temperature, poured into water (70 mL) and extracted with TBME. The organic phase was washed with water (2×) and brine, dried (MgSO$_4$) and concentrated to give a residue that was purified by flash chromatography. The desired 2(2-pyridyl)benzofuran derivative (0.536 g, 63% yield) was obtained as a white solid.

The nitrile from above (0.200 g, 0.694 mmol) was suspended in a mixture of conc. H$_2$SO$_4$ (5 mL), AcOH (4 mL) and water (2 mL). After refluxing for 1.5 h, TLC showed complete hydrolysis. The mixture was cooled in ice and the 10 N NaOH was added dropwise to pH 9. The aqueous layer was washed with dichloromethane and then acidified to pH 6 with 5 N HCl. The product was extracted with EtOAc, dried (MgSO$_4$) and solvents removed under reduced pressure. The desired carboxylic acid was obtained as a white solid.

Example 19

2-Bromo-3-cyclopentyl-benzo[b]thiophene-6-carboxylic acid ethyl ester

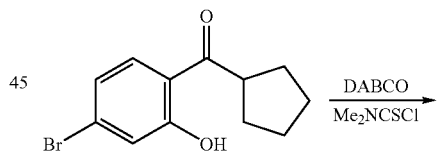

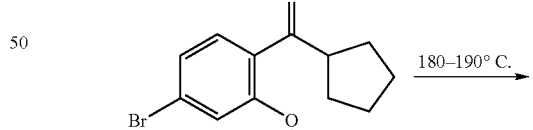

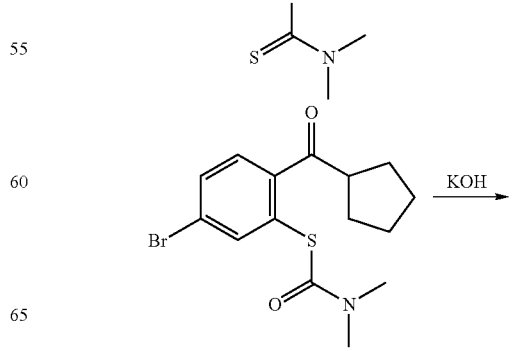

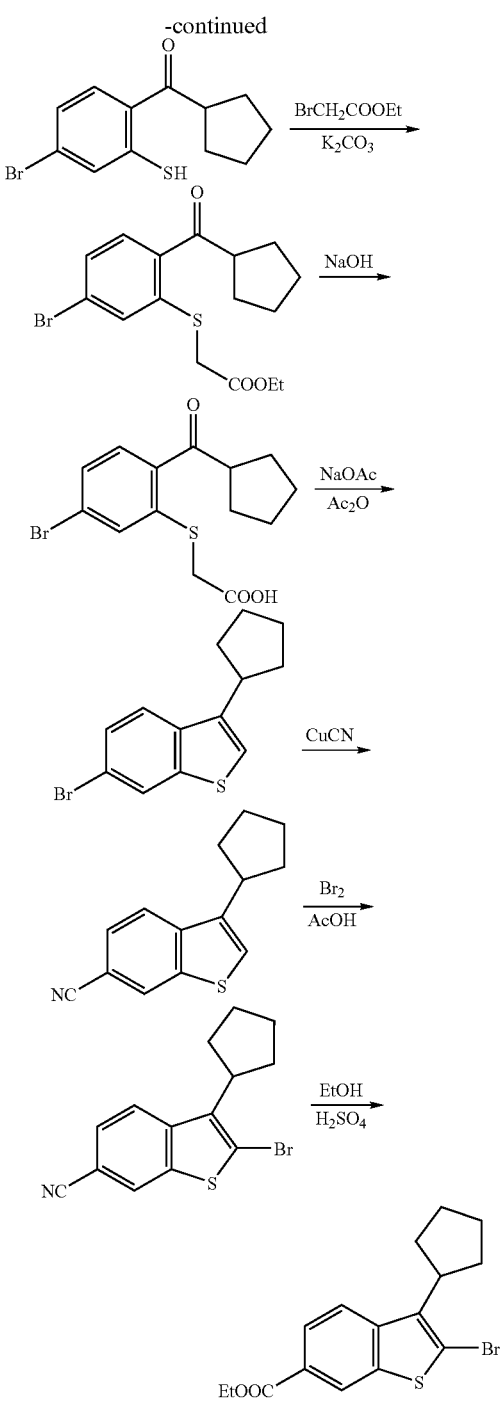

-continued

To a solution of 3-bromo-6-cyclopentanecarbonylphenol of Example 17 (5.194 g, 19.30 mmol) in DMF (58.0 mL) was added 1,4-diazabicyclo[2.2.2]octane (4.33 g, 38.60 mmol) and dimethylthiocarbamyl chloride (4.77 g, 38.6 mmol) at room temperature. The mixture was stirred at room temperature for 3 hr. The mixture was acidified with 1 N HCl to pH 3 and then extracted with EtOAc. The organic layers were combined and washed with brine and dried over $MgSO_4$. The crude mixture was purified through a plug of silica gel with 3% EtOAc/hexanes to provide 6.976 g (100%) of the desired thiocarbamate as a colorless oil.

The neat O-3-bromo-6-cyclopentanecarbonyl N,N-dimethylthiocarbamate from above (43.147 g, 121.1 mmol) was heated to internal temperature of 180-190° C. for 5 hr. TLC (20% EtOAc/hexanes: $R_f$ 0.6 (starting material), 0.5 (product)) was used to monitor the reaction progress. The crude material was used for the next reaction without further purification.

The crude S-3-bromo-6-cyclopentanecarbonyl N,N-dimethylthiocarbamate from above was dissolved in MeOH (600 mL), KOH (40.0 g, 714 mmol) was added and the mixture was heated to reflux for 1.5 h. The mixture was cooled to room temperature and the solvent was removed by rotary evaporation. The residue was dissolved in water and acidified by 6 N HCl to pH 3. It was extracted with EtOAc and the crude product was purified by a silica gel chromatography with 1-5% EtOAc/hexanes. 31.3 g (91%) of the desired thiophenol derivative was obtained as a yellow oil.

To a solution of the 3-bromo-6-cyclopentanecarbonylthiophenol from above (0.314 g, 1.105 mmol) in acetone (5.0 mL) was added $K_2CO_3$ (0.477 g, 3.45 mmol) followed by addition of ethyl bromoacetate (0.221 g, 0.147 mL, 1.33 mmol). The mixture was stirred overnight. The reaction mixture was filtered through filter paper and the filtrate was concentrated. Purification by silica gel with 5% EtOAc/hexanes provided 0.334 g (82%) of the product as a colorless oil. The crude ester from above was dissolved in THF (12.0 mL), 1 N NaOH (5.0 mL) was added at room temperature. The mixture was stirred at room temperature for 2-3 hr. or until TLC indicated complete reaction. The solvent was removed by rotary evaporation. Water was added and the mixture was acidified with 6 N HCl to pH 3 and extracted with EtOAc, washed with brine and dried over $MgSO_4$. The solvent was removed under reduced pressure and the residue was used without further purification.

To the crude acid from above was added acetic anhydride (16.0 mL), and then NaOAc (0.573 g) and the mixture was heated to reflux overnight. The mixture was cooled to room temperature and poured into a mixture of ice and toluene. 6 N NaOH was added until pH to about 7, and extracted with EtOAc, washed with brine and dried over $MgSO_4$. The solvent was removed by rotary evaporation and the residue was purified by silica gel with hexanes to provide 0.795 g (80%) of 6-bromo-3-cyclopentyl benzothiophene as a colorless oil.

A mixture of the 6-bromo-3-cyclopentylbenzothiophene from above (0.723 g, 2.57 mmol), and copper cyanide (0.272 g, 3.04 mmol) in DMF (1.4 mL) was heated to reflux overnight. The mixture was cooled to room temperature and diluted with EtOAc. 2 N $NH_4OH$ was added and the mixture was stirred for 10 minutes and filtered through Celite. The aqueous layer was extracted with EtOAc. The organic layers were combined and washed with brine, dried over $MgSO_4$, and the solvent was removed under reduced pressure. The product was used without further purification.

3-cyclopentyl-6-cyanobenzothiophene (17.65 g, 77.65 mmol) was dissolved in acetic acid (310 mL), bromine (49.64 g, 310.6 mmol) was added at room temperature. The mixture was stirred at room temperature overnight and HPLC was used to monitor the reaction progress. After the reaction was complete, toluene was added to the reaction mixture to remove acetic acid (3×100 mL). The crude product was dried under reduced pressure and used without further purification.

The crude cyano derivative from above was added to ethanol (150 mL, denatured) and conc. $H_2SO_4$ (45 mL) and the mixture heated to reflux for 1-2 days. After completion (HPLC) the reaction mixture was cooled to room temperature and poured into ice-water and extracted with dichloromethane (5×100 mL), the organic layers were combined and washed with 5% $NaHCO_3$, and brine. The solvent was removed under reduced pressure and the residue was purified with silica gel by 1% EtOAc/hexanes. The collected fractions were concentrated and the residue was slurried in methanol.

The solid was filtered and washed with ice-cold methanol to provide 15.9 g (58%, two steps) of pure ethyl ester as a slight yellow solid.

Example 20

3-Cyclopentyl-2-pyridin-2-yl-benzo[b]thiophene-6-carboxylic acid

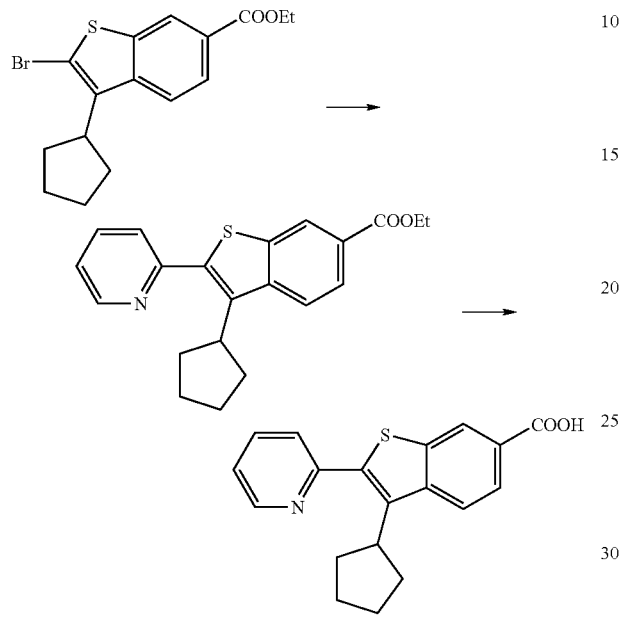

The 2-bromobenzothiophene of example 19 (0.354 g, 1.00 mmol), 2-tri(n-butyl)stannylpyridine (0.442 g, 1.2 mmol), triphenylphosphine (0.262 g, 1.00 mmol), lithium chloride (0.085 g, 2.0 mmol) and CuI (0.019 g, 0.1 mmol) were dissolved in DMF (10 mL) and the mixture was degassed by bubbling argon for 30 min. Tetrakis(triphenylphosphine)palladium (0.069 g, 0.06 mmol) was added and the mixture stirred at 100° C. under an argon atmosphere. After 24 h, the reaction was cooled to room temperature, poured into water (70 mL) and extracted with TBME. The organic phase was washed with water (2×) and brine, dried (MgSO$_4$) and concentrated to give a residue that was purified by flash chromatography. The desired 2(2-pyridyl)benzothiophene ester (0.197 g, 56% yield) was obtained as a pale yellow waxy solid.

The ester from above was hydrolyzed in the usual manner using NaOH, to give the title acid that could be used directly or purified by HPLC and flash chromatography.

The acid could be coupled to amine derivatives following the general procedure described in example 37.

Example 21

3-Cyclopentyl-2-furan-3-yl-benzo[b]thiophene-6-carboxylic acid

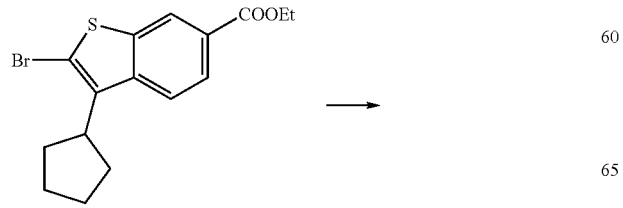

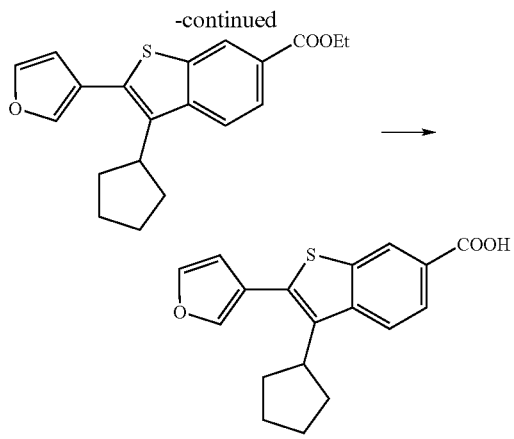

The 2-bromobenzothiophene ester of example 19 was coupled to 3-furanboronic acid as described in example 3 to give the desired 2(3-furyl)benzothiophene ester in 85% yield. Saponification of the ethyl ester was carried out with NaOH at room temperature to give the title carboxylic acid derivative.

Example 22

3-Cyclohexyl-1-methyl-2-phenyl-1H-pyrrolo[2,3,b]pyridine-6-carboxylic acid

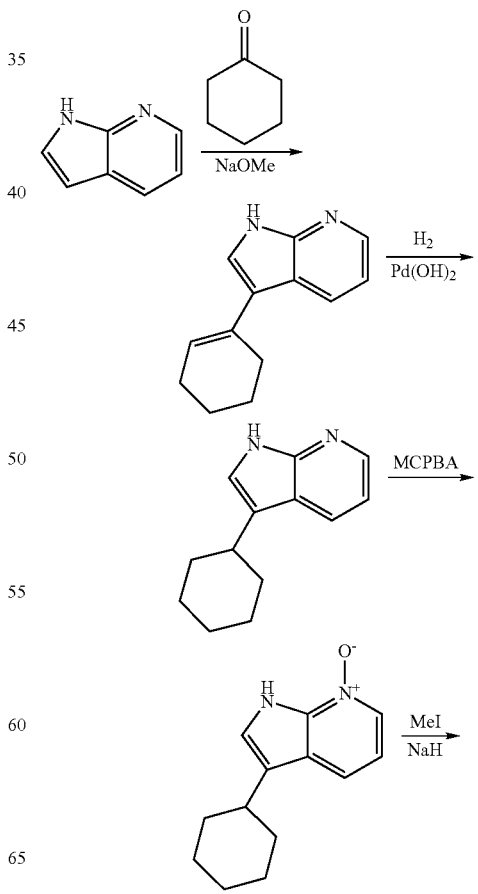

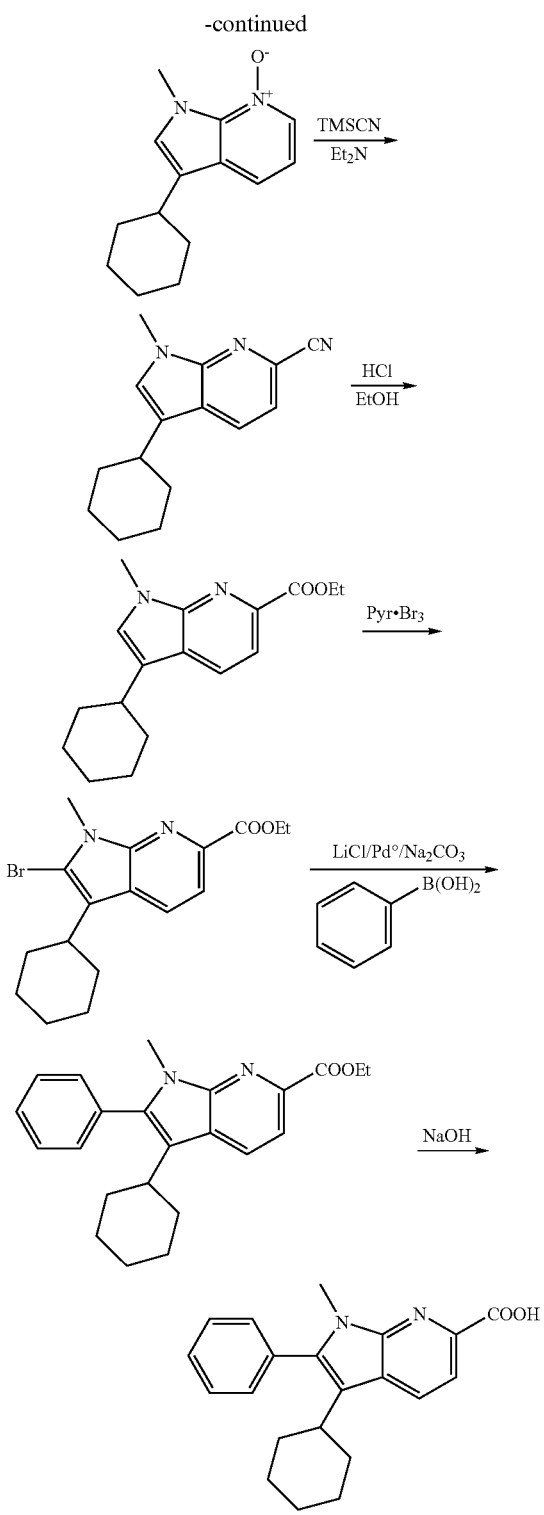

7-Azaindole (15.00 g, 0.127 mole) was dissolved in MeOH (330 mL) and sodium methoxide (25% w/w in MeOH, 172 mL, 0.753 mole) and cyclohexanone (52.86 mL, 0.51 mole) were added. The mixture was refluxed for 60 h and then concentrated under reduced pressure. After cooling in ice-water, the reaction mixture was acidified to pH 8 with 3N HCl and the precipitated solid was collected by filtration. The product was washed with water, triturated with TBME-hexane and dried by azeotroping with toluene (19.8 g).

The material from above (15.00 g, 75.65 mmol) was dissolved in a mixture of EtOH (130 mL) and THF (30 mL) and 20% Pd(OH)$_2$ on carbon (1.30 g) was added. The mixture was hydrogenated under 1 atm of H$_2$ gas for 24 h, after which point additional catalyst (1.30 g) was added. After stirring under H$_2$ gas for an additional 16 h, the catalyst was removed by filtration and the solution evaporated under reduced pressure to give a residue that was triturated with TBME to give an amber solid (13.9 g).

The azaindole derivative from above (7.50 g, 37.45 mmol) was dissolved in DME (130 mL) and meta-chloroperbenzoic acid (12.943 g, 60.0 mmol) was added. After stirring for 2 h, volatiles were removed under reduced pressure and the residue suspended in water (100 mL). The mixture was basified to pH 10 by addition of saturated aqueous Na$_2$CO$_3$ solution under vigorous stirring. The solid was then collected by filtration, washed with water and a small amount of TBME, and dried (7.90 g).

The crude N-oxide from above (4.00 g, 18.49 mmol) was dissolved in DMF (350 mL) and NaH (60% dispersion, 1.52 g, 38 mmol) was added in small portions over 5 min. The mixture was stirred for 30 min and iodomethane (1.183 mL, 19 mmol) was added dropwise over 20 min to the suspension. After stirring for 3 h at room temperature, no more progress was measured by HPLC analysis. The reaction mixture was poured into water and extracted 3 times with EtOAc. The extract was washed with brine, dried (MgSO$_4$) and evaporated to give an amber solid (3.65 g, 60% homogeneity by NMR) that was used immediately without purification.

The crude product from above (0.80 g, 3.47 mmol) was dissolved in MeCN (10 mL). Triethylamine (1.13 mL, 8.1 mmol) was added followed by trimethylsilyl cyanide (2.13 mL, 16 mmol). The solution was then refluxed for 19 h. After cooling to room temperature, the reaction was quenched by slow addition of aqueous NaHCO$_3$ and the product extracted with EtOAc. The extract was washed with brine, dried (MgSO$_4$) and concentrated to a residue that was purified by flash chromatography on silica gel using 15% EtOAc-hexane (0.285 g). The nitrile (0.300 g, 1.254 mmol) was suspended in EtOH (15 mL) and hydrogen chloride gas was bubbled through for 15 min to give a clear solution. The solution was then refluxed for 1.5 h until TLC showed complete conversion of starting material. After cooling to room temperature, volatiles were removed under reduced pressure and the residue was dissolved in EtOAc. The solution was washed with brine, dried (MgSO$_4$) and concentrated. The residue was purified by flash chromatography on silica gel (15-20% EtOAc-hexane) to give the desired ethyl ester as a pale yellow gum (0.227 g).

The ester from above (0.100 g, 0.35 mmol) was dissolved in THF (4 mL) and pyridinium hydrobromide perbromide (0.200 g, 0.532 mmol) was added. The mixture was stirred at 65° C. in a sealed vial for 16 h (>80% conversion). The solution was evaporated and the residue taken up into EtOAc. The solution was washed with water and brine, dried (MgSO$_4$) and concentrated. The crude material was purified by flash chromatography on silica gel (15% EtOAc-hexane). The bromide from above (0.100 g, 0.274 mmol), phenylboronic acid (0.049 g, 0.4 mmol) and lithium chloride (0.019 g, 0.45 mmol) were dissolved in a mixture of toluene (2 mL), EtOH (2 mL) and 1M Na$_2$CO$_3$ (0.43 mL). The mixture was degassed by passing argon gas through the solution for 30 min, and tetrakistriphenylphosphine palladium (0.035 g, 0.03 mmol) was added. The mixture was refluxed for 18 h after which point more catalyst (0.035 g, 0.03 mmol) was added. After refluxing for an additional 2 h, the EtOH was removed under reduced pressure. The residue was dissolved in EtOAc and the solution washed with 10% aqueous HCl and brine, and dried (MgSO$_4$). Removal of volatiles under reduced pressure gave an orange gum that was purified by flash chromatography on silica gel using 20% EtOAc-hexane (0.105 g, crude).

The partially purified ester from above (0.100 g, 0.276 mmol) was dissolved in a mixture of THF (2 mL) and EtOH (2 mL). 1N NaOH (2.8 mL) was added and the mixture stirred for 4 h at room temperature. Volatiles were removed under reduced pressure and the residue diluted with 10% aqueous HCl. The product was extracted with EtOAc (3×), dried (MgSO$_4$), evaporated and purified by reversed-phase preparative HPLC to give the title compound.

Example 23

Inhibition of NS5B RNA Dependent RNA Polymerase Activity

The compounds of the invention were tested for inhibitory activity against the hepatitis C virus RNA dependant polymerase (NS5B), according to the following assay:

The substrates are:

a 12 nucleotide RNA oligo-uridylate (or oligo-uridine-monophosphate) (oligo-U) primer modified with biotin at the free 5° C. position;

a complementary poly-adenylate (or adenosine monophosphate) (polyA) template of heterogeneous length (1000-10000 nucleotides); and UTP-[5,6 $^3$H].

Polymerase activity is measured as the incorporation of UMP-[5,6 $^3$H] into the chain elongated from the oligo-U primer. The $^3$H-labelled reaction product is captured by SPA-beads coated with streptavidin and quantified on the Top-Count.

All solutions were made from DEPC treated MilliQ water [2 ml of DEPC is added to 1 L of MilliQ water; the mixture is shaken vigorously to dissolve the DEPC, then autoclaved at 121° C. for 30 minutes].

Enzyme: The full length HCV NS5B (SEQ ID NO. 1) was purified as an N-terminal hexa-histidine fusion protein from baculovirus infected insect cells. The enzyme can be stored at −20° C. in storage buffer (see below). Under these conditions, it was found to maintain activity for at least 6 months.

Substrates: The biotinylated oligo-U$_{12}$ primer, the Poly(A) template, and the UTP-[5,6 $^3$H] were dissolved in water. The solutions can be stored at −80° C.

| Assay buffer: | 20 mM Tris-HCl pH 7.5 |
| --- | --- |
| | 5 mM MgCl$_2$ |
| | 25 mM KCl |
| | 1 mM EDTA |
| | 1 mM DTT |
| NS5B storage buffer: | 0.1 µM NS5B |
| | 25 mM Tris-HCl pH 7.5 |
| | 300 mM NaCl |
| | 5 mM DTT |
| | 1 mM EDTA |
| | 0.1% n-Dodecyl maltoside |
| | 30% glycerol |

Test compound cocktail: Just prior to assay, test compounds of the invention were dissolved in assay buffer containing 15% DMSO.

Substrate cocktail: Just prior to assay, the substrates were mixed in assay buffer to the following concentrations:

| Component | Concentration in substrate cocktail | Final Concentration in assay |
| --- | --- | --- |
| RNAsin ™ | 0.5 U/µL | 1.67 U/µL |
| Biotin-oligo-U$_{12}$ primer | 3 ng/µL | 1 ng/µL |
| PolyA template | 30 ng/µL | 10 ng/µL |
| UTP-[5,6-$^3$H] 35 Ci/mmol | 0.025 µCi/µL | 0.0083 µCi/µL 0.25 µM |
| UTP | 2.25 µM | 0.75 µM |

Enzyme cocktail: Just prior to assay, the RNA polymerase (NS5B) cocktail was prepared in assay buffer to the following specifications:

| Component | Concentration in cocktail |
| --- | --- |
| Tris-HCl at pH 7.5 | 20 mM |
| MgCl$_2$ | 5 mM |
| KCl | 25 mM |
| EDTA | 1 mM |
| DTT | 1 mM |
| n-Dodecyl maltoside | 1% |
| NS5B | 30 nM |

Protocol:

The assay reaction was performed in a Microfluor™ white "U" bottom plate (Dynatech™ #7105), by successively adding:

20 µL of test compound cocktail;

20 µL of substrate cocktail; and

20 µL of enzyme cocktail (final [NS5B] in assay=10 nM; final [n-dodecyl maltoside] in assay=0.33%; final DMSO in assay=5%).

The reaction was incubated at room temperature for 1.5 hours. STOP solution (20 µL; 0.5 M EDTA, 150 ng/µl tRNA) was added, followed by 30 µl streptavidin coated PVT beads (8 mg/ml in 20 mM Tris-HCl, pH 7.5, 25 mM KCl, 0.025% NaN$_3$). The plate was then shaken for 30 minutes. A solution of CsCl was added (70 µL, 5 M), to bring the CsCl concentration to 1.95 M. The mixture was then allowed to stand for 1 hour. The beads were then counted on a Hewlett Packard TopCount™ instrument using the following protocol:

Data mode: counts per minute

Scintillator: liq/plast

Energy range: low

Efficiency mode: normal

Region: 0-50

Count delay: 5 minutes

Count time: 1 minute

Expected results: 6000 cpm/well 200 cpm/well no enzyme control.

Based on the results at ten different concentrations of test compound, standard concentration-% inhibition curves were plotted and analysed to determine IC$_{50}$'s for the compounds of the invention. For some compounds the IC$_{50}$ was estimated from two points.

Example 24

Specificity of NS5B RNA Dependent RNA Polymerase Inhibition

The compounds of the invention were tested for inhibitory activity against polio virus RNA dependent RNA polymerase and calf thymus DNA dependent RNA polymerase II in the format that is described for the HCV polymerase with the exception that another polymerase was used in place of the HCV NS5B polymerase.

Example 25

Cell Based HCV RNA Replication Assay

Cell Culture

Huh7 cells that stably maintain a subgenomic HCV replicon were established as previously described (Lohman et al., 1999. Science 285: 110-113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50 000 cells/ml in Standard Medium. 200 μL (10 000 cells) are distributed into each well of a 96-well plate. The plate was then incubated at 37° C. with 5% $CO_2$ until the next day.

Reagents and Materials:

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 μm Filter Unit | Millipore | SLGV025LS | RT |
| Deep-Well Titer Plate Polypropylene | Beckman | 267007 | RT |

Preparation of Test Compound

10 μL of test compound (in 100% DMSO) was added to 2 ml of Assay Medium for a final DMSO concentration of 0.5% and the solution was sonicated for 15 min and filtered through a 0.22 μM Millipore Filter Unit. 900 μl was transferred into row A of a Polypropylene Deep-Well Titer Plate. Rows B to H, contain 400 μL aliquots of Assay Medium (containing 0.5% DMSO), and are used to prepare serial dilutions (½) by transferring 400 μl from row to row (no compound was included in row H).

Application of Test Compound to Cells

Cell culture medium was aspirated from the 96-well plate containing the S22.3 cells. 175 μL of assay medium with the appropriate dilution of test compound was transferred from each well of the compound plate to the corresponding well of the cell culture plate (row H was used as the "No inhibition control"). The cell culture plate was incubated at 37° C. with 5% $CO_2$ for 72 hours.

Extraction of Total Cellular RNA

Following the 72 hour incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 μL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 ml of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 μL of RNase-free water to each well, sealing plate with a new piece of tape and incubated for 1 min at room temperature. The plate was then centrifuged at 6000 rpm for 4 min at room temperature. The elution step was repeated with a second volume of 50 μl RNase-free water. The microtubes with total cellular RNA are stored at −70° C.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 μL of reagent was diluted in 10 mL TE. A Standard Curve of ribosomal RNA was diluted in TE to 2 μg/mL and pre-determined amounts (100, 50, 40, 20, 10, 5, 2 and 0 μL) of the ribosomal RNA solution are then transferred in a new 96-well plate (COSTAR #3997) and the volume was completed to 100 μL with TE. Generally, column 1 of the 96-well plate was used for the standard curve and the other wells are used for the RNA samples to be quantified. 10 μL of each RNA sample that was to be quantified, was transferred to the corresponding well of the 96-well plate and 90 μL of TE was added. One volume (100 μL) of diluted RiboGreen reagent was added to each well of the 96-well plate and incubated for 2 to 5 minutes at room temperature, protected from light (a 10 μL RNA sample in a 200 μL final volume generates a 20× dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20× dilution.

Reagents and Materials:

| Product | Company | Catalog # | Storage |
|---|---|---|---|
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327-332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each RT-PCR plate. HCV Replicon RNA was synthesized (by T7 transcription) in vitro, purified and quantified by $OD_{260}$. Considering that 1 µg of this RNA=$2.15 \times 10^{11}$ RNA copies, dilutions are made in order to have $10^8$, $10^7$, $10^6$, $10^5$, $10^4$, $10^3$ or $10^2$ genomic RNA copies/5 µL. Total cellular Huh-7 RNA was also incorporated with each dilution (50 ng/5 µL). 5 µL of each reference standard (HCV Replicon+Huh-7 RNA) was combined with 45 µL of Reagent Mix, and used in the Real-Time RT-PCR reaction.

The Real-Time RT-PCR reaction was set-up for the experimental samples that were purified on RNeasy 96-well plates by combining 5 µl of each total cellular RNA sample with 45 µL of Reagent Mix.

Reagents and Materials:

| Product | Company | Catalog # | Storage |
| --- | --- | --- | --- |
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix Preparation:

| Component | Volume for one sample (µL) | Volume for One Plate (µL) (91 samples + Dead Volume) | Final conc. | |
| --- | --- | --- | --- | --- |
| Rnase-free water | 16.5 | 1617 | | |
| 5× TaqMan EZ buffer | 10 | 980 | 1× | |
| Mn(OAc)₂ (25 mM) | 6 | 588 | 3 | mM |
| dATP (10 mM) | 1.5 | 147 | 300 | µM |
| dCTP (10 mM) | 1.5 | 147 | 300 | µM |
| dGTP (10 mM) | 1.5 | 147 | 300 | µM |
| dUTP (20 mM) | 1.5 | 147 | 600 | µM |
| Forward Primer (10 µM) | 1 | 98 | 200 | nM |
| Reverse Primer (10 µM) | 1 | 98 | 200 | nM |
| PUTR probe (5 µM) | 2 | 196 | 200 | nM |
| rTth DNA polymerase (2.5 U/µL) | 2 | 196 | 0.1 | U/µL |
| AmpErase UNG (1 U/µL) | 0.5 | 49 | 0.01 | U/µL |
| Total Volume | 45 | 4410 | | |

```
Forward Primer Sequence (SEQ ID. 2):
5'-ACG CAG AAA GCG TCT AGC CAT GGC GTT AGT-3'

Reverse Primer Sequence (SEQ ID NO. 3):
5'-TCC CGG GGC ACT CGC AAG CAC CCT ATC AGG-3'
Note:
Those primers amplify a region of 256-nt present within the
5' untranslated region of HCV.

PUTR Probe Sequence (SEQ ID NO. 4):
    6FAM-TGG TCT GCG GAA CCG GTG AGT ACA CC-TAMRA
```

No Template Controls (NTC): On each plate, 4 wells are used as "NTC". For these controls, 5 µl of water are added to the well in place of RNA.

Thermal Cycling Conditions:

| | | |
| --- | --- | --- |
| 50° C. | 2 min | |
| 60° C. | 30 min | |
| 95° C. | 5 min | |
| 95° C. | 15 sec | } for 2 cycles |
| 60° C. | 1 min | |
| 90° C. | 15 sec | } for 40 cycles |
| 60° C. | 1 min | |

Following the termination of the RT-PCR reaction the data analysis requires setting of threshold fluorescence signal for the PCR plate and a standard curve was constructed by plotting the Ct value versus RNA copy number used in each reference reaction. The Ct values obtained for the assay samples are used to interpolate an RNA copy number based on the standard curve.

Finally, the RNA copy number was normalized (based on the RiboGreen RNA quantification of the total RNA extracted from the cell culture well) and expressed as genome equivalents/µg of total RNA [ge/µg].

The RNA copy number [g.e./µg] from each well of the cell culture plate was a measure of the amount of replicating HCV RNA in the presence of various concentrations of inhibitor. The % inhibition was calculated with the following equation:

$$100 - [(g.e./\mu g\ inh)/(g.e./\mu g\ ctl) \times 100].$$

A non-linear curve fit with the Hill model was applied to the inhibition-concentration data, and the 50% effective concentration (EC$_{50}$) was calculated by the use of SAS software (Statistical Software System; SAS Institute, Inc. Cary, N.C.).

In Table 1 below, the following ranges apply:

IC$_{50}$: A=≧1 µM; B=1 µM-500 nM; and C<500 nM.

Ec$_{50}$: A=≧1 µM; and B=<1 µM

TABLE 1

| Cpd. # | A | R² | R³ | Z | IC$_{50}$ | EC$_{50}$ | m/z (M + H)⁺ |
|---|---|---|---|---|---|---|---|
| 101 | N—Me | phenyl | cyclohexyl | OH | A | — | 334.1 |
| 102 | NH | 3-furyl | cyclohexyl | OH | A | A | 310.0 |
| 103 | NH | 2-furyl | cyclohexyl | OH | A | — | 308.0 |
| 104 | NH | 3-thienyl | cyclohexyl | OH | A | — | 324.0 (M − H) |
| 105 | NH | Br | cyclohexyl | OH | A | — | 319.9 |
| 106 | N—Me | 2-pyridyl | cyclohexyl | OH | B | A | 335.2 |
| 107 | N—Me | 3-furyl | cyclohexyl | OH | B | A | 324.1 |
| 108 | N—Me | 5-methyl-2-pyridyl | cyclohexyl | OH | B | B | 349.1 |
| 109 | N—Me | 2-pyrazinyl | cyclohexyl | OH | C | A | 336.1 |
| 110 | NH | 3-furyl | cyclopentyl | OH | C | — | 296.0 |
| 111 | N—Me | 3-furyl | cyclopentyl | OH | C | A | 310.0 |

TABLE 1-continued

| Cpd. # | A | R² | R³ | Z | IC₅₀ | EC₅₀ | m/z (M + H)⁺ |
|---|---|---|---|---|---|---|---|
| 112 | N—Me | 6-amino-pyridin-2-yl | cyclohexyl | OH | C | A | 350.1 |
| 113 | N—Me | 6-amino-pyridin-2-yl | cyclopentyl | OH | C | — | 336.1 |
| 114 | N-CH₂COOH | furan-3-yl | cyclohexyl | OMe | A | A | 382 |
| 115 | N—Me | pyridin-2-yl | cyclopentyl | OH | B | A | 321 |
| 116 | N-CH₂COOH | furan-3-yl | cyclohexyl | OH | C | — | 368.1 |
| 117 | N—Me | thiazol-4-yl | cyclopentyl | OH | C | A | 327.1 |
| 118 | N—Me | 2-acetamido-thiazol-4-yl | cyclopentyl | OH | C | A | 384.1 |
| 119 | N—Me | 2-methylamino-thiazol-4-yl | cyclopentyl | OH | B | A | 356.2 |

TABLE 1-continued
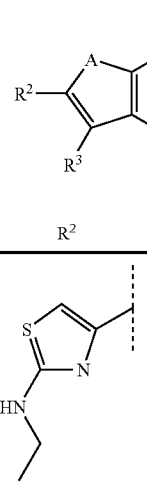
| Cpd. # | A | R² | R³ | Z | IC₅₀ | EC₅₀ | m/z (M + H)⁺ |
|---|---|---|---|---|---|---|---|
| 120 | N—Me | 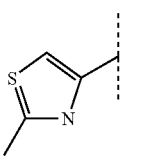 | cyclopentyl | OH | A | — | 370.2 |
| 121 | N—Me | 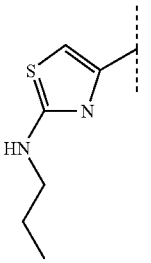 | cyclopentyl | OH | B | A | 341.1 |
| 122 | N—Me | 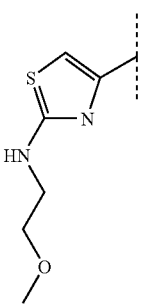 | cyclopentyl | OH | A | — | 384.2 |
| 123 | N—Me | 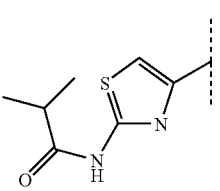 | cyclopentyl | OH | C | A | 400.2 |
| 124 | N—Me | 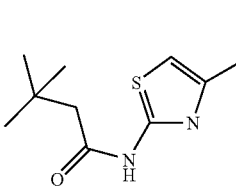 | cyclopentyl | OH | A | — | 384.1 |
| 125 | N—Me |  | cyclopentyl | OH | A | — | 440.2 |

TABLE 1-continued

| Cpd. # | A | R² | R³ | Z | IC₅₀ | EC₅₀ | m/z (M + H)⁺ |
|---|---|---|---|---|---|---|---|
| 126 | N—Me | pivaloylamino-thiazolyl | cyclopentyl | OH | A | — | 426.2 |
| 127 | N—Me | 2-(2-(dimethylamino)ethylamino)thiazol-4-yl | cyclopentyl | OH | C | A | 413.2 |
| 128 | N—Me | oxazol-5-yl | cyclopentyl | OH | C | A | 311.1 |
| 129 | N—Me | thiazol-2-yl | cyclopentyl | OH | B | A | 327.1 |
| 130 | N—Me | 3-aminophenyl | cyclopentyl | OH | A | — | 335.2 |
| 131 | N—Me | 4-aminophenyl | cyclopentyl | OH | B | A | 335.2 |
| 132 | N—Me | thiophen-3-yl | cyclopentyl | OH | C | A | 326.1 |
| 133 | N—Me | pyridin-2-yl | cyclopentyl | OH | B | A | 335.2 |

TABLE 1-continued

| Cpd. # | A | R² | R³ | Z | IC₅₀ | EC₅₀ | m/z (M + H)⁺ |
|---|---|---|---|---|---|---|---|
| 134 | N—Me | 6-methylpyridin-3-yl | cyclopentyl | OH | B | — | 335.2 |
| 135 | N—Me | pyrazin-2-yl | cyclopentyl | OH | C | A | 322.2 |
| 136 | N—Me | 5-bromopyridin-2-yl | cyclopentyl | OH | B | — | 399.1 |
| 137 | N—Me | 5-nitropyridin-2-yl | cyclopentyl | OH | B | — | 366.1 |
| 138 | S | pyridin-2-yl | cyclopentyl | OH | A | A | 324.1 |
| 139 | N—Me | 2-aminothiazol-4-yl | cyclohexyl | OH | C | — | 356.1 |
| 140 | S | furan-3-yl | cyclopentyl | OH | A | — | 331.1 |
| 141 | O | pyridin-2-yl | cyclopentyl | OH | A | A | 308.2 |
| 142 | NH | pyridin-2-yl | cyclohexyl | OH | A | — | 321.1 |
| 143 | N-CH₂COOH | pyridin-2-yl | cyclohexyl | OH | B | — | 379.2 |
| 144 | N—Me | 5-chloropyridin-2-yl | cyclopentyl | OH | A | — | 355.0 |

TABLE 1-continued

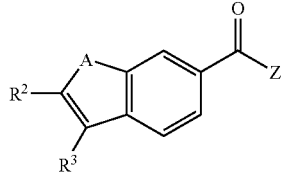

| Cpd. # | A | R² | R³ | Z | IC₅₀ | EC₅₀ | m/z (M + H)⁺ |
|---|---|---|---|---|---|---|---|
| 145 | NH | 2-pyridyl | cyclopentyl | OH | A | A | 307.1 |
| 146 | alanine (CH(CH₃)(COOH)NH-) | 5-bromo-2-pyridyl | cyclohexyl | OH | A | — | 471.1 |
| 147 | N—Me | 5-methoxy-2-pyridyl | cyclopentyl | OH | A | — | 351.1 |
| 148 | N—Me | 5-fluoro-2-pyridyl | cyclopentyl | OH | B | — | 339.1 |
| 149 | glycine (CH₂(COOH)NH-) | 5-bromo-2-pyridyl | cyclohexyl | OH | B | — | 457.2 |
| 150 | N—Me | 2-pyridyl | cyclopentenyl | OH | — | — | 319.0 |

TABLE 2

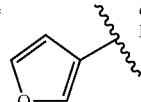

| Cpd. # | A | R² | R³ | Z | IC₅₀ | EC₅₀ | m/z (M + H)⁺ |
|---|---|---|---|---|---|---|---|
| 201 | N—Me | phenyl | cyclohexyl | OH | A | — | 335.3 |
| 202 | N—Me | 3-furyl | cyclohexyl | OH | A | — | 325.2 |

What is claimed is:

1. A compound represented by Formula II

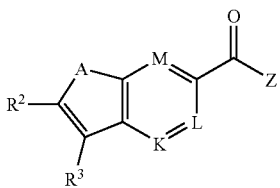

wherein:

A is $NR^1$, wherein $R^1$ is H or $(C_{1-6})$alkyl optionally substituted with:

halogen, $OR^{11}$, $SR^{11}$ or $N(R^{12})_2$, wherein $R^{11}$ and each $R^{12}$ is independently H, $(C_{1-6})$alkyl, $(C_{3-7})$cycloalkyl, $(C_{1-6})$alkyl-$(C_{3-7})$cycloalkyl, $(C_{1-6})$alkyl-aryl or $(C_{1-6})$alkyl-Het, said aryl or Het optionally substituted with $R^{10}$; or both $R^{12}$ are covalently bonded together and to the nitrogen to which they are both attached to form a 5, 6 or 7-membered saturated heterocycle;

$R^2$ is halogen, $R^{21}$, $OR^{21}$, $SR^{21}$, $COOR^{21}$, $SO_2N(R^{22})_2$, $N(R^{22})_2$, $CON(R^{22})_2$, $NR^{22}C(O)R^{22}$ or $NR^{22}C(O)NR^{22}$ wherein $R^{21}$ and each $R^{22}$ is independently H, $(C_{1-6})$alkyl, haloalkyl, $(C_{2-6})$alkenyl, $(C_{3-7})$cycloalkyl, $(C_{2-6})$alkynyl, $(C_{5-7})$cycloalkenyl, 6 or 10-membered aryl or Het, said $R^{21}$ and $R^{22}$ being optionally substituted with $R^{20}$, or both $R^{22}$ are bonded together to form a 5, 6 or 7-membered saturated heterocycle with the nitrogen to which they are attached;

wherein $R^{10}$ and $R^{20}$ is each:

1 to 4 substituents which are, independently, halogen, $OPO_3H$, $NO_2$, cyano, azido, $C(=NH)NH_2$, $C(=NH)NH(C_{1-6})$alkyl or $C(=NH)NHCO(C_{1-6})$alkyl; or 1 to 4 substituents which are, independently, a) $(C_{1-6})$ alkyl or haloalkyl, $(C_{3-7})$cycloalkyl, $C_{3-7}$ spiro-cycloalkyl optionally containing 1 or 2 heteroatom, $(C_{2-6})$alkenyl, $(C_{3-6})$cycloalkenyl, $(C_{2-8})$alkynyl, $(C_{1-6})$ alkyl-$(C_{3-7})$cycloalkyl, all of which optionally substituted with $R^{150}$;

b) $OR^{104}$ wherein $R^{104}$ is H, $(C_{1-6}$alkyl$)$, $(C_{3-7})$cycloalkyl, or $(C_{1-6})$alkyl-$(C_{3-7})$cycloalkyl, aryl, Het, $(C_{1-6}$alkyl$)$aryl or $(C_{1-6}$alkyl$)$Het, said alkyl, cycloalkyl, aryl, Het, $(C_{1-6}$alkyl$)$aryl or $(C_{1-6}$alkyl$)$Het being optionally substituted with $R^{150}$;

c) $OCOR^{105}$ wherein $R^{105}$ is $(C_{1-6})$cycloalkyl, $(C_{3-7})$cycloalkyl, $(C_{1-6})$alkyl-$(C_{3-7})$cycloalkyl, Het, $(C_{1-6}$alkyl$)$aryl or $(C_{1-6}$alkyl$)$Het, said alkyl, cycloalkyl, aryl, Het, $(C_{1-6}$alkyl$)$aryl or $(C_{1-6}$alkyl$)$Het being optionally substituted with $R^{150}$;

d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, $(C_{1-6}$alkyl$)$aryl or $(C_{1-6}$alkyl$)$Het or both $R^{108}$ are covalently bonded together and to the nitrogen to which they are attached to form a 5, 6 or 7-membered saturated heterocycle, said alkyl, cycloalkyl, aryl, Het, $(C_{1-6}$alkyl$)$aryl or $(C_{1-6}$alkyl$)$Het or heterocycle being optionally substituted with $R^{150}$;

e) $NR^{111}R^{112}$ wherein $R^{111}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl$)$aryl or $(C_{1-6}$alkyl$)$Het, and $R^{112}$ is H, CN, $(C_{1-6})$alkyl, $(C_{3-7})$cycloalkyl or $(C_{1-6})$alkyl-$(C_{3-7})$cycloalkyl, aryl, Het, $(C_{1-6}$alkyl$)$aryl, $(C_{1-6}$alkyl$)$Het, $COOR^{115}$ or $SO_2R^{115}$ wherein $R^{115}$ is $(C_{1-6})$alkyl, $(C_{3-7})$cycloalkyl, or $(C_{1-6})$alkyl-$(C_{3-7})$cycloalkyl, aryl, Het, $(C_{1-6}$alkyl$)$aryl or $(C_{1-6}$alkyl$)$Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}$alkyl$)$aryl or $(C_{1-6}$alkyl$)$Het, or heterocycle being optionally substituted with $R^{150}$;

f) $NR^{116}COR^{117}$ wherein $R^{116}$ and $R^{117}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl$)$aryl or $(C_{1-6}$alkyl$)$Het, said $(C_{1-6})$alkyl, $(C_{3-7})$cycloalkyl, $(C_{1-6})$alkyl-$(C_{3-7})$cycloalkyl, aryl, Het, $(C_{1-6}$alkyl$)$aryl or $(C_{1-6}$alkyl$)$Het being optionally substituted with $R^{150}$;

g) $NR^{118}CONR^{119}R^{120}$, wherein $R^{118}$, $R^{119}$ and $R^{120}$ is each H, $(C_{1-6})$alkyl, $(C_{3-7})$cycloalkyl, $(C_{1-6})$alkyl-$(C_{3-7})$cycloalkyl, aryl, Het, $(C_{1-6}$alkyl$)$aryl or $(C_{1-6}$alkyl$)$Het, or $R^{118}$ is covalently bonded to $R^{119}$ and to the nitrogen to which they are attached to form a 5, 6 or 7-membered saturated heterocycle;

or $R^{119}$ and $R^{120}$ are covalently bonded together and to the nitrogen to which they are attached to form a 5, 6 or 7-membered saturated heterocycle;

said alkyl, cycloalkyl, $(C_{1-6})$alkyl-$(C_{3-7})$cycloalkyl, aryl, Het, $(C_{1-6}$alkyl$)$aryl or $(C_{1-6}$alkyl$)$Het or heterocycle being optionally substituted with $R^{150}$;

h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl$)$aryl or $(C_{1-6}$alkyl$)$Het, said alkyl, cycloalkyl, alkyl-cycloalkyl, aryl, Het, $(C_{1-6}$alkyl$)$aryl or $(C_{1-6}$alkyl$)$Het being optionally substituted with $R^{150}$;

or $R^{122}$ is $OR^{123}$ or $N(R^{124})_2$ wherein $R^{123}$ and each $R^{124}$ is independently H, $(C_{1-6}$alkyl$)$, $(C_{3-7})$cycloalkyl, or $(C_{1-6})$alkyl-$(C_{3-7})$cycloalkyl, aryl, Het, $(C_{1-6}$alkyl$)$aryl or $(C_{1-6}$alkyl$)$Het, or $R^{124}$ is OH or O$(C_{1-6}$alkyl$)$ or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl$)$aryl or $(C_{1-6}$alkyl$)$Het and heterocycle being optionally substituted with $R^{150}$;

i) $COR^{127}$ wherein $R^{127}$ is H, $(C_{1-6})$alkyl, $(C_{3-7})$cycloalkyl or $(C_{1-6})$alkyl-$(C_{3-7})$cycloalkyl, aryl, Het, $(C_{1-6}$alkyl$)$aryl or $(C_{1-6}$alkyl$)$Het, said alkyl, cycloalkyl, aryl, Het, $(C_{1-6}alkyl)aryl$ or $(C_{1-6}alkyl)$Het being optionally substituted with $R^{150}$;
j) $COOR^{128}$ wherein $R^{128}$ is H, $(C_{1-6})alkyl$, $(C_{3-7})$cycloalkyl, or $(C_{1-6})alkyl$-$(C_{3-7})$cycloalkyl, aryl, Het, $(C_{1-6}alkyl)aryl$ or $(C_{1-6}alkyl)$Het, said $(C_{1-6})alkyl$, $(C_{3-7})$cycloalkyl, or $(C_{1-6})alkyl$-$(C_{3-7})$cycloalkyl, aryl, Het, $(C_{1-6}alkyl)aryl$ and $(C_{1-6}alkyl)$Het being optionally substituted with $R^{150}$;
k) $CONR^{129}R^{130}$ wherein $R^{129}$ and $R^{130}$ are independently H, $(C_{1-6})alkyl$, $(C_{3-7})$cycloalkyl, $(C_{1-6})alkyl$-$(C_{3-7})$cycloalkyl, aryl, Het, $(C_{1-6}alkyl)aryl$ or $(C_{1-6}alkyl)$Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}alkyl)aryl$, $(C_{1-6}alkyl)$Het and heterocycle being optionally substituted with $R^{150}$;
l) aryl, Het, $(C_{1-6}alkyl)aryl$ or $(C_{1-6}alkyl)$Het, all of which being optionally substituted with $R^{150}$; and wherein $R^{150}$ is defined as:
1 to 3 substituents which are, independently, halogen, $OPO_3H$, $NO_2$, cyano, azido, $C(=NH)NH_2$, $C(=NH)NH(C_{1-6})alkyl$ or $C(=NH)NHCO(C_{1-6})alkyl$; or
1 to 3 substituents which are, independently,
a) $(C_{1-6})$ alkyl or haloalkyl, $(C_{3-7})$cycloalkyl, $C_{3-7}$ spirocycloalkyl optionally containing 1 or 2 heteroatom, $(C_{2-6})alkenyl$, $(C_{2-8})alkynyl$, $(C_{1-6})$ alkyl-$(C_{3-7})$cycloalkyl, all of which optionally substituted with $R^{160}$;
b) $OR^{104}$ wherein $R^{104}$ is H, $(C_{1-6}alkyl)$, $(C_{3-7})$cycloalkyl, or $(C_{1-6})alkyl$-$(C_{3-7})$cycloalkyl, aryl, Het, $(C_{1-6}alkyl)aryl$ or $(C_{1-6}alkyl)$Het, said alkyl, cycloalkyl, aryl, Het, $(C_{1-6}alkyl)aryl$ or $(C_{1-6}alkyl)$Het being optionally substituted with $R^{160}$;
c) $OCOR^{105}$ wherein $R^{105}$ is $(C_{1-6})alkyl$, $(C_{3-7})$cycloalkyl, $(C_{1-6})alkyl$-$(C_{3-7})$cycloalkyl, Het, $(C_{1-6}alkyl)aryl$ or $(C_{1-6}alkyl)$Het, said alkyl, cycloalkyl, aryl, Het, $(C_{1-6}alkyl)aryl$ or $(C_{1-6}alkyl)$Het being optionally substituted with $R^{160}$;
d) $SR^{108}$, $SO_2N(R^{108})_2$ or $SO_2N(R^{108})C(O)R^{108}$ wherein each $R^{108}$ is independently H, $(C_{1-6})alkyl$, $(C_{3-7})$cycloalkyl or $(C_{1-6})alkyl$-$(C_{3-7})$cycloalkyl, aryl, Het, $(C_{1-6}alkyl)aryl$ or $(C_{1-6}alkyl)$Het or both $R^{108}$ are covalently bonded together and to the nitrogen to which they are attached to form a 5, 6 or 7-membered saturated heterocycle, said alkyl, cycloalkyl, aryl, Het, $(C_{1-6}alkyl)aryl$ or $(C_{1-6}alkyl)$Het or heterocycle being optionally substituted with $R^{160}$;
e) $NR^{111}R^{112}$ wherein $R^{111}$ is H, $(C_{1-6})alkyl$, $(C_{3-7})$cycloalkyl or $(C_{1-6})alkyl$-$(C_{3-7})$cycloalkyl, aryl, Het, $(C_{1-6}alkyl)aryl$ or $(C_{1-6}alkyl)$Het, and $R^{112}$ is H, CN, $(C_{1-6})alkyl$, $(C_{3-7})$cycloalkyl or $(C_{1-6})alkyl$-$(C_{3-7})$cycloalkyl, aryl, Het, $(C_{1-6}alkyl)aryl$, $(C_{1-6}alkyl)$Het, $COOR^{115}$ or $SO_2R^{115}$ wherein $R^{115}$ is $(C_{1-6})alkyl$, $(C_{3-7})$cycloalkyl, or $(C_{1-6})alkyl$-$(C_{3-7})$cycloalkyl, aryl, Het, $(C_{1-6}alkyl)aryl$ or $(C_{1-6}alkyl)$Het, or both $R^{111}$ and $R^{112}$ are covalently bonded together and to the nitrogen to which they are attached to form a 5, 6 or 7-membered saturated heterocycle, said alkyl, cycloalkyl, aryl, Het, $(C_{1-6}alkyl)aryl$ or $(C_{1-6}alkyl)$Het, or heterocycle being optionally substituted with $R^{160}$;
f) $NR^{116}COR^{117}$ wherein $R^{116}$ and $R^{117}$ is each H, $(C_{1-6})alkyl$, $(C_{3-7})$cycloalkyl, $(C_{1-6})alkyl$-$(C_{3-7})$cycloalkyl, aryl, Het, $(C_{1-6}alkyl)aryl$ or $(C_{1-6}alkyl)$Het, said $(C_{1-6})alkyl$, $(C_{3-7})$cycloalkyl, $(C_{1-6})alkyl$-$(C_{3-7})$cycloalkyl, aryl, Het, $(C_{1-6}alkyl)aryl$ or $(C_{1-6}alkyl)$Het being optionally substituted with $R^{160}$;
g) $NR^{118}CONR^{119}R^{120}$, wherein $R^{118}$, $R^{119}$ and $R^{120}$ is each H, $(C_{1-6})alkyl$, $(C_{3-7})$cycloalkyl, $(C_{1-6})alkyl$-$(C_{3-7})$cycloalkyl, aryl, Het, $(C_{1-6}alkyl)aryl$ or $(C_{1-6}alkyl)$Het, or $R^{118}$ is covalently bonded to $R^{119}$ and to the nitrogen to which they are attached to form a 5, 6 or 7-membered saturated heterocycle;
or $R^{119}$ and $R^{120}$ are covalently bonded together and to the nitrogen to which they are attached to form a 5, 6 or 7-membered saturated heterocycle;
said alkyl, cycloalkyl, $(C_{1-6})alkyl$-$(C_{3-7})$cycloalkyl, aryl, Het, $(C_{1-6}alkyl)aryl$ or $(C_{1-6}alkyl)$Het or heterocycle being optionally substituted with $R^{160}$;
h) $NR^{121}COCOR^{122}$ wherein $R^{121}$ and $R^{122}$ is each H, $(C_{1-6})alkyl$, $(C_{3-7})$cycloalkyl, $(C_{1-6})alkyl$-$(C_{3-7})$cycloalkyl, a 6- or 10-membered aryl, Het, $(C_{1-6}alkyl)aryl$ or $(C_{1-6}alkyl)$Het, said alkyl, cycloalkyl, alkyl-cycloalkyl, aryl, Het, $(C_{1-6}alkyl)aryl$ or $(C_{1-6}alkyl)$Het being optionally substituted with $R^{160}$;
or $R^{122}$ is $OR^{123}$ or $N(R^{124})_2$ wherein $R^{123}$ and each $R^{124}$ is independently H, $(C_{1-6}alkyl)$, $(C_{3-7})$cycloalkyl, or $(C_{1-6})alkyl$-$(C_{3-7})$cycloalkyl, aryl, Het, $(C_{1-6}alkyl)aryl$ or $(C_{1-6}alkyl)$Het, or $R^{124}$ is OH or $O(C_{1-6}alkyl)$ or both $R^{124}$ are covalently bonded together to form a 5, 6 or 7-membered saturated heterocycle, said alkyl, cycloalkyl, alkyl-cycloalkyl, aryl, Het, $(C_{1-6}alkyl)aryl$ or $(C_{1-6}alkyl)$Het and heterocycle being optionally substituted with $R^{160}$;
i) $COR^{127}$ wherein $R^{127}$ is H, $(C_{1-6})alkyl$, $(C_{3-7})$cycloalkyl or $(C_{1-6})alkyl$-$(C_{3-7})$cycloalkyl, aryl, Het, $(C_{1-6}alkyl)aryl$ or $(C_{1-6}alkyl)$Het, said alkyl, cycloalkyl, aryl, Het, $(C_{1-6}alkyl)aryl$ or $(C_{1-6}alkyl)$Het being optionally substituted with $R^{160}$;
j) tetrazole, $COOR^{128}$ wherein $R^{128}$ is H, $(C_{1-6})alkyl$, $(C_{3-7})$cycloalkyl, or $(C_{1-6})alkyl$-$(C_{3-7})$cycloalkyl, aryl, Het, $(C_{1-6}alkyl)aryl$ or $(C_{1-6}alkyl)$Het, said $(C_{1-6})alkyl$, $(C_{3-7})$cycloalkyl, or $(C_{1-6})alkyl$-$(C_{3-7})$cycloalkyl, aryl, Het, $(C_{1-6}alkyl)aryl$ and $(C_{1-6}alkyl)$Het being optionally substituted with $R^{160}$; and
k) $CONR^{129}R^{130}$ wherein $R^{129}$ and $R^{130}$ are independently H, $(C_{1-6})alkyl$, $(C_{3-7})$cycloalkyl, $(C_{1-6})alkyl$-$(C_{3-7})$cycloalkyl, aryl, Het, $(C_{1-6}alkyl)aryl$ or $(C_{1-6}alkyl)$Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}alkyl)aryl$, $(C_{1-6}alkyl)$Het and heterocycle being optionally substituted with $R^{160}$;
wherein $R^{160}$ is defined as 1 or 2 substituents which are, independently,
tetrazole, halogen, CN, $C_{1-6}alkyl$, haloalkyl, $COOR^{161}$, $SO_3H$, $SR^{161}$, $SO_2R^{161}$, $OR^{161}$, $N(R^{162})_2$, $SO_2N(R^{162})_2$, $NR^{162}COR^{162}$ or $CON(R^{162})_2$, wherein $R^{161}$ and each $R^{162}$ is independently H, $(C_{1-6})alkyl$, $(C_{3-7})$cycloalkyl or $(C_{1-6})alkyl$-$(C_{3-7})$cycloalkyl; or both $R^{162}$ are covalently bonded together and to the nitrogen to which they are attached to form a 5, 6 or 7-membered saturated heterocycle,
$R^3$ is, independently, $(C_{3-7})$cycloalkyl, $(C_{5-7})$cycloalkenyl, $(C_{6-10})$bicycloalkyl or $(C_{6-10})$bicycloalkenyl,
said cycloalkyl and bicycloalkyl being optionally substituted with from 1 to 4 substituents which are, independently, halogen, or
a) $(C_{1-6})alkyl$ optionally substituted with:
$OR^{31}$ or $SR^{31}$ wherein $R^{31}$ is H, $(C_{1-6}alkyl)$, $(C_{3-7})$cycloalkyl, $(C_{1-6})alkyl$-$(C_{3-7})$cycloalkyl, aryl, Het, $(C_{1-6})alkyl$-aryl or $(C_{1-6})alkyl$-Het; or N(R$^{32}$)$_2$ wherein each R$^{32}$ is independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$)alkyl-aryl or (C$_{1-6}$)alkyl-Het; or both R$^{32}$ are covalently bonded together and to the nitrogen to which they are attached to form a 5, 6 or 7-membered saturated heterocycle;

b) OR$^{33}$ wherein R$^{33}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$)alkyl-aryl or (C$_{1-6}$)alkyl-Het;

c) SR$^{34}$ wherein R$^{34}$ is H, (C$_{1-6}$)alkyl, (C$_{3-7}$)cycloalkyl, or (C$_{1-6}$)alkyl-(C$_{3-7}$)cycloalkyl, aryl, Het, (C$_{1-6}$)alkyl-aryl or (C$_{1-6}$)alkyl-Het; and d) N(R$^{35}$)$_2$ wherein each R$^{35}$ is independently H, (C$_{1-6}$)alkyl, (C$_{3-7}$)cycloalkyl, (C$_{1-6}$)alkyl-(C$_{3-7}$)cycloalkyl, aryl, Het, (C$_{1-6}$)alkyl-aryl or (C$_{1-6}$)alkyl-Het; or both R$^{35}$ are covalently bonded together and to the nitrogen to which they are attached to form a 5, 6 or 7-membered saturated heterocycle;

K is N or CR$^4$, wherein R$^4$ is H, halogen, (C$_{1-6}$)alkyl, haloalkyl, (C$_{3-7}$)cycloalkyl or (C$_{1-6}$)alkyl-(C$_{3-7}$)cycloalkyl; or R$^4$ is OR$^{41}$ or SR$^{41}$, COR$^{41}$ or NR$^{41}$COR$^{41}$ wherein each R$^{41}$ is independently H, (C$_{1-6}$)alkyl), (C$_{3-7}$)cycloalkyl or (C$_{1-6}$)alkyl-(C$_{3-7}$)cycloalkyl;

or R$^4$ is NR$^{42}$R$^{43}$ wherein R$^{42}$ and R$^{43}$ are each independently H, (C$_{1-6}$)alkyl, (C$_{3-7}$)cycloalkyl, (C$_{1-6}$)alkyl-(C$_{3-7}$)cycloalkyl, or both R$^{42}$ and R$^{43}$ are covalently bonded together and to the nitrogen to which they are attached to form a 5, 6 or 7-membered saturated heterocycle;

L is N or CR$^5$, wherein R$^5$ has the same definition as R$^4$ defined above;

M is N or CR$^7$, wherein R$^7$ has the same definition as R$^4$ defined above;

with the proviso that one and only one of K, L and M is N;

Z is OR$^6$, wherein R$^6$ is H, (C$_{1-6}$)alkyl being optionally substituted with: halo, hydroxy, carboxy, amino, C$_{1-6}$ alkoxy, C$_{1-6}$alkoxycarbonyl, and C$_{1-6}$ alkylamino; or R$^6$ is C$_{1-6}$ alkylaryl optionally substituted with: halogen, cyano, nitro, C$_{1-6}$ alkyl, C$_{1-6}$haloalkyl, C$_{1-6}$alkanoyl, —(CH$_2$)$_{1-6}$—COOR$^7$, —(CH$_2$)$_{1-6}$—CONR$^7$R$^8$, —(CH$_2$)$_{1-6}$—NR$^7$R$^8$, —(CH$_2$)$_{1-6}$—NR$^7$COR$^8$, —(CH$_2$)$_{1-6}$—NHSO$_2$R$^7$, —(CH$_2$)$_{1-6}$—OR$^7$, —(CH$_2$)$_{1-6}$—SR$^7$, —(CH$_2$)$_{1-6}$—SO$_2$R$^7$, and —(CH$_2$)$_{1-6}$—SO$_2$NR$^7$R$^8$, wherein each R$^7$ and each R$^8$ is H or C$_{1-6}$ alkyl, or Z is NR$^9$R$^{10}$ wherein each of R$^9$ and R$^{10}$ is, independently, H, C$_{1-6}$alkoxy, or C$_{1-6}$alkyl optionally substituted with halo, hydroxy, carboxy, amino, C$_{1-6}$ alkoxy, C$_{1-6}$alkoxycarbonyl, and C$_{1-6}$ alkylamino;

or an enantiomer, diastereoisomer, tautomer or pharmaceutically acceptable salt thereof.

2. The compound according to claim 1, wherein M, K and L are each independently CH or N, provided that only one of M, K and L is N.

3. The compound according to claim 1, having the following formula:

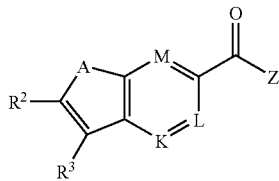

IId wherein R$^1$, R$^2$, R$^3$ and Z are as defined in claim 1.

4. The compound according to claim 1, wherein R$^1$ is H or (C$_{1-6}$)alkyl.

5. The compound according to claim 4, wherein R$^1$ is H, CH$_3$, isopropyl, or isobutyl.

6. The compound according to claim 5, wherein R$^1$ is H or CH$_3$.

7. The compound according to claim 6, wherein R$^1$ is CH$_3$.

8. The compound according to claim 1, wherein R$^2$ is, independently, H, halogen, (C$_{2-6}$)alkenyl, (C$_{5-7}$)cycloalkenyl, 6 or 10-membered aryl or Het; wherein (C$_{2-6}$)alkenyl, (C$_{5-7}$)cycloalkenyl, aryl or Het is optionally substituted with R$^{20}$, wherein R$^{20}$ is defined as:

1 to 4 substituents which are, independently of one another, halogen, NO$_2$, cyano, azido, C(=NH)NH$_2$, C(=NH)NH(C$_{1-6}$)alkyl or C(=NH)NHCO(C$_{1-6}$)alkyl; or 1 to 4 substituents which are, independently of one another, a) (C$_{1-6}$) alkyl or haloalkyl, (C$_{3-7}$)cycloalkyl, (C$_{2-6}$)alkenyl, (C$_{2-8}$)alkynyl, (C$_{1-6}$) alkyl-(C$_{3-7}$)cycloalkyl, all of which optionally substituted with R$^{150}$;

b) OR$^{104}$ wherein R$^{104}$ is H, (C$_{1-6}$alkyl), (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{150}$;

c) OCOR$^{105}$ wherein R$^{105}$ is (C$_{1-6}$)alkyl, (C$_{3-7}$)cycloalkyl, (C$_{1-6}$)alkyl-(C$_{3-7}$)cycloalkyl, Het, (C$_{1-6}$alkyl)aryl or (C$_{1-6}$alkyl)Het, said alkyl, cycloalkyl, aryl, Het, (C$_{1-6}$alkyl)aryl or (C$_{1-6}$alkyl)Het being optionally substituted with R$^{150}$;

d) SR$^{108}$, SO$_2$N(R$^{108}$)$_2$ or SO$_2$N(R$^{108}$)C(O)R$^{108}$ wherein each R$^{108}$ is independently H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het or both R$^{108}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het or heterocycle being optionally substituted with R$^{150}$;

e) NR$^{111}$R$^{112}$ wherein R$^{111}$ is H, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl or (C$_{1-6}$alkyl)Het, and R$^{112}$ is H, CN, (C$_{1-6}$)alkyl, (C$_{3-7}$)cycloalkyl or (C$_{1-6}$)alkyl-(C$_{3-7}$)cycloalkyl, aryl, Het, (C$_{1-6}$alkyl)aryl, (C$_{1-6}$alkyl)Het, COOR$^{115}$ or SO$_2$R$^{115}$ wherein R$^{115}$ is (C$_{1-6}$)alkyl, (C$_{3-7}$)cycloalkyl, or (C$_{1-6}$)alkyl-(C$_{3-7}$)cycloalkyl, aryl, Het, (C$_{1-6}$alkyl)aryl or (C$_{1-6}$alkyl)Het, or both R$^{111}$ and R$^{112}$ are covalently bonded together and to the nitrogen to which they are attached to form a 5, 6 or 7-membered saturated heterocycle, said alkyl, cycloalkyl, aryl, Het, (C$_{1-6}$alkyl)aryl or (C$_{1-6}$alkyl)Het, or heterocycle being optionally substituted with R$^{150}$;

f) NR$^{116}$COR$^{117}$ wherein R$^{116}$ and R$^{117}$ is each H, (C$_{1-6}$) alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, said (C$_{1-6}$) alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het being optionally substituted with R$^{150}$;

g) NR$^{118}$CONR$^{119}$R$^{120}$, wherein R$^{118}$, R$^{119}$ and R$^{120}$ is each H, (C$_{1-6}$)alkyl, (C$_{3-7}$)cycloalkyl, (C$_{1-6}$)alkyl-(C$_{3-7}$)cycloalkyl, aryl, Het, (C$_{1-6}$alkyl)aryl or (C$_{1-6}$alkyl)Het, or R$^{118}$ is covalently bonded to R$^{119}$ and to the nitrogen to which they are attached to form a 5, 6 or 7-membered saturated heterocycle;

or R$^{119}$ and R$^{120}$ are covalently bonded together and to the nitrogen to which they are attached to form a 5, 6 or 7-membered saturated heterocycle;

said alkyl, cycloalkyl, (C$_{1-6}$)alkyl-(C$_{3-7}$)cycloalkyl, aryl, Het, (C$_{1-6}$alkyl)aryl or (C$_{1-6}$alkyl)Het or heterocycle being optionally substituted with R$^{150}$;

h) $NR^{121}COCOR^{122}$ wherein $R^{121}$ and $R^{122}$ is each H, $(C_{1-6})$alkyl, $(C_{3-7})$cycloalkyl, $(C_{1-6})$alkyl-$(C_{3-7})$cycloalkyl, a 6- or 10-membered aryl, Het, $(C_{1-6}$alkyl)aryl or $(C_{1-6}$alkyl)Het, said alkyl, cycloalkyl, alkyl-cycloalkyl, aryl, Het, $(C_{1-6}$alkyl)aryl or $(C_{1-6}$alkyl)Het being optionally substituted with $R^{150}$;
or $R^{122}$ is $OR^{123}$ or $N(R^{124})_2$ wherein $R^{123}$ and each $R^{124}$ is independently H, $(C_{1-6}$alkyl), $(C_{3-7})$cycloalkyl, or $(C_{1-6})$alkyl-$(C_{3-7})$cycloalkyl, aryl, Het, $(C_{1-6}$alkyl)aryl or $(C_{1-6}$alkyl)Het, or $R^{124}$ is OH or $O(C_{1-6}$alkyl) or both $R^{124}$ are covalently bonded together to form a 5, 6 or 7-membered saturated heterocycle, said alkyl, cycloalkyl, alkyl-cycloalkyl, aryl, Het, $(C_{1-6}$alkyl)aryl or $(C_{1-6}$alkyl)Het and heterocycle being optionally substituted with $R^{150}$;
i) $COR^{127}$ wherein $R^{127}$ is H, $(C_{1-6})$alkyl, $(C_{3-7})$cycloalkyl or $(C_{1-6}$)alkyl-$(C_{3-7})$cycloalkyl, aryl, Het, $(C_{1-6}$alkyl)aryl or $(C_{1-6}$alkyl)Het, said alkyl, cycloalkyl, aryl, Het, $(C_{1-6}$alkyl)aryl or $(C_{1-6}$alkyl)Het being optionally substituted with $R^{150}$;
j) $COOR^{128}$ wherein $R^{128}$ is H, $(C_{1-6})$alkyl, $(C_{3-7})$cycloalkyl, or $(C_{1-6}$)alkyl-$(C_{3-7})$cycloalkyl, aryl, Het, $(C_{1-6}$alkyl)aryl or $(C_{1-6}$alkyl)Het, said $(C_{1-6}$)alkyl, $(C_{3-7})$cycloalkyl, or $(C_{1-6}$)alkyl-$(C_{3-7})$cycloalkyl, aryl, Het, $(C_{1-6}$alkyl)aryl and $(C_{1-6}$alkyl)Het being optionally substituted with $R^{150}$;
k) $CONR^{129}R^{130}$ wherein $R^{129}$ and $R^{130}$ are independently H, $(C_{1-6})$alkyl, $(C_{3-7})$cycloalkyl, $(C_{1-6})$alkyl-$(C_{3-7})$cycloalkyl, aryl, Het, $(C_{1-6}$alkyl)aryl or $(C_{1-6}$alkyl)Het, or both $R^{129}$ and $R^{130}$ are covalently bonded together and to the nitrogen to which they are attached to form a 5, 6 or 7-membered saturated heterocycle, said alkyl, cycloalkyl, alkyl-cycloalkyl, aryl, Het, $(C_{1-6}$alkyl)aryl, $(C_{1-6}$alkyl)Het and heterocycle being optionally substituted with $R^{150}$;
l) aryl, Het, $(C_{1-6}$alkyl)aryl or $(C_{1-6}$alkyl)Het, all of which being optionally substituted with $R^{150}$;
wherein $R^{150}$ is:
1 to 3 substituents which are, independently of one another, halogen, $NO_2$, cyano or azido; or
1 to 3 substituents which are, independently of one another,
a) $(C_{1-6})$ alkyl or haloalkyl, $(C_{3-7})$cycloalkyl, $(C_{2-6})$alkenyl, $(C_{2-8})$alkynyl, $(C_{1-6})$ alkyl-$(C_{3-7})$cycloalkyl, all of which optionally substituted with $R^{160}$;
b) $OR^{104}$ wherein $R^{104}$ is H, $(C_{1-6})$alkyl) or $(C_{3-7})$cycloalkyl, said alkyl or cycloalkyl optionally substituted with $R^{160}$;
d) $SR^{108}$, $SO_2N(R^{108})_2$ or $SO_2N(R^{108})C(O)R^{108}$ wherein each $R^{108}$ is independently H, $(C_{1-6})$alkyl, $(C_{3-7})$cycloalkyl or $(C_{1-6})$alkyl-$(C_{3-7})$cycloalkyl, aryl, Het, or both $R^{108}$ are covalently bonded together and to the nitrogen to which they are attached to form a 5, 6 or 7-membered saturated heterocycle, said alkyl, cycloalkyl, aryl, Het and heterocycle being optionally substituted with $R^{160}$;
e) $NR^{111}R^{112}$ wherein $R^{111}$ is H, $(C_{1-6})$alkyl, or $(C_{3-7})$cycloalkyl, and $R^{112}$ is H, $(C_{1-6})$alkyl or $(C_{3-7})$cycloalkyl, $COOR^{115}$ or $SO_2R^{115}$ wherein $R^{115}$ is $(C_{1-6})$alkyl or $(C_{3-7})$cycloalkyl, or both $R^{111}$ and $R^{112}$ are covalently bonded together and to the nitrogen to which they are attached to form a 5, 6 or 7-membered saturated heterocycle, said alkyl, cycloalkyl and heterocycle being optionally substituted with $R^{160}$;
f) $NR^{116}COR^{117}$ wherein $R^{116}$ and $R^{117}$ is each H, $(C_{1-6})$ alkyl or $(C_{3-7})$cycloalkyl said $(C_{1-6})$alkyl and $(C_{3-7})$cycloalkyl being optionally substituted with $R^{160}$;

g) $NR^{118}CONR^{119}R^{120}$, wherein $R^{118}$, $R^{119}$ and $R^{120}$ is each H, $(C_{1-6})$alkyl or $(C_{3-7})$cycloalkyl, or $R^{118}$ is covalently bonded to $R^{119}$ and to the nitrogen to which they are attached to form a 5, 6 or 7-membered saturated heterocycle;
or $R^{119}$ and $R^{120}$ are covalently bonded together and to the nitrogen to which they are attached to form a 5, 6 or 7-membered saturated heterocycle;
said alkyl, cycloalkyl, and heterocycle being optionally substituted with $R^{160}$;
h) $NR^{121}COCOR^{122}$ wherein $R^{121}$ is H, $(C_{1-6})$alkyl or $(C_{3-7})$cycloalkyl, said alkyl and cycloalkyl being optionally substituted with $R^{160}$;
or $R^{122}$ is $OR^{123}$ or $N(R^{124})_2$ wherein $R^{123}$ and each $R^{124}$ is independently H, $(C_{1-6})$alkyl) or $(C_{3-7})$cycloalkyl, or both $R^{124}$ are covalently bonded together to form a 5, 6 or 7-membered saturated heterocycle, said alkyl, cycloalkyl and heterocycle being optionally substituted with $R^{160}$;
i) $COR^{127}$ wherein $R^{127}$ is H, $(C_{1-6})$alkyl or $(C_{3-7})$cycloalkyl, said alkyl and cycloalkyl being optionally substituted with $R^{160}$;
j) $COOR^{128}$ wherein $R^{128}$ is H, $(C_{1-6})$alkyl or $(C_{3-7})$cycloalkyl, said $(C_{1-6})$alkyl and $(C_{3-7})$cycloalkyl being optionally substituted with $R^{160}$; and
k) $CONR^{129}R^{130}$ wherein $R^{129}$ and $R^{130}$ are independently H, $(C_{1-6})$alkyl or $(C_{3-7})$cycloalkyl, or both $R^{129}$ and $R^{130}$ are covalently bonded together and to the nitrogen to which they are attached to form a 5, 6 or 7-membered saturated heterocycle, said alkyl, cycloalkyl and heterocycle being optionally substituted with $R^{160}$;
wherein $R^{160}$ is defined as 1 or 2 substituents which are, independently of one another,
halogen, CN, $C_{1-6}$alkyl, haloalkyl, $COOR^{161}$, $OR^{161}$, $N(R^{162})_2$,
$SO_2N(R^{162})_2$, $NR^{162}COR^{162}$ or $CON(R^{162})_2$, wherein $R^{161}$ and each $R^{162}$ is independently H, $(C_{1-6})$alkyl, $(C_{3-7})$cycloalkyl or $(C_{1-6})$alkyl-$(C_{3-7})$cycloalkyl;
or both $R^{162}$ are covalently bonded together and to the nitrogen to which they are attached to form a 5, 6 or 7-membered saturated heterocycle.

9. The compound according to claim 8, wherein $R^2$ is, independently, aryl or Het, each optionally monosubstituted or disubstituted with a substituent which is halogen, haloalkyl, $N_3$, or
a) $(C_{1-6})$alkyl optionally substituted with OH, or $O(C_{1-6})$alkyl;
b) $(C_{1-6})$alkoxy;
e) $NR^{111}R^{112}$ wherein both $R^{111}$ and $R^{112}$ are independently H, $(C_{1-6})$alkyl, $(C_{3-7})$cycloalkyl, or $R^{112}$ is 6- or 10-membered aryl, Het, $(C_{1-6})$alkyl-aryl or $(C_{1-6})$alkyl-Het; or both $R^{111}$ and $R^{112}$ are covalently bonded together and to the nitrogen to which they are attached to form a 5, 6 or 7-membered saturated nitrogen-containing heterocycle, each of said alkyl, cycloalkyl, aryl, Het, alkyl-aryl or alkyl-Het; being optionally substituted with halogen or:
$OR^{161}$ or $N(R^{162})_2$, wherein $R^{161}$ and each $R^{162}$ is independently H, $(C_{1-6})$alkyl, or both $R^{162}$ are covalently bonded together and to the nitrogen to which they are attached to form a 5, 6 or 7-membered saturated nitrogen-containing heterocycle;
f) $NHCOR^{117}$ wherein $R^{117}$ is $(C_{1-6})$alkyl, $O(C_{1-6})$alkyl or $O(C_{3-7})$cycloalkyl;
i) CO-aryl; or k) CONH$_2$, CONH(C$_{1-6}$alkyl), CON(C$_{1-6}$alkyl)$_2$, CONH-aryl, or CONHC$_{1-6}$alkyl-aryl.

10. The compound according to claim 9, wherein R$^2$ is aryl or Het, each optionally monosubstituted or disubstituted with substituents halogen, haloalkyl, or a) (C$_{1-6}$)alkyl optionally substituted with OH, or O(C$_{1-6}$)alkyl;

b) (C$_{1-6}$)alkoxy; and e) NR$^{111}$R$^{112}$ wherein both R$^{111}$ and R$^{112}$ are independently H, (C$_{1-6}$)alkyl, (C$_{3-7}$)cycloalkyl, or R$^{112}$ is 6- or 10-membered aryl, Het, (C$_{1-6}$)alkyl-aryl or (C$_{1-6}$)alkyl-Het; or both R$^{111}$ and R$^{112}$ are covalently bonded together and to the nitrogen to which they are attached to form a 5, 6 or 7-membered saturated nitrogen-containing heterocycle, each of said alkyl, cycloalkyl, aryl, Het, alkyl-aryl or alkyl-Het; or being optionally substituted with halogen or:

OR$^{161}$ or N(R$^{162}$)$_2$, wherein R$^{161}$ and each R$^{162}$ is independently H, (C$_{1-6}$)alkyl, or both R$^{162}$ are covalently bonded together and to the nitrogen to which they are attached to form a 5, 6 or 7-membered saturated nitrogen-containing heterocycle.

11. The compound according to claim 10, wherein R$^2$ is phenyl or a heterocycle which is

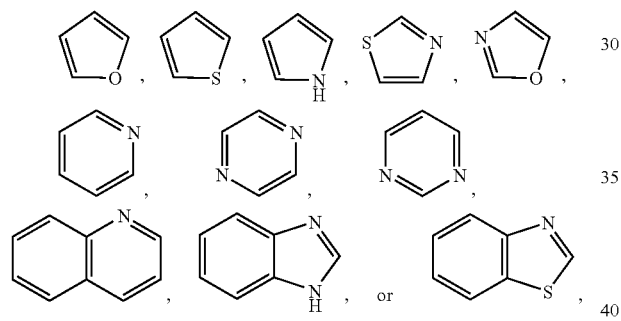

which is optionally substituted as defined in claim 10.

12. The compound according to claim 1, wherein R$^2$ is, independently,

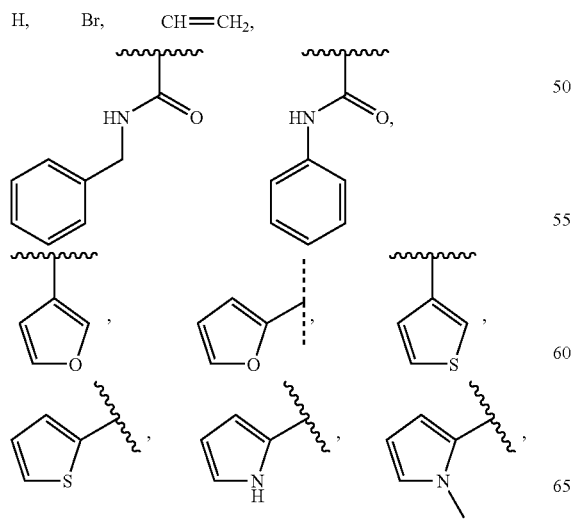

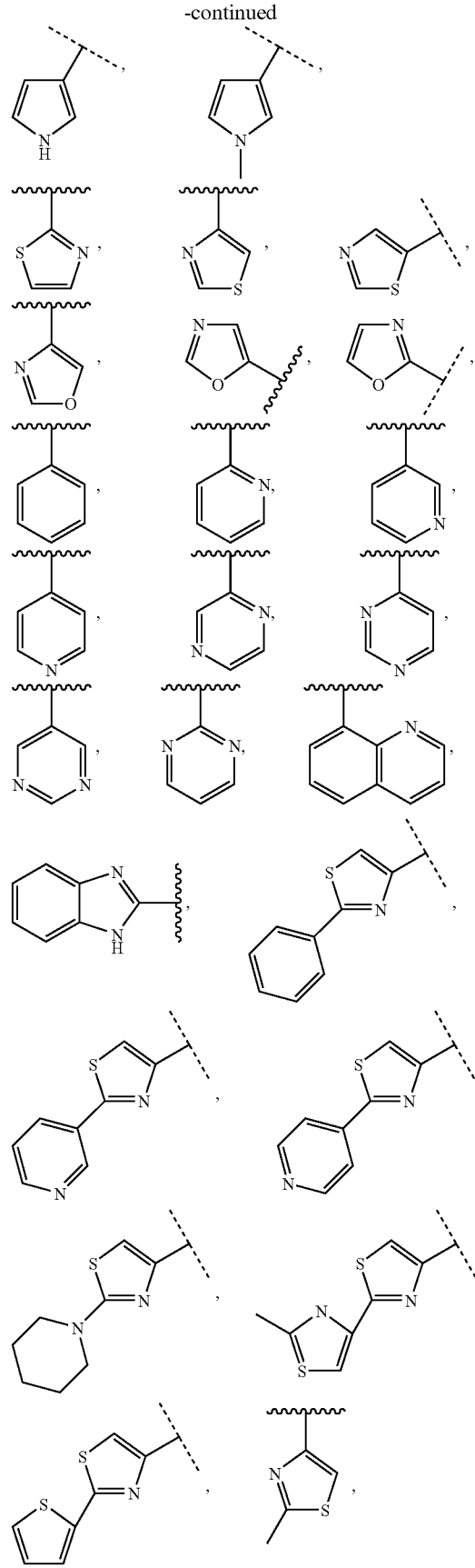

-continued
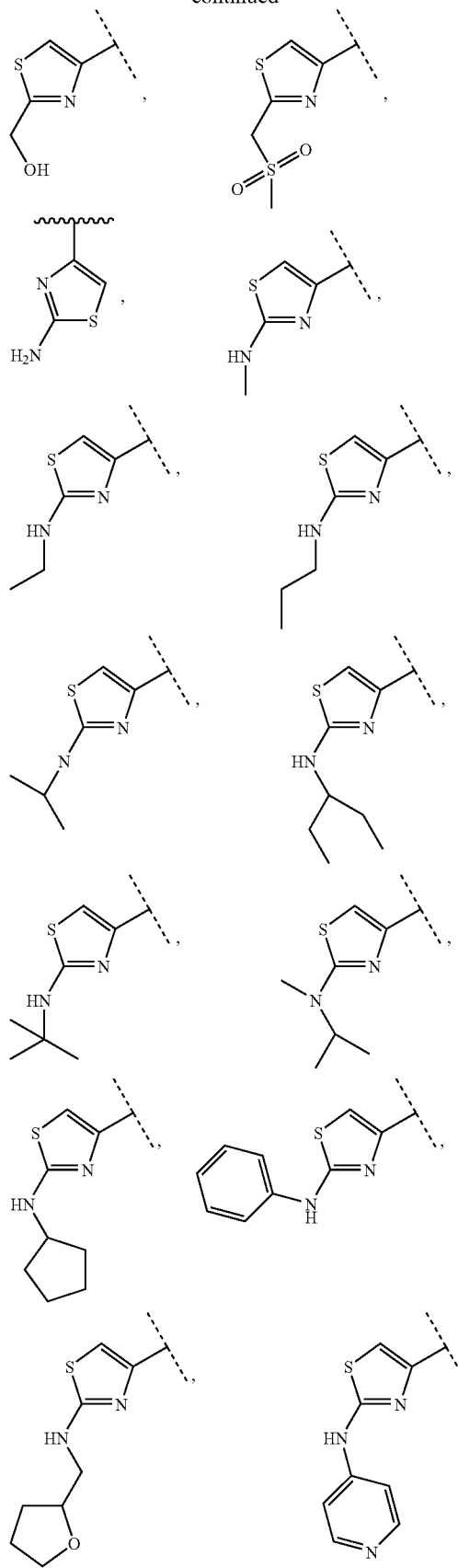
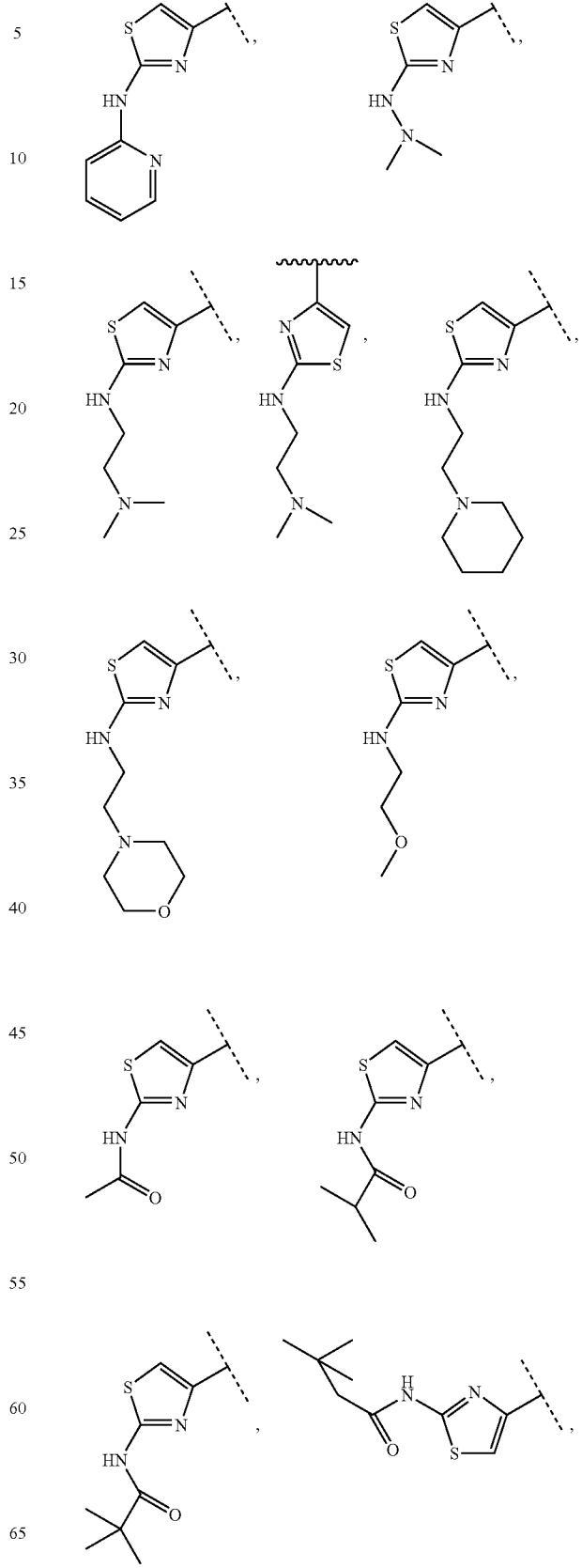

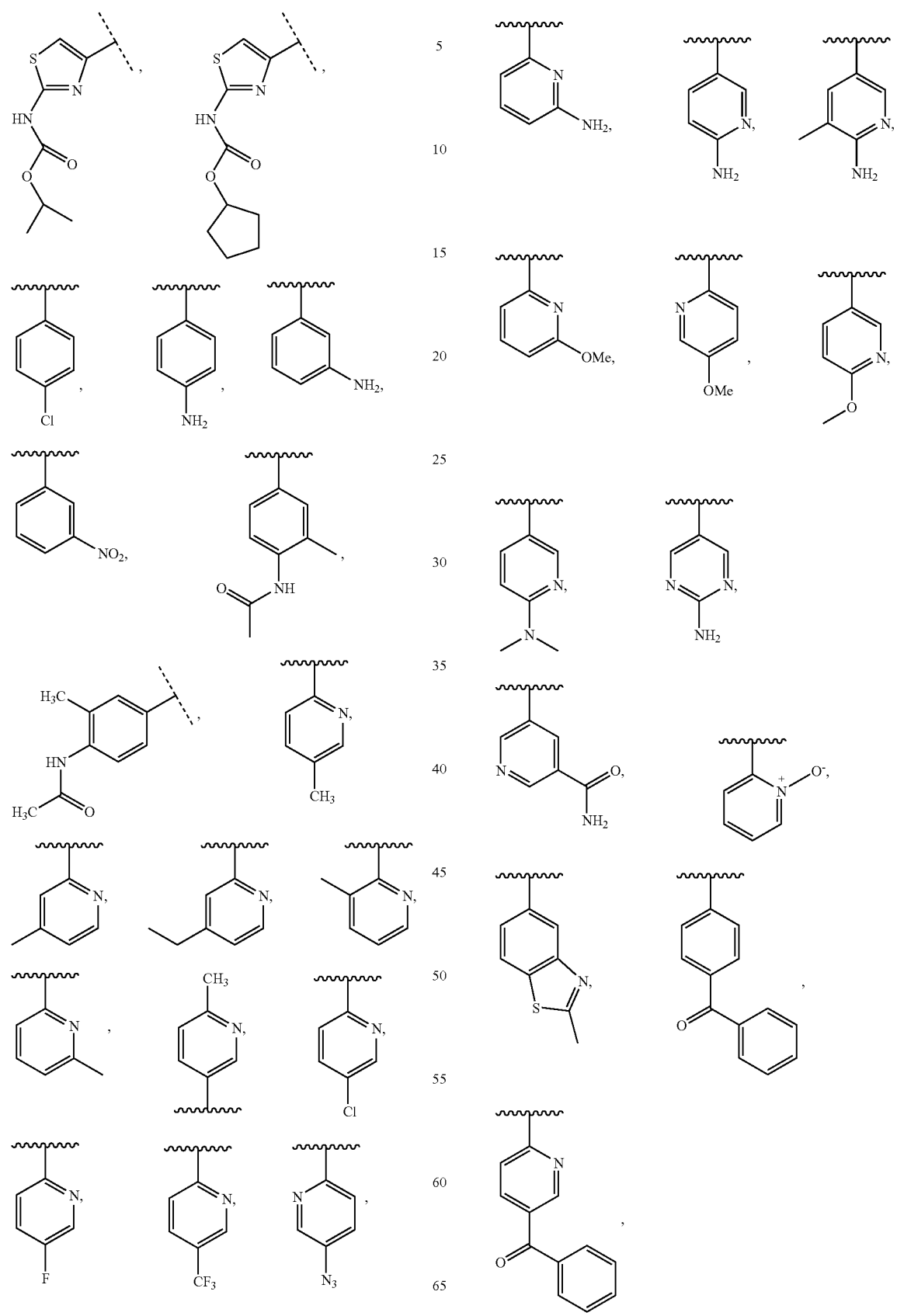

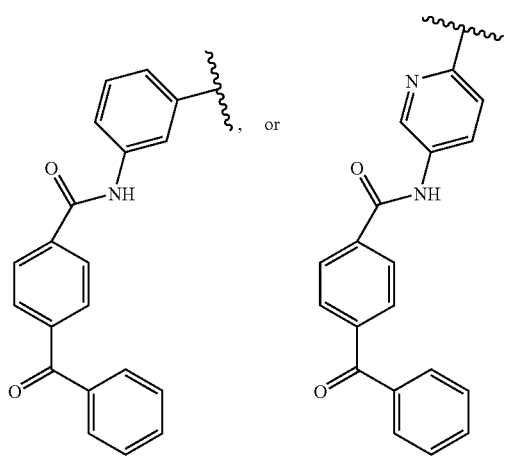
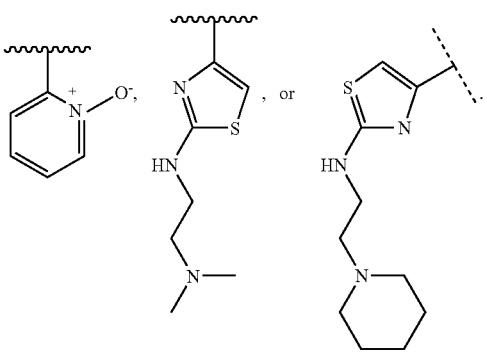
13. The compound according to claim 12, wherein $R^2$ is
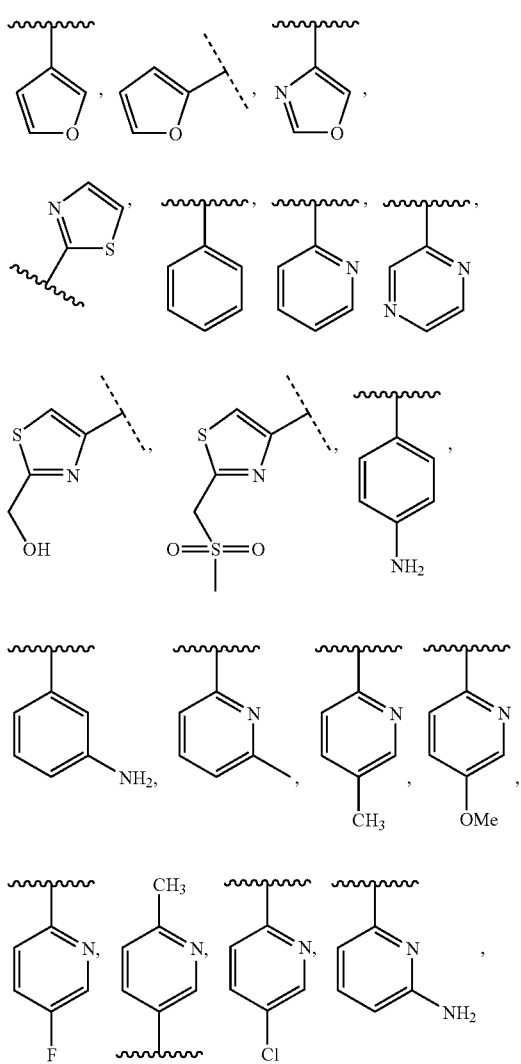
14. The compound according to claim 13, wherein $R^2$ is
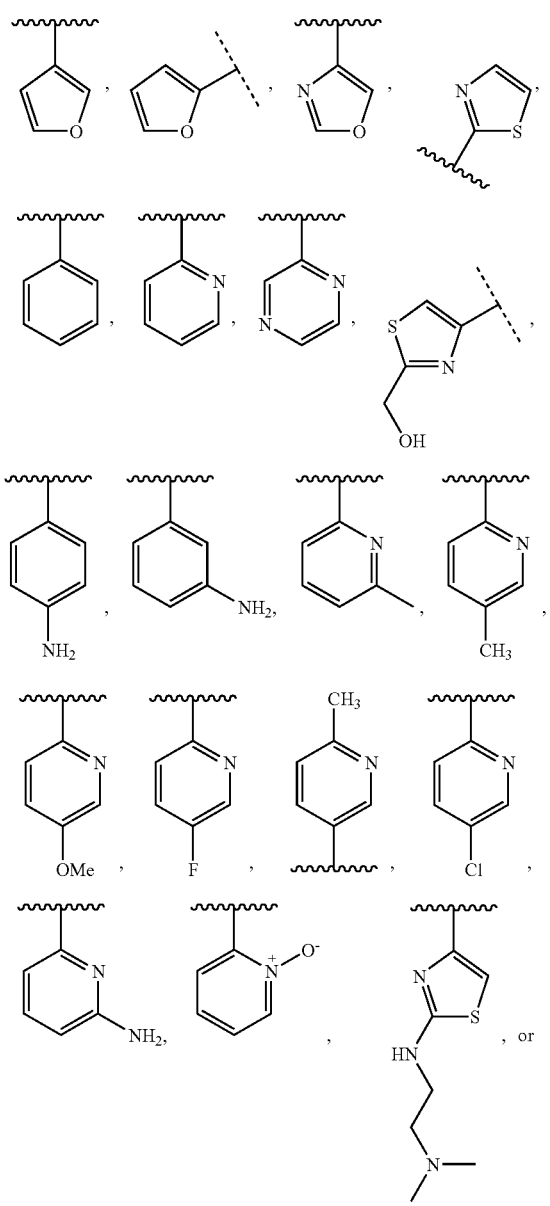

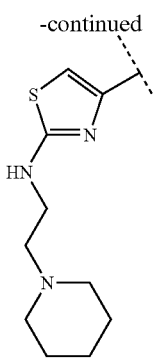

15. The compound according to claim 1, wherein $R^3$ is selected from $(C_{3-7})$cycloalkyl, $(C_{3-7})$cycloalkenyl, $(C_{6-10})$bicycloalkyl or $(C_{6-10})$bicycloalkenyl.

16. The compound according to claim 15, wherein $R^3$ is $(C_{3-7})$cycloalkyl.

17. The compound according to claim 16, wherein $R^3$ is cyclopentyl, or cyclohexyl.

18. The compound according to claim 1, wherein $Y^1$ is O.

19. The compound according to claim 1, wherein Z is $OR^6$, wherein $R^6$ is H or $(C_{1-6})$alkyl which is optionally substituted with: halo, hydroxy, carboxy, amino, $C_{1-6}$ alkoxy, $C_{1-6}$alkoxycarbonyl, or $C_{1-6}$ alkylamino; or $R^6$ is $C_{1-6}$ alkylaryl optionally substituted with: halogen, cyano, nitro, $C_{1-6}$ alkyl, $C_{1-6}$haloalkyl, $C_{1-6}$alkanoyl, $-(CH_2)_{1-6}-COOR^7$, $-(CH_2)_{1-6}-CONR^7R^8$, $-(CH_2)_{1-6}-NR^7R^8$, $-(CH_2)_{1-6}-NR^7COR^8$, $-(CH_2)_{1-6}-NHSO_2R^7$, $-(CH_2)_{1-6}-OR^7$, $-(CH_2)_{1-6}-SR^7$, $-(CH_2)_{1-6}-SO_2R^7$, or $-(CH_2)_{1-6}-SO_2NR^7R^8$, wherein each $R^7$ and each $R^8$ is H or $C_{1-6}$ alkyl, or Z is $NR^9R^{10}$ wherein each of $R^9$ and $R^{10}$ are, independently of one another, H, $C_{1-6}$alkoxy, or $C_{1-6}$alkyl optionally substituted with halo, hydroxy, carboxy, amino, $C_{1-6}$ alkoxy, $C_{1-6}$alkoxycarbonyl, and $C_{1-6}$ alkylamino.

20. The compound according to claim 19, wherein Z is OH or $O(C_{1-6}$alkyl) or Z is $NR^9R^{10}$ wherein $R^9$ is H and $R^{10}$ is H or $C_{1-6}$alkyl.

21. The compound according to claim 20, wherein Z is OH.

22. A compound of formula:

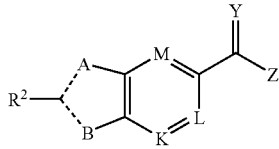

wherein A, $R^2$, $R^3$ and Z are as defined below:

| Cpd. # | A | $R^2$ | $R^3$ | Z |
|---|---|---|---|---|
| 201 | N—Me | phenyl | cyclohexyl | OH; and |
| 202 | N—Me | 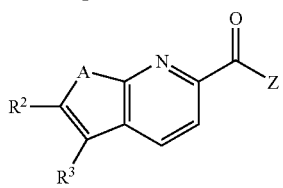 | cyclohexyl | OH. |

23. A compound represented by Formula Ia:

(Ia)

wherein:
A is $NR^1$;
B is $CR^3$;
$R^1$ is H, $(C_{1-6})$alkyl, benzyl, $(C_{1-6}$ alkyl)-$(C_{6-10}$aryl), $(C_{1-6}$ alkyl)-5- or 6-membered heterocycle having 1 to 4 heteroatoms which are, independently, O, N, or S, and 5- or 6-membered heterocycle having 1 to 4 heteroatoms which are, independently, O, N, or S,
    wherein said benzyl and said heteroatom are optionally substituted with from 1 to 4 substituents COOH, COO $(C_{1-6}$ alkyl), halogen, or $(C_{1-6}$ alkyl);
$R^2$ is H, halogen, $(C_{1-6})$alkyl, $(C_{3-7})$cycloalkyl, phenyl, 5- or 6-membered heterocycle having 1 to 4 heteroatoms which are, independently, O, N, or S, pyridine-N-oxide, or 9- or 10-membered heterobicycle having 1 to 4 heteroatoms which are, independently, O, N, or S,
    said phenyl, heterocycle and heterobicycle being optionally substituted with from 1 to 4 substituents, which are independently, halogen, $C(halogen)_3$, $(C_{1-6})$alkyl, OH, $O(C_{1-6}$ alkyl), $NH_2$, or $N(C_{1-6}$ alkyl)$_2$;
$R^3$ is norbornane or $(C_{3-7})$cycloalkyl;
M is N, $CR^4$, or $COR^5$, wherein $R^4$ is H, halogen, or $(C_{1-6}$ alkyl); and $R^5$ is H or $(C_{1-6}$ alkyl);
K and L are N or CH;
with the proviso that one and only one of M, K and L is N;
— represents either a single or a double bond;
Y is O;
Z is $OR^6$, wherein $R^6$ is H, $(C_{1-6})$alkyl, wherein said alkyl is optionally substituted with from 1 to 4 substituents which are, independently, OH, COOH, $COO(C_{1-6})$ alkyl, or $(C_{1-6})$alkyl, said alkyl being optionally substituted with from 1 to 4 substituents which are, independently, COOH, $NHCO(C_{1-6}$ alkyl), $NH_2$, $NH(C_{1-6}$ alkyl), or $N(C_{1-6}$ alkyl)$_2$;
or a salt thereof.

24. A pharmaceutical composition for the treatment of HCV infection, comprising an effective amount of a compound of formula I according to claim 1, or a pharmaceutically acceptable salt thereof, and a pharmaceutically acceptable carrier.

25. The pharmaceutical composition according to claim 24, further comprising an immunomodulatory agent.

26. The pharmaceutical composition according to claim 25, wherein said immunomodulatory agent is α-interferon, β-interferon, δ-interferon, -interferon, or ω-interferon.

27. The pharmaceutical composition according to claim 24, further comprising ribavirin or amantadine.

28. The pharmaceutical composition according to claim 24, further comprising another inhibitor of HCV polymerase.

29. The pharmaceutical composition according to claim 28, further comprising an inhibitor of other HCV target, wherein said inhibitor is helicase, polymerase, metalloprotease or IRES.

30. A method of treating HCV infection in a mammal, comprising administering to the mammal an effective amount of a pharmaceutical composition according to claim 24.

31. A compound of the formula I according to claim 1, wherein $Y^1$ is O and Z is $OR^6$.

* * * * *